United States Patent
Sakakibara et al.

(10) Patent No.: US 10,717,731 B2
(45) Date of Patent: Jul. 21, 2020

(54) NITROGEN-CONTAINING AROMATIC HETEROCYCLIC COMPOUND

(71) Applicant: MITSUBISHI TANABE PHARMA CORPORATION, Osaka-shi, Osaka (JP)

(72) Inventors: Ryo Sakakibara, Osaka (JP); Hideki Ushirogochi, Osaka (JP); Wataru Sasaki, Osaka (JP); Yuichi Onda, Osaka (JP); Minami Yamaguchi, Osaka (JP); Fumihiko Akahoshi, Osaka (JP)

(73) Assignee: MITSUBISHI TANABE PHARMA CORPORATION, Osaka-Shi (JP)

(*) Notice: Subject to any disclaimer, the term of this patent is extended or adjusted under 35 U.S.C. 154(b) by 0 days.

(21) Appl. No.: 15/769,844

(22) PCT Filed: Oct. 21, 2016

(86) PCT No.: PCT/JP2016/081214
§ 371 (c)(1),
(2) Date: Apr. 20, 2018

(87) PCT Pub. No.: WO2017/069226
PCT Pub. Date: Apr. 27, 2017

(65) Prior Publication Data
US 2018/0312503 A1 Nov. 1, 2018

(30) Foreign Application Priority Data
Oct. 23, 2015 (JP) ................. 2015-208888

(51) Int. Cl.
| | | |
|---|---|---|
| C07D 403/12 | (2006.01) | |
| C07D 403/04 | (2006.01) | |
| C07D 403/10 | (2006.01) | |
| C07D 417/12 | (2006.01) | |
| C07D 405/14 | (2006.01) | |
| C07D 405/04 | (2006.01) | |
| C07D 405/12 | (2006.01) | |
| C07D 213/74 | (2006.01) | |
| C07D 401/04 | (2006.01) | |
| C07D 401/12 | (2006.01) | |
| C07D 237/20 | (2006.01) | |
| C07D 409/12 | (2006.01) | |
| C07D 413/12 | (2006.01) | |
| C07D 241/26 | (2006.01) | |
| C07D 451/04 | (2006.01) | |
| C07D 453/02 | (2006.01) | |
| C07D 471/04 | (2006.01) | |
| C07D 471/08 | (2006.01) | |

(Continued)

(52) U.S. Cl.
CPC ......... *C07D 471/04* (2013.01); *C07D 213/74* (2013.01); *C07D 237/20* (2013.01); *C07D 241/20* (2013.01); *C07D 401/04* (2013.01); *C07D 401/12* (2013.01); *C07D 401/14* (2013.01); *C07D 403/04* (2013.01); *C07D 403/10* (2013.01); *C07D 403/12* (2013.01); *C07D 405/04* (2013.01); *C07D 405/12* (2013.01); *C07D 405/14* (2013.01); *C07D 407/10* (2013.01); *C07D 409/12* (2013.01); *C07D 413/12* (2013.01); *C07D 417/12* (2013.01); *C07D 451/04* (2013.01); *C07D 453/02* (2013.01); *C07D 471/08* (2013.01); *C07D 498/08* (2013.01)

(58) Field of Classification Search
CPC .. C07D 403/12; C07D 403/04; C07D 403/10; C07D 417/12; C07D 405/14; C07D 405/04; C07D 405/12; C07D 213/74; C07D 401/04; C07D 401/12; C07D 237/20; C07D 409/12; C07D 413/12; C07D 241/26; C07D 451/04; C07D 453/02; C07D 471/04; C07D 471/08; C07D 498/08; C07D 407/10; C07D 401/14
See application file for complete search history.

(56) References Cited

U.S. PATENT DOCUMENTS

| | | | |
|---|---|---|---|
| 8,778,929 B2* | 7/2014 | Steurer | C07D 401/14 514/211.15 |
| 2013/0225548 A1* | 8/2013 | Fujihara | C07D 213/84 514/210.2 |
| 2017/0044115 A1 | 2/2017 | Ushirogochi et al. | |

FOREIGN PATENT DOCUMENTS

| | | |
|---|---|---|
| JP | 2012-526774 A | 11/2012 |
| WO | WO 2010/034838 A2 | 4/2010 |

(Continued)

OTHER PUBLICATIONS

Azizi et al., Nephrol Dial Transplant (2013), 28, 36-43.*

(Continued)

*Primary Examiner* — Sun Jae Yoo
(74) *Attorney, Agent, or Firm* — Birch, Stewart, Kolasch & Birch, LLP

(57) ABSTRACT

A compound represented by general formula [I] wherein X represents N or the like, Y represents CH or the like; $R^4$ represents a cycloalkyl group which may be substituted or the like, $R^1$ represents an alkyl group or the like, $R^2$ represents an alkyl group which may be substituted or the like, $R^3$ represents a hydrogen atom or an alkyl group, or a pharmaceutically acceptable salt thereof has an inhibitory activity on aldosterone synthetase, and is useful as a prophylactic and/or therapeutic agent for various diseases or symptoms associated with aldosterone.

14 Claims, No Drawings

(51) Int. Cl.
*C07D 498/08* (2006.01)
*C07D 407/10* (2006.01)
*C07D 401/14* (2006.01)
*C07D 241/20* (2006.01)

(56) References Cited

FOREIGN PATENT DOCUMENTS

| WO | WO 2010/130796 A1 | 11/2010 |
|---|---|---|
| WO | WO 2012/012478 A1 | 1/2012 |
| WO | WO 2013/037779 A1 | 3/2013 |
| WO | WO 2013/079452 A1 | 6/2013 |
| WO | WO 2014/179186 A1 | 11/2014 |
| WO | WO 2015/163427 A1 | 10/2015 |

OTHER PUBLICATIONS

Diabetic-Retinopathy, 2019, https://www.drugs.com/condition/diabetic-retinopathy.html.*
Sleep-Apnea, 2019, https://www.mayoclinic.org/diseases-conditions/sleep-apnea/diagnosis-treatment/drc-20377636.*
Shihab, 2007, Clin. J. Am. Soc. Nephrol., 2, 876-878.*
RN1947178-21-3, file registry compound, entry date Jul. 7, 2016.*
Andersen, K., "Aldosterone Synthase Inhibition in Hypertension," Curr. Hypertens. Rep. (2013), vol. 15, pp. 484-488.
Cerny, M. A., "Porgress Towards Clinically Useful Aldosterone Synthase Inhibitors," Current Topics in Medicinal Chemistry (2013), vol. 13, pp. 1385-1401.
English translation of International Preliminary Report on Patentability and Written Opinion dated May 3, 2018, in PCT International Application No. PCT/JP2016/081214 (Forms PCT/IB/338, PCT/IB/373, and PCT/ISA/237).
English translation of International Search Report dated Dec. 27, 2016, in PCT International Application No. PCT/JP2016/081214.
Hu et al., "Aldosterone Synthase Inhibitors as Promising Treatments for Mineralocorticoid Dependent Cardiovascular and Renal Diseases," J. Med. Chem. (2014), vol. 57, pp. 5011-5022.
Pitt et al., "Eplerenone, a Selective Aldosterone Blocker, in Patients with Left Ventricular Dysfunction after Myocardial Infarction," The New England Journal of Medicine (Apr. 3, 2003), vol. 348, No. 14, pp. 1309-1321.
Pitt et al., "The Effect of Spironolactone on Morbidity and Mortality in Patients with Severe Heart Failure," The New England Journal of Medicine (Sep. 2, 1999), vol. 341, No. 10, pp. 709-717.
STN International, 1-Piperazineacetamide, 4-[5-(4-chlorophenyl)-1,2,4-triazin-3-yl]-N,N-dimethyl-, File Registry [online], Entered STN: Nov. 2, 2008, retrieval date: Dec. 13, 2016 (Dec. 13, 2016), CAS Registry No. 1069628-74-5.
STN International, 1-Piperazineacetamide, 4-[5-(4-methoxyphenyl)-1,2,4-triazin-3-yl] -N-(1-methylethyl)-, File Registry [online], Entered STN: Nov. 3, 2008, retrieval date: Dec. 13, 2016 (Dec. 13, 2016), CAS Registry No. 1070398-58-1.
STN International, 1-Piperazineacetamide, N,N-dimethyl-4- [6-(1H-1,2,4-triazol-1-yl)-2- pyrazinyl]-, File Registry [online], Entered STN: May 14, 2010, retrieval date: Dec. 13, 2016 (Dec. 13, 2016), CAS Registry No. 1223591-34-1.
STN International, 1-Piperazineacetamide N,N-dimethyl-4-5-[4-(trifluoromethyl)phenyl]-1,2,4-triazin-3-yl]-, File Registry [online], Entered STN: Oct. 13, 2008, retrieval date: Dec. 13, 2016 (Dec. 13, 2016), CAS Registry No. 1060824-77-2.
Database Registry [Online] Chemical Abstracts Service, Columbus, Ohio, US; "1-Piperazineacetamide, N,N-dimethyl-4-[6-(1H-1,2,4-triazoll-1-yl)-2-pyrazinyl]-", XP002790207, database accession No. 1223591-34-1, May 14, 2010.
Extended European Search Report for Application No. 16857539.7, dated Apr. 25, 2019.

\* cited by examiner

NITROGEN-CONTAINING AROMATIC HETEROCYCLIC COMPOUND

TECHNICAL FIELD

This invention relates to a novel nitrogen-containing aromatic heterocyclic compound which has an aldosterone synthetase (hereinafter also referred to as Cyp11B2) inhibitory effect and is useful for preventing and/or treating various diseases or conditions associated with aldosterone.

BACKGROUND ART

Aldosterone is a specific ligand for a mineral corticoid receptor (hereinafter also referred to as MR) and one of mediators for renin-angiotensin-aldosterone system (RAAS). Aldosterone is mainly produced in an adrenal gland and has been considered as a mineral corticoid hormone which regulates metabolism of sodium and water by affecting a distal tubule of a kidney. In a recent study, it has been shown that aldosterone is produced in various tissues such as a heart, blood vessels and a brain, and that the MR is widely found in tissues such as cardiovascular tissues. Therefore, aldosterone is recognized as a risk hormone which exerts various deleterious effects on cardiovascular tissues (e.g., heart fibrosis and necrosis; enhanced effect of catecholamine, and decrease of a baroreceptor reaction), in addition to, as an exacerbation factor for hypertension.

A means of blocking an effect of aldosterone is an effective method for treating, for example, cardiovascular diseases associated with said aldosterone and a receptor thereof. An MR antagonist (e.g., eplerenone or spironolactone), which has an affinity for MR and blocks its receptor function, has already been used for treating hypertension. In large clinical tests (RALES and EPHESUS), it was confirmed that, by combined administration of the MR antagonist and a conventional therapeutic agent such as an ACE inhibitor, a hospitalization rate, and a mortality rate caused by cardiac diseases in patients with severe heart failure were significantly decreased, and that prognosis of patients with acute myocardial infarction was significantly improved (non-patent documents 1 and 2). On the other hand, the MR antagonist (e.g., spironolactone or eplerenone) has specific serious adverse effects (e.g., hyperkalemia). In addition, use of spironolactone is often associated with gynecomastia, menstrual disorders, erectile dysfunction, and the like. Accordingly, it is desired to develop a compound for treating a disease associated with aldosterone which has no such adverse effect and has higher safety. An aldosterone synthetase (Cyp11B2) inhibitor has been proposed as an alternative approach from the point of view above (i.e., another approach for blocking or reducing an effect of aldosterone).

Cyp11B2 is a cytochrome P450 enzyme and is known as an enzyme which catalyzes a series of reactions leading from 11-deoxycorticosterone (i.e., an aldosterone precursor) to aldosterone. Cyp11B2 is mainly expressed in an adrenal cortex spherical layer and a level of plasma aldosterone is regulated by enzymic activity of Cyp11B2 present in an adrenal gland. In addition, it has been confirmed that aldosterone was expressed in some tissues other than adrenal glands such as a cardiovascular system, a kidney, adipose tissues and a brain, as well as, it has drawn attention that organ disorders were associated with aldosterone, which was locally produced in each organ. It has been reported that an inhibitor of Cyp11B2 inhibited production of aldosterone through studies using the enzyme and cells in culture, and that the inhibitor had a suppressive effect against production of aldosterone and any therapeutic effect through studies using various experimental animal models. Further, it has been confirmed that a Cyp11B2 inhibitor showed a plasma aldosterone level-lowering effect and a urine aldosterone level-lowering effect as well as an antihypertensive effect in hypertensive patients and primary aldosteronism patients (non-patent documents 3 and 4). A highly feasible approach for establishing an effective therapy for various diseases associated with aldosterone is to find a means for inhibiting a biosynthesis route of aldosterone.

Previously, although aryl pyridine compounds (patent document 1), benzimidazol substituted pyridine compounds (patent document 2), and the like are known as a compound having an aldosterone synthetase (Cyp11B2) inhibitory activity, it has not been reported that a nitrogen-containing aromatic heterocyclic compound such as a compound of the present invention had an aldosterone synthetase inhibitory activity.

PRIOR ART DOCUMENT(S)

Patent Document(s)

[Patent document 1] WO2010/130796
[Patent document 2] WO2012/012478

NON-PATENT DOCUMENT(S)

[Non-patent document 1] New England Journal of Medicine,
[Non-patent document 2] New England Journal of Medicine, 2003; 348: p. 1309-1321
[Non-patent document 3] Current Topics in Medicinal Chemistry, 2013; 313: p. 1385-1401
[Non-patent document 4] Current Hypertension Reports, 2013; 15: p. 484-488

DISCLOSURE OF INVENTION

Problem to be Solved by the Invention

The present invention relates to a novel nitrogen-containing aromatic heterocyclic compound or a pharmaceutically acceptable salt thereof which has an aldosterone synthetase (Cyp11B2) inhibitory effect. The compound of the present invention is useful for preventing and/or treating various diseases or conditions associated with aldosterone.

Means for Solving Problem

Specifically, the present invention is as follows:
a compound of the following formula [I]:

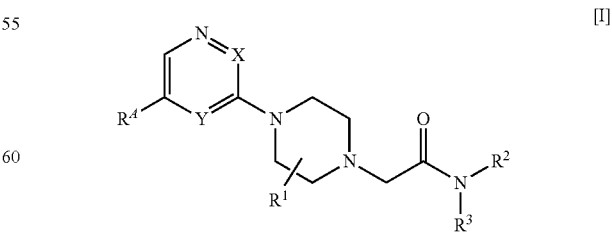

wherein
X and Y represent any of the following (1) to (3):
(1) X is N, and Y is CH or C—$R^Y$, (2) X is CH, and Y is N, or
(3) X is CH, and Y is CH;

$R^Y$ represents an alkyl group;

$R^A$ represents a cycloalkyl group which may be substituted, a cycloalkenyl group which may be substituted, an aryl group which may be substituted, or a 6- to 10-membered monocyclic or bicyclic heteroaryl group which may be partially hydrogenated and may be substituted;

$R^1$ represents a hydrogen atom, or an alkyl group;

$R^2$ represents an alkyl group which may be substituted, a cycloalkyl group which may be substituted, an aliphatic heterocyclic group which may be substituted, or a heteroaryl group which may be partially hydrogenated and may be substituted;

$R^3$ represents a hydrogen atom, or an alkyl group, or a pharmaceutically acceptable salt thereof.

In addition, the present invention relates to a method for preventing or treating various diseases or conditions associated with aldosterone, comprising administering a therapeutically effective amount of a compound of the above formula [I] or a pharmaceutically acceptable salt thereof. Additionally, the present invention relates to a pharmaceutical composition comprising the above compound [I] or a pharmaceutically acceptable salt thereof as an active ingredient as well as to use of the compound [I] for manufacturing the composition. Furthermore, the present invention relates to the above compound [I] or a pharmaceutically acceptable salt thereof, and a pharmaceutical composition comprising said compound or a salt thereof as an active ingredient, for use in prevention or treatment of various diseases or conditions associated with aldosterone. Furthermore, the present invention relates to a method for preparing the above compound [I] or a pharmaceutically acceptable salt thereof.

Effect of Invention

A compound [I] of the present invention or a pharmaceutically acceptable salt thereof has an excellent inhibitory activity against aldosterone synthetase (Cyp11B2), and therefore, it is useful for preventing or treating various diseases and/or disease states evoked by an increased level of aldosterone and/or overproduction of aldosterone, such as hypertension, primary aldosteronism, or for improving prognosis of these diseases.

BEST MODE FOR CARRYING OUT THE INVENTION

The definitions of each group can be freely combined unless otherwise stated.

In the present invention, alkyl refers to a straight or branched chain saturated hydrocarbon group containing 1-6 carbons ($C_{1-6}$). Particularly, an alkyl group containing 1-5 carbons ($C_{1-5}$) is preferable. Specifically, alkyl includes methyl, ethyl, n-propyl, i-propyl, n-butyl, i-butyl, 1,2-dimethylpropyl, t-butyl, i-amyl, n-pentyl, n-hexyl and the like. Particularly, methyl, ethyl, i-propyl, i-butyl, 1,2-dimethylpropyl, t-butyl and the like are preferable.

Cycloalkyl refers to a monocyclic saturated hydrocarbon group containing 3-7 carbons ($C_{3-7}$). Particularly, a cycloalkyl group containing 5-6 carbons ($C_{5-6}$) is preferable. Specifically, cycloalkyl includes cyclopropyl, cyclobutyl, cyclopentyl, cyclohexyl, cycloheptyl, and the like. Particularly, cyclopentyl, cyclohexl and the like are preferable.

Cycloalkenyl refers to a cyclic group containing 3-7 carbons ($C_{3-7}$) having at least one double bond. Specifically, cycloalkenyl includes cyclopropenyl, cyclobutenyl, cyclopentenyl, cyclohexenyl, and the like. Particularly, cyclohexenyl is preferable.

Alkoxy refers to a monovalent group wherein the above alkyl is bound to oxygen. Alkoxy includes a straight or branched chain alkyl-O— containing 1-6 carbons ($C_{1-6}$). Alkyl-O— containing 1-4 carbons ($C_{1-4}$) is preferable. Specifically, alkoxy includes methoxy, ethoxy, n-propoxy, i-propoxy, n-butoxy, t-butoxy, and the like. Particularly, methoxy is preferable.

Halogen or halo refers to fluorine, chlorine, bromine or iodine. Fluorine and chlorine are preferable.

Haloalkyl means the above alkyl substituted with 1-3 halogen atoms, and is preferably trifluoromethyl.

Alkoxyalkyl means the above alkyl substituted with 1-2 alkoxy groups, and is preferably methoxymethyl, methoxyethyl, methoxypropyl, and the like.

Alkanoyl refers to a monovalent group wherein a carbonyl group is bound to the above alkyl. Alkanoyl includes a straight or branched chain alkyl-CO— containing 1-6 carbons ($C_{1-6}$). Specifically, alkanoyl includes acetyl, propionyl, pivaloyl, butanoyl, pentanoyl, hexanoyl, and heptanoyl.

Aryl refers to a 6- to 10-membered aromatic hydrocarbon group, and a monocyclic or bicyclic aryl is preferable. Specifically, aryl includes phenyl, and naphthyl, and especially, phenyl is preferable.

Heteroaryl refers to a 5- to 10-membered aromatic heterocyclic group having 1-4 heteroatoms independently selected from the group consisting of a sulfur atom, an oxygen atom, and a nitrogen atom, and a monocyclic or bicyclic heteroaryl is preferable. More preferably, heteroaryl is a 5- to 10-membered monocyclic or bicyclic heteroaryl having 1-2 heteroatoms independently selected from the group consisting of a sulfur atom, an oxygen atom, and a nitrogen atom. In addition, other preferable heteroaryl is a 5- to 10-membered monocyclic or bicyclic heteroaryl which contains at least 1 nitrogen atom, and additionally may contain 1 heteroatom selected from the group consisting of a sulfur atom, an oxygen atom, and a nitrogen atom. Other preferable heteroaryl includes a 6- to 10-membered monocyclic or bicyclic heteroaryl. Particularly, a 6- to 10-membered monocyclic or bicyclic heteroaryl having 1-2 heteroatoms independently selected from the group consisting of a sulfur atom, an oxygen atom, and a nitrogen atom is preferable. Specifically, heteroaryl includes pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, benzopyranyl, and the like.

Partially hydrogenated heteroaryl refers to the above heteroaryl which is partially hydrogenated, and also includes, for example, a cyclic group formed by condensation between a phenyl group and an aliphatic heterocyclic group, a cyclic group formed by condensation between a heteroaryl group and a cycloalkyl group, and the like. Specifically, partially hydrogenated heteroaryl includes imidazolinyl, dihydrobenzofuranyl, dihydrobenzopyranyl, tetrahydrobenzimidazolyl, tetrahydroimidazopyridyl, isoindolinyl, and the like.

Heteroaryl which may be partially hydrogenated includes pyrrolyl, furanyl, thienyl, imidazolyl, imidazolinyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, isoindolinyl, indazolyl, benzimidazolyl, tetrahydrobenzimidazolyl, benzothiazolyl, benzofuranyl, dihydrobenzofuranyl, quinolyl, isoquinolyl, imidazopyridyl, tetrahydroimidazopyridyl, benzopyranyl, dihydrobenzopyranyl, and the like. Pyrazolyl, pyridyl, indazolyl, benzimidazolyl, tetrahydrobenzimidazolyl, benzofuranyl, and dihydrobenzofuranyl are preferable. For example, a heteroaryl moiety in the "6- to 10-membered monocyclic or bicyclic heteroaryl group which may be partially hydrogenated and may be substituted", represented by $R^4$ in the above general formula [I], includes pyridyl, pyrazinyl, pirimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, benzopyranyl, and the like. Particularly, pyridyl, indazolyl, or benzofuranyl is preferable, and indazolyl is especially preferable.

Further, as another preferable example, a heteroaryl moiety in the "heteroaryl group which may be partially hydrogenated and may be substituted", represented by $R^2$ in the above formula [I], includes pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, benzopyranyl, and the like. Particularly, pyrazolyl, pyridyl, benzimidazolyl, and the like are preferable.

Furthermore, in another preferable example, the heteroaryl group which may be substituted includes a pyrimidinyl group.

An aliphatic heterocyclic ring refers to a 4- to 9-membered saturated cyclic group having 1-3 heteroatoms independently selected from the group consisting of a sulfur atom, an oxygen atom, and a nitrogen atom. In addition, an aliphatic heterocyclic ring also includes a group wherein the ring-constituting two carbon atoms are cross-linked by an alkylene group to form a bicyclo ring. Specifically, azetidinyl, oxetanyl, pyrrolidinyl, tetrahydrothienyl, tetrahydrofuranyl, thiazolidinyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, diazabicyclo[2.2.1]heptyl, 3-oxo-9-azabicyclo[3.3.1]nonyl, and the like, are preferable.

As one embodiment, the present invention includes a compound of the above formula [I]:
wherein
X and Y represent any of the following (1) to (3):
(1) X is N, and Y is CH or C—$R^Y$,
(2) X is CH, and Y is N, or
(3) X is CH, and Y is CH;
$R^Y$ represents an alkyl group;
substituents of the cycloalkyl group which may be substituted, the cycloalkenyl group which may be substituted, the aryl group which may be substituted, and the 6- to 10-membered monocyclic or bicyclic heteroaryl group which may be partially hydrogenated and may be substituted, represented by $R^4$, are 1-3 groups each independently selected from the group consisting of a halogen atom, a cyano group, an alkyl group, a haloalkyl group, an alkoxyalkyl group, and an alkoxy group,
in the aryl group which may be substituted, represented by $R^4$, an aryl moiety is a 6- to 10-membered monocyclic or bicyclic aryl,
in the 6- to 10-membered heteroaryl group which may be partially hydrogenated and may be substituted, represented by $R^4$, the heteroaryl moiety is a 6- to 10 membered monocyclic or bicyclic heteroaryl containing 1-2 heteroatoms independently selected from the group consisting of a sulfur atom, an oxygen atom, and a nitrogen atom;

a substituent of (i) the alkyl group which may be substituted, represented by $R^2$, is 1-3 groups each independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, substituents of (ii) the cycloalkyl group which may be substituted, (iii) the aliphatic heterocyclic group which may be substituted, and (iv) the heteroaryl group which may be partially hydrogenated and may be substituted are 1-3 groups each independently selected from the group consisting of a halogen atom; a hydroxyl group; an oxo group; an alkyl group which may be substituted with 1-3 groups independently selected from the group consisting of a carbamoyl group which may be substituted with 1-2 alkyl groups, a hydroxyl group, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iv), the aliphatic heterocyclic group is a 4- to 9-membered monocyclic or bicyclic aliphatic heterocyclic group containing 1 to 2 heteroatoms independently selected from a sulfur atom, an oxygen atom, or a nitrogen atom, in the respective substituents of the above (i) to (iv), the heteroaryl group is a 5- to 10-membered monocyclic or bicyclic heteroaryl group containing 1 to 4 heteroatoms independently selected from the group consisting of a sulfur atom, an oxygen atom, and a nitrogen atom, in the aliphatic heterocyclic group which may be substituted, represented by $R^2$, the aliphatic heterocyclic moiety is a 4- to 9-membered monocyclic or bicyclic aliphatic heterocyclic ring containing 1 to 3 heteroatoms independently selected from the group consisting of a sulfur atom, an oxygen atom, and a nitrogen atom; and in the heteroaryl group which may be partially hydrogenated and may be substituted, represented by $R^2$, the heteroaryl moiety is a 5- to 10-membered monocyclic or bicyclic heteroaryl, $R^3$ is a hydrogen atom, or an alkyl group,
or a pharmaceutically acceptable salt thereof.

As another preferred embodiment, the present invention includes a compound of the above formula [I]:
wherein
X and Y represent any of the following (1) to (3):
(1) X is N, and Y is CH or C—$R^Y$,
(2) X is CH, and Y is N, or
(3) X is CH, and Y is CH;
$R^Y$ represents an alkyl group;
substituents of the cycloalkyl group which may be substituted, the cycloalkenyl group which may be substituted, the aryl group which may be substituted, and the 6- to 10-membered monocyclic or bicyclic heteroaryl group which may be partially hydrogenated and may be substituted, represented by $R^A$, are 1-3 groups each independently selected from the group consisting of a halogen atom, a cyano group, an alkyl group, a haloalkyl group, an alkoxyalkyl group, and an alkoxy group, in the aryl group which may be substituted, represented by $R^A$, the aryl moiety is phenyl or naphthyl, in the 6- to 10-membered monocyclic or bicyclic heteroaryl group which may be partially hydrogenated and may be substituted, represented by $R^A$, the heteroaryl moiety is pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl;

a substituent of (i) the alkyl group which may be substituted, represented by $R^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, substituents of (ii) the cycloalkyl group which may be substituted, (iii) the aliphatic heterocyclic group which may be substituted, and (iv) the heteroaryl group which may be partially hydrogenated and may be substituted, represented by $R^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iv), the aliphatic heterocyclic group is a group independently selected from the group consisting of azetidinyl, oxetanyl, pyrrolidinyl, tetrahydrothienyl, tetrahydrofuranyl, thiazolidinyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, and 3-oxo-9-azabicyclo[3.3.1]nonyl, in the respective substituents of the above (i) to (iv), the heteroaryl group is a group independently selected from the group consisting of pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, and benzopyranyl, in the aliphatic heterocyclic group which may be substituted, represented by $R^2$, the aliphatic heterocyclic moiety is azetidinyl, oxetanyl, pyrrolidinyl, tetrahydrothienyl, tetrahydrofuranyl, thiazolidinyl, piperidinyl, piperazinyl, morpholinyl, thiomorpholinyl, homomorpholinyl, tetrahydrothiopyranyl, tetrahydropyranyl, 1-azabicyclo[2.2.2]octyl (quinuclidinyl), 8-azabicyclo[3.2.1]octyl, 3-oxabicyclo[3.3.1]nonyl, or 3-oxo-9-azabicyclo[3.3.1]nonyl, in the heteroaryl group which may be partially hydrogenated and may be substituted, represented by $R^2$, the heteroaryl moiety is pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl, $R^3$ is a hydrogen atom, or an alkyl group, or a pharmaceutically acceptable salt thereof.

More preferably, the present invention includes a compound of the above formula [I], wherein a heteroaryl group which may be partially hydrogenated in the "6- to 10-membered monocyclic or bicyclic heteroaryl group which may be partially hydrogenated and may be substituted", represented by $R^A$, is a group selected from the group consisting of a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a tetrahydrobenzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, and a dihydrobenzopyranyl group, a heteroaryl group which may be partially hydrogenated in the "heteroaryl group which may be partially hydrogenated and may be substituted", represented by $R^2$, is a group selected from the group consisting of a pyrrolyl group, a furanyl group, a thienyl group, an imidazolyl group, an imidazolinyl group, a pyrazolyl group, an oxazolyl group, a thiazolyl group, a triazolyl group, a tetrazolyl group, a pyridyl group, a pyrazinyl group, a pyrimidinyl group, a pyridazinyl group, a thiazinyl group, a triazinyl group, an indolyl group, an isoindolyl group, an isoindolinyl group, an indazolyl group, a benzimidazolyl group, a tetrahydrobenzimidazolyl group, a benzothiazolyl group, a benzofuranyl group, a dihydrobenzofuranyl group, a quinolyl group, an isoquinolyl group, an imidazopyridyl group, a tetrahydroimidazopyridyl group, a benzopyranyl group, and a dihydrobenzopyranyl group, or a pharmaceutically acceptable salt thereof.

Also, as another preferred embodiment, the present invention includes a compound of the above formula [I]:
wherein
X and Y represent any of the following (1) to (3):
(1) X is N, and Y is CH or C—$R^Y$,
(2) X is CH, and Y is N, or
(3) X is CH, and Y is CH;
$R^Y$ represents an alkyl group;

substituents of the cycloalkyl group which may be substituted, the cycloalkenyl group which may be substituted, the aryl group which may be substituted, and the 6- to 10-membered monocyclic or bicyclic heteroaryl group which may be partially hydrogenated and may be substituted, represented by $R^A$, are 1-3 groups each independently selected from the group consisting of a halogen atom, a cyano group, an alkyl group, a haloalkyl group, an alkoxyalkyl group, and an alkoxy group, in the aryl group which may be substituted, represented by $R^4$, the aryl moiety is phenyl or naphthyl, in the 6- to 10-membered monocyclic or bicyclic heteroaryl group which may be partially hydrogenated and may be substituted, represented by $R^4$, the heteroaryl moiety is pyridyl, indazolyl, or benzofuranyl;

a substituent of (i) the alkyl group which may be substituted, represented by $R^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, substituents of (ii) the cycloalkyl group which may be substituted, (iii) the aliphatic heterocyclic group which may be substituted, and (iv) the heteroaryl group which may be partially hydrogenated and may be substituted, represented by $R^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iv), the aliphatic heterocyclic group is a group independently selected from piperidinyl, piperazinyl, morpholinyl, thiomorpholinyl, and tetrahydropyranyl, in the respective substituents of the above (i) to (iv), the heteroaryl group is independently a pyrimidinyl group, in the aliphatic heterocyclic group which may be substituted, represented by $R^2$, the aliphatic heterocyclic moiety is pyrrolidinyl, piperidinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, in the heteroaryl group which may be partially hydrogenated and may be substituted, represented by $R^2$, the heteroaryl moiety is pyrazolyl, pyridyl, or benzimidazolyl, $R^3$ is a hydrogen atom, or an alkyl group, or a pharmaceutically acceptable salt thereof.

More preferably, the present invention includes a compound of the above formula [I]:
wherein a heteroaryl group which may be partially hydrogenated in the "6- to 10-membered monocyclic or bicyclic heteroaryl group which may be partially hydrogenated and may be substituted", represented by $R^4$, is a group selected from the group consisting of a pyridyl group, an indazolyl group, and a dihydrobenzofuranyl group, a heteroaryl group which may be partially hydrogenated in the "heteroaryl group which may be partially hydrogenated and may be substituted", represented by $R^2$, is a group selected from the group consisting of a pyrazolyl group, a pyridyl group, and a tetrahydrobenzimidazolyl group, or a pharmaceutically acceptable salt thereof.

Also, as another preferred embodiment, the present invention includes a compound of the above formula [I]:
wherein
X and Y represent any of the following (1) to (3):
(1) X is N, and Y is CH or C—$R^Y$,
(2) X is CH, and Y is N, or
(3) X is CH, and Y is CH;
$R^Y$ represents an alkyl group;
$R^4$ is
(1) a cycloalkyl group which may be substituted with an alkyl group,
(2) a cycloalkenyl group which may be substituted with an alkyl group,
(3) a phenyl group which may be substituted with 1-3 groups independently selected from the group consisting of a halogen atom, an alkyl group, a haloalkyl group, an alkoxyalkyl group, and an alkoxy group,
(4) a naphthyl group, or
(5) a heteroaryl group which may be partially hydrogenated and may be substituted with 1-2 groups independently selected from the group consisting of a cyano group, an alkyl group, and a haloalkyl group, in the heteroaryl group which may be partially hydrogenated and may be substituted, represented by $R^4$, the heteroaryl moiety is pyridyl, indazolyl, or benzofuranyl, $R^1$ is a hydrogen atom, or an alkyl group, $R^2$ is (i) an alkyl group which may be substituted with 1-3 groups independently selected from the group consisting of a hydroxyl group; a halogen atom; and an aliphatic heterocyclic group which may be substituted with 1-2 substituents independently selected from the group consisting of a hydroxyl group, an oxo group, an alkyl group, an alkoxycarbonyl group, and an alkylsulfonyl group (wherein the aliphatic heterocyclic group is a piperidinyl group, a piperazinyl group, a morpholinyl group, or a thiomorpholinyl group), (ii) a cycloalkyl group which may be substituted with 1-3 groups independently selected from the group consisting of a hydroxyl group; an alkyl group which may be substituted with a hydroxyl group; an alkoxy group which may be substituted with a carbamoyl group which may be substituted with 1-2 alkyl groups; an amino group which may be substituted with 1-2 groups independently selected from the group consisting of an alkyl group, and an alkanoyl group; and an aliphatic heterocyclic group which may be substituted with 1-2 groups independently selected from the group consisting of a hydroxyl group, and an oxo group (wherein the aliphatic heterocyclic group is a piperidinyl group, a morpholinyl group, or a piperazinyl group), (iii) an aliphatic heterocyclic group which may be substituted with 1-3 groups independently selected from the group consisting of a halogen atom; a hydroxyl group; an oxo group; an alkyl group which may be substituted with 1-2 groups independently selected from the group consisting of a carbamoyl group which may be substituted with 1-2 alkyl groups, a hydroxyl group, and an alkylsulfonyl group; an alkoxy group; an alkoxycarbonyl group; a tetrahydropyranyl group; and a pyrimidinyl group, or (iv) a heteroaryl group which may be partially hydrogenated and may be substituted with an alkyl group which may be substituted with a carbamoyl group which may be substituted with 1-2 alkyl groups, in the aliphatic heterocyclic group which may be substituted, represented by $R^2$, the aliphatic heterocyclic moiety is pyrrolidinyl, piperidinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, in the heteroaryl group which may be partially hydrogenated and may be substituted, represented by $R^2$, the heteroaryl moiety is pyrazolyl, pyridyl, or benzimidazolyl, $R^3$ is a hydrogen atom, or a pharmaceutically acceptable salt thereof.

More preferably, the present invention includes a compound of the above formula [I]:
wherein a heteroaryl group which may be partially hydrogenated in the "6- to 10-monocyclic or bicyclic heteroaryl group which may be partially hydrogenated and may be substituted", represented by $R^4$, is a group selected from the group consisting of a pyridyl group, an indazolyl group, and a dihydrobenzofuranyl group, a heteroaryl group which may be partially hydrogenated in the "heteroaryl group which may be partially hydrogenated and may be substituted", represented by $R^2$, is a group selected from the group consisting of a pyrazolyl group, a pyridyl group, and a tetrahydrobenzimidazolyl group, or a pharmaceutically acceptable salt thereof.

Also, as the compound of the present invention, the preferred compound is a compound of the above formula [I]:
wherein X is N, Y is CH or C—$R^Y$, $R^Y$ is an alkyl group, $R^4$ is (1) a cyclohexyl group which may be substituted with an alkyl group, (2) a cyclohexenyl group which may be substituted with an alkyl group, (3) a phenyl group which may be substituted with 1-2 groups independently selected from the group consisting of a halogen atom, an alkyl group, a haloalkyl group, an alkoxyalkyl group, and an alkoxy group, (4) a naphthyl group, or (5) a heteroaryl group which may be partially hydrogenated and may be substituted with a cyano group, in the heteroaryl group which may be partially hydrogenated and may be substituted, represented by $R^4$, the heteroaryl moiety is pyridyl, or benzofuranyl, $R^1$ is a hydrogen atom, $R^2$ is (i) an alkyl group which may be substituted with 1-3 groups independently selected from the group consisting of a hydroxyl group; and an aliphatic heterocyclic group which may be substituted with 1-2 groups independently selected from the group consisting of an oxo group, an alkyl group, an alkoxycarbonyl group, and an alkylsulfonyl group (wherein the aliphatic heterocyclic group is selected from a piperidinyl group, a piperazinyl group, a morpholinyl group, or a thiomorpholinyl group), (ii) a cycloalkyl group which may be substituted with 1-3 groups independently selected from the group consisting of an alkoxy group which may be substituted with a carbamoyl group which may be substituted with 1-2 alkyl groups; an amino group which may be substituted with 1-2 groups independently selected from the group consisting of an alkyl group, and an alkanoyl group; and a morpholinyl group, (iii) an aliphatic heterocyclic group which may be substituted with 1-3 groups independently selected from the group consisting of a halogen atom; a hydroxyl group; an oxo group; an alkyl group which may be substituted with 1-2 groups independently selected from the group consisting of a carbamoyl group which may be substituted with 1-2 alkyl groups, a hydroxyl group, and an alkylsulfonyl group; an alkoxycarbonyl group; and an alkoxy group, or (iv) a pyridyl group, in the aliphatic heterocyclic group which may be substituted, represented by $R^2$, the aliphatic heterocyclic moiety is piperidinyl, tetrahydrothiopyranyl, or tetrahydropyranyl, $R^3$ is a hydrogen atom, or a pharmaceutically acceptable salt thereof.

As another preferred embodiment, the present invention includes a compound of the above formula [I]:
wherein X is CH, Y is N, $R^4$ is (1) an cyclohexyl group which may be substituted with an alkyl group, (2) a phenyl group which may be substituted with 1-2 groups independently selected from the group consisting of a halogen atom, an alkyl group, and a haloalkyl group, (3) a heteroaryl group which may be partially hydrogenated and may be substituted with 1-2 groups independently selected from the group consisting of a cyano group, and an alkyl group, in the heteroaryl group which may be partially hydrogenated and may be substituted, represented by $R^4$, the heteroaryl moiety is pyridyl, indazolyl, or benzofuranyl, $R^1$ is a hydrogen atom or an alkyl group, $R^2$ is (i) an alkyl group which may be substituted with 1-3 groups independently selected from the group consisting of a hydroxyl group; a halogen atom; and a piperidinyl group which may be substituted with 1-2 groups independently selected from the group consisting of a hydroxyl group, and an alkyl group, (ii) a cycloalkyl group which may be substituted with 1-3 groups independently selected from the group consisting of a hydroxyl group; an alkyl group which may be substituted with a hydroxyl group; an alkoxy group; an amino group which may be substituted with 1-2 groups independently selected from the group consisting of an alkyl group, and an alkanoyl group; and an aliphatic heterocyclic group which may be substituted with 1-2 oxo groups (wherein the aliphatic heterocyclic group is selected from a morpholinyl group or a piperazinyl group), (iii) an aliphatic heterocyclic group which may be substituted with 1-3 groups independently selected from the group consisting of an oxo group; an alkyl group which may be substituted with an alkylsulfonyl group; a tetrahydropyranyl group; and a pyrimidinyl group, or (iv) a pyrazolyl group which may be substituted with an alkyl group which may be substituted with a carbamoyl group which may be substituted with 1-2 alkyl groups, in the aliphatic heterocyclic group which may be substituted, represented by $R^2$, the aliphatic heterocyclic moiety is pyrrolidinyl, piperidinyl, tetrahydrothiopyranyl, or 1-azabicyclo[2.2.2]octyl(quinuclidinyl), $R^3$ is a hydrogen atom, or a pharmaceutically acceptable salt thereof.

As still another preferred compound, the present invention includes a compound of the above formula [I]:

wherein
X is CH, Y is CH,
R$^4$ is
(1) a cyclohexyl group which may be substituted with an alkyl group,
(2) a cyclohexenyl group which may be substituted with an alkyl group,
(3) a phenyl group which may be substituted with 1-2 groups independently selected from the group consisting of a halogen atom, and an alkyl group, or
(4) a heteroaryl group which may be partially hydrogenated and may be substituted with 1-2 groups independently selected from the group consisting of a cyano group, an alkyl group, and an haloalkyl group,
in the heteroaryl group which may be partially hydrogenated and may be substituted, represented by R$^4$, the heteroaryl moiety is pyridyl, indazolyl, or benzofuranyl;
R$^1$ is a hydrogen atom,
R$^2$ is
(i) an alkyl group which may be substituted with a hydroxyl group,
(ii) a cycloalkyl group which may be substituted with 1-3 groups independently selected from the group consisting of an amino group which may be substituted with 1-2 groups independently selected from the group consisting of an alkyl group, and an alkanoyl group; and a piperidinyl group which may be substituted with a hydroxyl group,
(iii) an aliphatic heterocyclic group which may be substituted with 1-3 groups independently selected from the group consisting of a hydroxyl group; an alkyl group; and an alkoxycarbonyl group, or
(iv) a heteroaryl group which may be partially hydrogenated and may be substituted with an alkyl group which may be substituted with a carbamoyl group which may be substituted with 1-2 alkyl groups,
in the aliphatic heterocyclic group which may be substituted, represented by R$^2$, the aliphatic heterocyclic moiety is 8-azabicyclo[3.2.1]octyl, 3-oxabicyclo[3.3.1]nonyl, or 3-oxo-9-azabicyclo[3.3.1]nonyl,
in the heteroaryl group which may be partially hydrogenated and may be substituted, represented by R$^2$, the heteroaryl moiety is pyrazolyl, or benzimidazolyl,
R$^3$ is a hydrogen atom,
or a pharmaceutically acceptable salt thereof.
Further, as another preferred embodiment, the present invention includes a compound of the above formula [I]:
wherein
X and Y are any of the following (1)-(3),
(1) X is N, and Y is CH,
(2) X is CH, and Y is N, or
(3) X is CH, and Y is CH;
R$^4$ is an aryl group which may be substituted, or a 6- to 10-membered monocyclic or bicyclic heteroaryl group which may be partially hydrogenated and may be substituted;
R$^1$ is a hydrogen atom;
R$^2$ is an alkyl group which may be substituted, a cycloalkyl group which may be substituted, or an aliphatic heterocyclic group which may be substituted;
R$^3$ is a hydrogen atom,
or a pharmaceutically acceptable salt thereof.
Furthermore, as another preferred embodiment, the present invention includes a compound of the above formula [I]:
wherein
X and Y are any of the following (1)-(3),
(1) X is N, and Y is CH,
(2) X is CH, and Y is N, or
(3) X is CH, and Y is CH;

substituents of the aryl group which may be substituted, and the 6- to 10-membered monocyclic or bicyclic heteroaryl group which may be partially hydrogenated and may be substituted, represented by R$^4$, are 1-3 groups each independently selected from the group consisting of a halogen atom, a cyano group, an alkyl group, a haloalkyl group, an alkoxyalkyl group, and an alkoxy group,
in the aryl group which may be substituted, represented by R$^4$, the aryl moiety is phenyl, or naphthyl,
in the 6- to 10-membered monocyclic or bicyclic heteroaryl group which may be partially hydrogenated and may be substituted, represented by R$^4$, the heteroaryl moiety is pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl;
a substituent of (i) the alkyl group which may be substituted, represented by R$^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group,
substituents of (ii) the cycloalkyl group which may be substituted, and (iii) the aliphatic heterocyclic group which may be substituted, represented by R$^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and alkoxycarbonyl group; an alkoxycarbonyl group; an amino group which may be substituted with 1-2 groups independently selected from the group consisting of an alkyl group and an alkanoyl group; and a heteroaryl group,
in the respective substituents of the above (i) to (iii), the aliphatic heterocyclic group is a group independently selected from the group consisting of piperidinyl, piperazinyl, morpholinyl, thiomorpholinyl, and tetrahydropyranyl,
in the respective substituents of the above (i) to (iii), the heteroaryl group is independently a pyrimidinyl group,
in the aliphatic heterocyclic group which may be substituted, represented by R$^2$, the heterocyclic moiety is pyrrolidinyl, piperidinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl,
R$^3$ is a hydrogen atom,
or a pharmaceutically acceptable salt thereof.
Furthermore, as another preferred embodiment, the present invention includes a compound of the above formula [I]:
wherein X and Y are any of the following (1)-(3),
(1) X is N, and Y is CH,
(2) X is CH, and Y is N, or
(3) X is CH, and Y is CH;
$R^1$ is a phenyl group which may be substituted with a halogen atom, or an indazolyl group which may be partially hydrogenated and may be substituted with an alkyl group,
$R^2$ is
(1) an alkyl group,
(2) a cyclohexyl group which may be substituted with an amino group which may be substituted with 1-2 alkyl groups, or a cyclohexyl group which may be substituted with an alkoxy group, or
(3) 8-azabicyclo[3.2.1]octyl which may be substituted with an alkyl group,
$R^3$ is a hydrogen atom,
or a pharmaceutically acceptable salt thereof.

Specific and non-limiting examples of the compounds which are included in the preferable embodiments of the present invention are those selected from the group consisting of:
3-[4-[(trans-4-methoxycyclohexyl)carbamoylmethyl]piperazin-1-yl]-5-(1-methyl-1H-indazol-6-yl)pyrazine;
3-[4-(isopropyl carbamoylmethyl)piperazin-1-yl]-5-(1-methyl-1H-indazol-6-yl)pyrazine;
5-(4-fluorophenyl)-3-[4-[[trans-4-(N,N-dimethylamino)cyclohexyl]carbamoylmethyl]piperazin-1-yl]pyridazine; and
3-(4-chlorophenyl)-5-[4-[(exo-8-methyl-8-azabicyclo[3.2.1]octan-3-yl)carbamoylmethyl]piperazin-1-yl]pyridine,
or a pharmaceutically acceptable salt thereof.

If a compound [I] of the present invention has chiral asymmetric carbon atom(s) in the molecule, there can be multiple stereoisomers based on the asymmetric atom(s) (i.e., diastereomers, or enantiomers). However, any one of the stereoisomers and any combination thereof are also included in the present invention.

A compound [I] of the present invention includes, for example, a radiolabeled compound (e.g., it is labeled with $^2H$, $^3H$, $^{13}C$, $^{14}C$, $^{15}N$, $^{18}F$, $^{32}P$, $^{35}S$, $^{125}I$, and the like) and a deuterium converter thereof.

A compound [I] of the present invention or a pharmaceutically acceptable salt thereof has an inhibitory effect against aldosterone synthetase, and therefore it is useful for preventing or treating various diseases and/or disease states evoked by an increased level of aldosterone and/or overproduction of aldosterone, or for improving prognosis of these diseases. These diseases includes, for example, primary aldosteronism (unilateral or bilateral adrenal adenomas, unilateral or bilateral adrenal hyperplasia, aldosterone-producing adrenal carcinoma, unilateral adrenal multiple nodules aldosteronism, glucocorticoid reactive aldosteronism, familial aldosteronism, or ectopic aldosterone-producing tumors, and the like), secondary aldosteronism (hypertension caused by an estrogen preparation, renal vascular hypertension, pregnancy hypertension, malignant hypertension, pheochromocytoma, congestive heart failure, pseudohypoaldosteronism, chronic liver disease associated with ascites (hepatic cirrhosis, and the like), inappropriate use of a medicament such as a laxative and a diuretic, or hyperaldosteronemia associated with nephrotic syndrome, Bartter's syndrome or Gitelman syndrome, and the like), hypertension (essential hypertension, secondary hypertension (renal vascular hypertension, renal parenchymal hypertension, primary aldosteronism, pheochromocytoma, sleep apnea syndrome, Cushing's syndrome, drug induced hypertension, aortostenosis, or hyperparathyroidism, and the like), treatment-resistant hypertension, mineralocorticoid-related hypertension, and the like), hart failure (congestive heart failure, left ventricular failure, right ventricular failure, systolic dysfunction, diastolic dysfunction, and the like), cardiomyopathy, cardiac hypertrophy (left ventricular hypertrophy, and the like), myocardial infarction, myocardial necrosis lesion, failure after myocardial ischemia, coronary artery disease, fibrosis or remodeling of myocardium or blood vessels (cardiovascular fibrosis and remodeling caused by hypertension and/or vascular endothelial function disorder, and the like), vascular restenosis, blood vessel wall thickening, arterial sclerosis, renal failure (chronic renal failure, and the like), acute renal disorder, chronic kidney disease, renal fibrosis, nephropathy (diabetic nephropathy, and the like), hypokalemia, obesity, metabolic syndrome, sleep apnea syndrome, retinopathy (diabetic retinopathy, and the like), hepatic disease, abnormal lipid metabolism, sympathetic hyperactivity, idiopathic and/or cyclic edema, headache, anxiety, depressive disorders, and the like.

In particular, a compound [I] of the present invention or a pharmaceutically acceptable salt thereof is useful for preventing or treating primary aldosteronism, secondary aldosteronism, hypertension, heart failure, arterial sclerosis, nephropathy, or retinopathy.

As described above, a compound [I] of the present invention or a pharmaceutically acceptable salt thereof has an excellent inhibitory activity against Cyp11B2, and as a result of studying the inhibitory activity against human Cyp11B2 according to an assay method described in Experimental example 1 below, each of the compounds of the compound [I] described in Examples of the present application has an $IC_{50}$ value of 100 nM or below. In addition, a compound [I] of the present invention includes a compound which exhibits high selectivity to CyP11B2.

For example, the $IC_{50}$ value (nM) of the compound described in Example 49 (that is, chemical name, 3-[4-isopropylcarbamoylmethyl) piperazin-1-yl]-5-(1-methyl-1H-indazol-6-yl)pyrazine) against human Cyp11B2 is 100 times higher than those against human Cyp11B1 that is an analogous enzyme because of high selectivity to human Cyp11B2.

A compound [I] of the present invention can be applied for a medical use as both a free form and a pharmaceutically acceptable salt thereof. The pharmaceutically acceptable salt includes, for example, an inorganic salt such as hydrochloride, sulfate, phosphate or hydrobromide, an organic salt such as acetate, fumarate, oxalate, citrate, methanesulfonate, benzenesulfonate, tosylate or maleate.

A compound [I] of the present invention or a pharmaceutically acceptable salt thereof includes any of an inner salt and an adduct thereof, as well as a solvate or a hydrate thereof.

A compound [I] of the present invention or a pharmaceutically acceptable salt thereof can be orally or parenterally administered alone, or as a pharmaceutical composition comprising the compound and a pharmaceutically acceptable carrier. The pharmaceutically acceptable carrier may be a conventional carrier in the art, and includes, for example, a diluent, a binder (syrup, gum arabic, gelatin, sorbitol, tragacanth, polyvinylpyrrolidone, and the like), an excipient (lactose, sucrose, corn starch, potassium phosphate, sorbit, glycine, and the like), a lubricant (magnesium stearate, talc, polyethylene glycol, silica, and the like), a disintegrant (potato starch), and a wetting agent (sodium lauryl sulfate, and the like).

A dosage form for such a pharmaceutical composition is not limited to a particular one, and includes a conventional medicinal formulation such as, for example, a tablet, a granule, a capsule, a powder, an injection, an inhalant, and a suppository.

A dosage of a compound [I] of the present invention or a pharmaceutically acceptable salt thereof varies depending on a mode of administration, age, body weight, condition of a patient, and the like. In the case of parenteral administration, the dosage is generally 0.001-10 mg/kg/day, and preferably 0.01-10 mg/kg/day. In the case of oral administration, the dosage is generally 0.01-100 mg/kg/day, and preferably 0.1-10 mg/kg/day.

A compound [I] of the present invention or a pharmaceutically acceptable salt thereof can be used alone, or in combination with one or more other medicaments depending on, for example, a disease to be treated. Such a medicament includes, for example, one or two or more medicaments selected from the group consisting of (1) an antihypertensive drug such as an angiotensin converting enzyme inhibitor, an angiotensin II receptor antagonist, a calcium antagonist, a β-blocker, an α/β-blockers; (2) a diuretic such as a thiazide diuretic and a loop diuretic; (3) a therapeutic agent for heart failure such as nitroglycerin and a digitalis preparation; (4) an anti-arrhythmic agent such as Na channel blocker; (5) an antilipemic agent such as an HMG-CoA reductase inhibitor; (6) an antithrombogenic agent such as a blood coagulation inhibitor and a thrombolytic agent; (7) a therapeutic agent for diabetes/diabetes complications such as insulin, an α-glucosidase inhibitor, an insulin resistance improving agent, an insulin secretion enhancer, and an aldose reductase inhibitor; (8) an anti-obesity agent; (9) a chemotherapeutic agent; and (10) an immunomodulatory agent such as an immunosuppressant and an immunoenhancer.

In the present specification, Me means a methyl group, Boc means a tert-butoxycarbonyl group, THF means tetrahydrofuran, and DMF means N,N-dimethylformamide.

A compound of the present invention or a pharmaceutically acceptable salt thereof can be produced, for example, as follows.

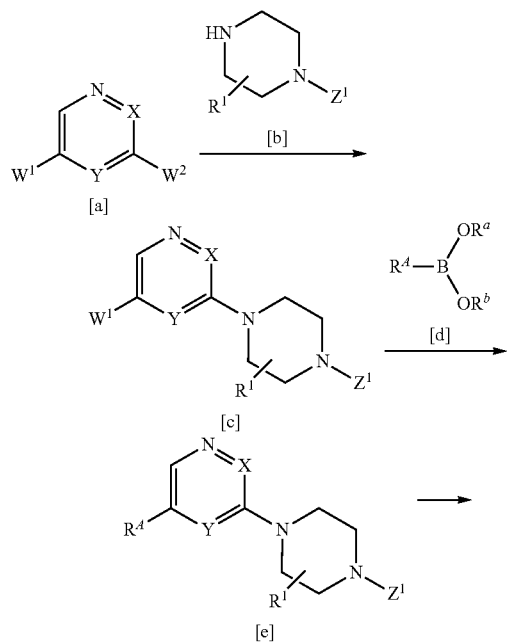

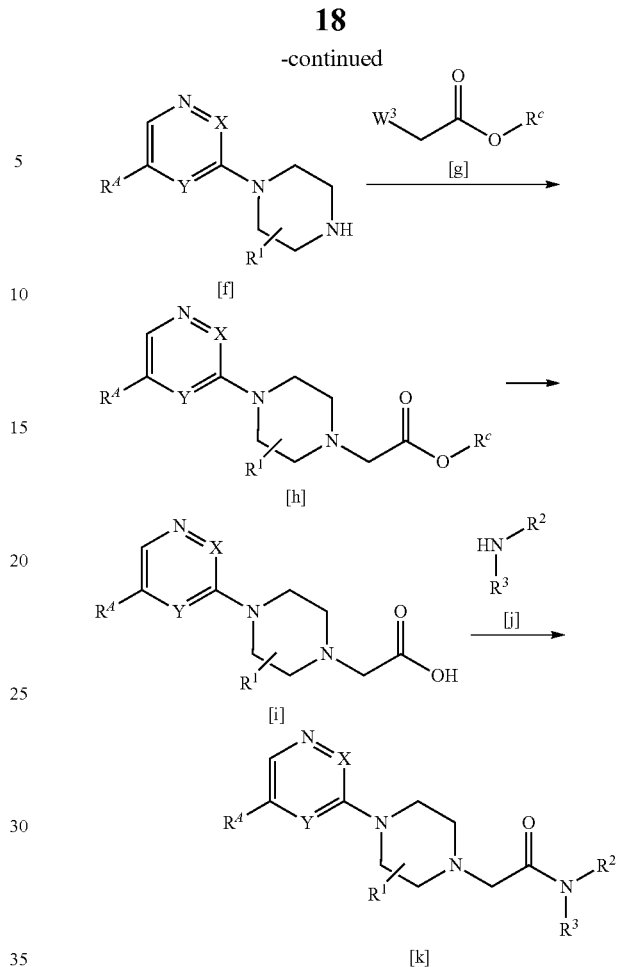

In the scheme, X and Y represent any of the following (1)-(3):

(1) X is N, and Y is CH or C—$R^Y$,
(2) X is CH, and Y is N, or
(3) X is CH, and Y is CH;

$R^Y$ represents an alkyl group;

$W^1$, $W^2$, and $W^3$ each represent a halogen atom, Ra, and $R^b$ each represent a hydrogen atom, or an alkyl group, $R^c$ represents an alkyl group. $Z^1$ represents a protective for an amino group (for example, an alkoxycarbonyl group such as a tert-butoxycarbonyl group). $R^A$ is a cycloalkyl group which may be substituted, a cycloalkenyl group which may be substituted, an aryl group which may be substituted, or a 6- to 10-membered monocyclic or bicyclic heteroaryl group which may be partially hydrogenated and may be substituted. $R^1$ represents a hydrogen atom, or an alkyl group, $R^2$ represents an alkyl group which may be substituted, a cycloalkyl group which may be substituted, an aliphatic heterocyclic group which may be substituted, or a heteroaryl group which may be partially hydrogenated and may be substituted, $R^3$ represents a hydrogen atom, or an alkyl group.

Among the objective compounds of the present invention, a compound represented by general formula [k] can be produced, for example, as follows.

First, a compound represented by general formula [c] is obtained by carrying out a nucleophilic substitution reaction or a coupling reaction between a compound [a] and a compound [b]. A compound represented by general formula [e] can be obtained by a coupling reaction between the compound [c] and a compound represented by general formula [d]. The resultant compound represented by general formula [e] is deprotected to obtain a compound represented by general formula [f]. A compound represented by general formula [h] can be obtained by a substitution reaction of the compound [f] with a compound represented by general formula [g]. The resultant compound represented by general formula [h] is hydrolyzed to obtain a compound represented by general formula [i]. The resultant compound [i] is reacted with a compound represented by general formula [j] or a salt thereof to give a product, and optionally, the resultant product is converted to a pharmaceutically acceptable salt thereof to give the desired compound [k] or a pharmaceutically acceptable salt thereof.

The nucleophilic substitution reaction between the compound [a] and the compound [b] or a salt thereof can be carried out in an appropriate solvent in the presence or absence of a base. As the salt of the compound [b], for example, salts of inorganic salts, such as hydrochloride and sulfate can be used. Any solvent may be used so long as it does not interfere with the present reaction. Examples thereof include amides such as N-methylpyrrolidone, ethers such as THF, acetonitrile, dimethyl sulfoxide, or a mixture thereof. In order to accelerate the reaction, the reaction is preferably carried out in the presence of a base. Examples of the base include diisopropylethylamine, triethylamine, diazabicycloundecene, sodium carbonate and the like. The amount used of the compound [b] or a salt thereof may be 1.0-10 equivalents, preferably 2.0-7.0 equivalents in a molar ratio to the compound [a]. This reaction can be carried out at room temperature –150° C., preferably at 60-100° C.

The coupling reaction between the compound [a] and the compound [b] can be carried out in an appropriate solvent in the presence of a palladium catalyst and a base in the presence or absence of a ligand according to a conventional method. The solvent, which does not interfere with the reaction, includes, for example, ethers such as THF, aromatic hydrocarbons such as toluene, amides such as DMF, water, or a mixture thereof and the like. The palladium catalyst includes, for example, tris(dibenzylideneacetone) dipalladium, bis(triphenylphosphine)palladium chloride, and the like. The base includes, for example, metal alkoxydes, such as sodium tert-butoxide, and bis(trimethylsilyl)sodium amide. The ligand includes, for example, 4,5-bis(diphenylphosphino)-9,9-dimethylxanthene, phosphines such as triphenylphosphine. The amount used of the compound [b] may be 1.0-3.0 equivalents, preferably 1.1-1.5 equivalents in a molar ratio to the compound [a]. The amount used of the palladium catalyst may be 0.01-0.1 equivalents, preferably 0.05 equivalents in a molar ratio to the compound [a]. The amount used of the base may be 2.0-6.0 equivalents, preferably 3.0-4.0 equivalents in a molar ratio to the compound [a]. The amount used of the ligand may be 0.02-0.2 equivalents, preferably 0.1 equivalents in a molar ratio to the compound [a]. This reaction can be carried out at room temperature –200° C., preferably at 80-150° C.

The coupling reaction between the compound [c] and the compound [d] can be carried out in an appropriate solvent in the presence of a palladium catalyst, a base and a ligand according to a conventional method. A solvent may be used so long as it does not interfere with the reaction. For example, it includes ethers such as THF, aromatic hydrocarbons such as toluene, amides such as DMF, water or a mixture thereof and the like. The palladium catalyst includes, for example, tris(dibenzylideneacetone)dipalladium, bis(triphenylphosphine)palladium dichloride, tetrakis (triphenylphosphine)palladium, and the like. The base includes, for example, alkali metal carbonates such as sodium carbonate, cesium carbonate, and potassium fluoride. The ligand includes, for example, tertiary phosphines such as tri(tert-butyl)phosphine, and triphenylphosphine. The amount used of the compound [d] may be 1.0-3.0 equivalents, preferably 1.1-1.5 equivalents in a molar ratio to the compound [c]. The amount used of the palladium catalyst may be 0.01-0.1 equivalents, preferably 0.05 equivalents in a molar ratio to the compound [c]. The amount used of the base may be 2.0-6.0 equivalents, preferably 3.0-4.0 equivalents in a molar ratio to the compound [c]. The amount used of the ligand may be 0.02-0.2 equivalents, preferably 0.1 equivalents in a molar ratio to the compound [c]. This reaction can be carried out at room temperature –200° C., preferably at 80-150° C.

A deprotection reaction of a compound [e] for obtaining the compound [f] can be carried out by removing a protecting group using a conventional method depending on the type of said protecting group $Z^1$. For example, when $Z^1$ is a tert-butoxycarbonyl group, said protecting group can be removed by treating the compound [e] with an acid in an appropriate solvent according to a conventional method. The solvent, which does not interfere with the reaction, includes, for example, esters such as ethyl acetate, halogenated aliphatic hydrocarbons such as chloroform, alcohols such as methanol, or a mixture thereof and the like. The acid includes, for example, hydrochloric acid, and trifluoroacetic acid.

The substitution reaction of the compound [f] with a compound [g] can be carried out in an appropriate solvent in the presence of a base according to a conventional method. The solvent, which does not interfere with the reaction, includes, for example, nitriles such as acetonitrile, halogenated aliphatic hydrocarbons such as chloroform, amides such as DMF, or a mixture thereof and the like. The base includes, for example, alkali metal carbonates such as sodium carbonate, organic amines such as triethylamine. The amount used of the compound [g] may be 1.0-3.0 equivalents, preferably 2.0 equivalents in a molar ratio to the compound [f]. The amount used of the base may be 1.0-3.0 equivalents, preferably 2.0 equivalents in a molar ratio to the compound [f]. This reaction can be carried out at room temperature –100° C., preferably at 50-60° C.

The hydrolysis reaction of a compound [h] for obtaining a compound [i] can be carried out in an appropriate solvent in the presence of a base and water according to a conventional method. The solvent, which does not interfere with the reaction, includes, for example, alcohols such as ethanol, and ethers such as THF, or a mixture thereof. The base includes, for example, alkali metal hydroxides such as sodium hydroxide. This reaction can be carried out at 0° C. to room temperature, preferably at room temperature. The amount used of the base may be 1.0-3.0 equivalents, preferably 2.0 equivalents in a molar ratio to the compound [h].

A condensation reaction between the compound [i] and a compound [j] or a salt thereof can be carried out, for example, in an appropriate solvent in the presence of a condensing agent and a base according to a conventional method. As a salt of the compound [j], salts with inorganic acids such as hydrochloride and sulfate can be used. The solvent, which does not interfere with the reaction, includes, for example, amides such as DMF, ethers such as THF, halogenated aliphatic hydrocarbons such as chloroform, and aromatic hydrocarbons such as toluene, acetonitrile, or a mixture thereof. The condensing agent includes, for example, O-(7-azabenzotriazol-1-yl)-N,N,N',N'-tetramethyluroniumhexafluorophosphate (HATU), 1-ethyl-3-(3-dimethylaminopropyl)carbodiimide hydrochloride and the like. The base includes, for example, amines such as diisopropylethylamine. The amount used of the condensing agent may be 1.0-5.0 equivalents, preferably 1.2-3.0 equivalents in a molar ratio to the compound [i]. The amount used of the base may be 0-10 equivalents, preferably 2.0-6.0 equivalents in a molar ratio to the compound [i]. This reaction can be carried out at 0-100° C., preferably at room temperature.

The substitution reaction between the compound [l] and the compound [m] can be carried out in a similar manner as described in the substitution reaction between the compound [f] and the compound [g].

A coupling reaction between the compound [n] and the compound [d] can be carried out in a similar manner as described in the coupling reaction between the compound [c] and the compound [d].

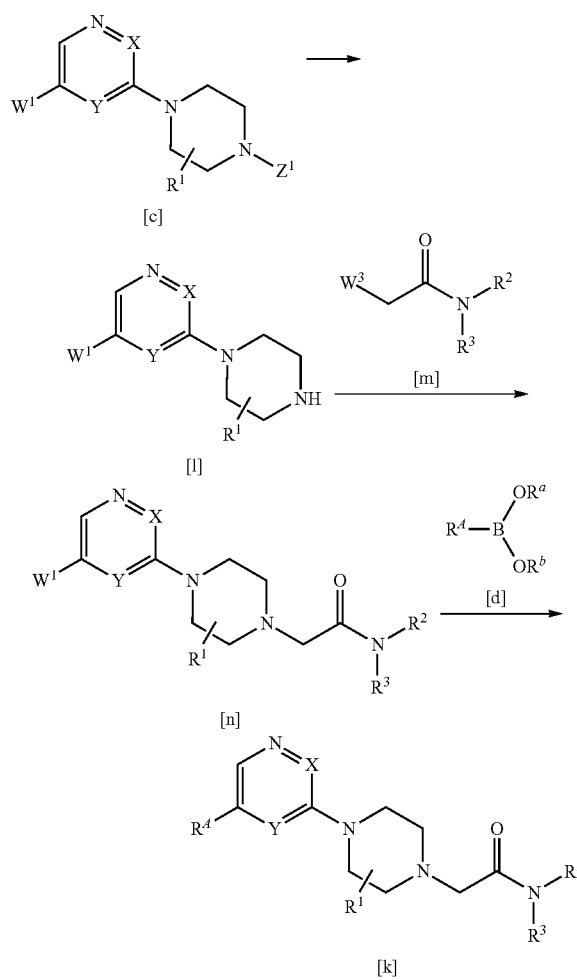

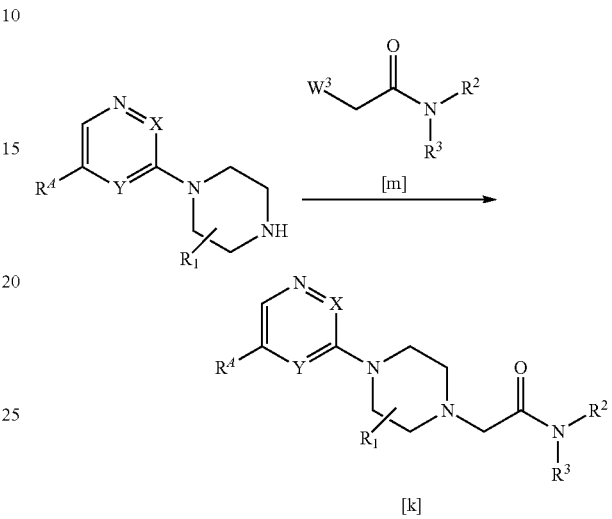

In the scheme, symbols are as defined above.

The conversion from the compound [f] to the compound [k] can also be carried out by the substitution reaction of the compound [f] with the compound [m] in a similar manner as described in the substitution reaction of the compound [l] with the compound [m].

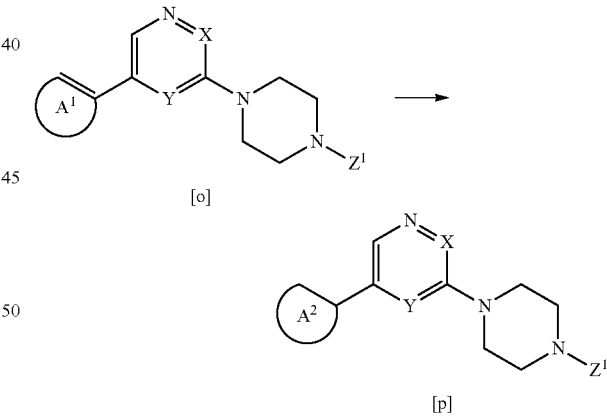

In the scheme, symbols are as defined above.

The conversion reaction from the compound [c] to the compound [k] can also be carried out, for example, as follows.

The compound represented by general formula [c] is deprotected to obtain a compound represented by general formula [l]. A compound represented by general formula [n] can be obtained by a substitution reaction of the compound [l] with a compound represented by general formula [m]. A coupling reaction between the resultant compound represented by general formula [n] and the compound represented by general formula [d], and optionally converting a product to a pharmaceutically acceptable salt thereof can produce the desired compound [k] or a pharmaceutically acceptable salt thereof.

The deprotection of the compound [c] can be carried out in a similar manner as described in the deprotection of the compound [e].

In the scheme, ring $A^1$ represents a cycloalkenyl group which may be substituted, ring $A^2$ represents a cycloalkyl group which may be substituted, and the other symbols are as defined above.

A compound [p] can be prepared by subjecting a compound of general formula [o] to catalytic reduction. The catalytic reduction reaction of the compound [o] can be carried out in an appropriate solvent in the presence of a base and a catalyst under hydrogen atmosphere according to a conventional method. The solvent, which does not interfere with the reaction, includes, for example, alcohols such as methanol, esters such as ethyl acetate, ethers such as THF, or a mixture thereof. The catalyst includes, for example, a palladium/carbon catalyst. The base includes, for example, amines such as triethylamine. The amount used of the catalyst may be 0.3-1.0, preferably 0.3 in a weight ratio to the compound [o]. The amount used of the base may be 3-10, preferably 5 in a volume/weight ratio to the compound [o]. This reaction can be carried out at 0° C. to room temperature, preferably at room temperature.

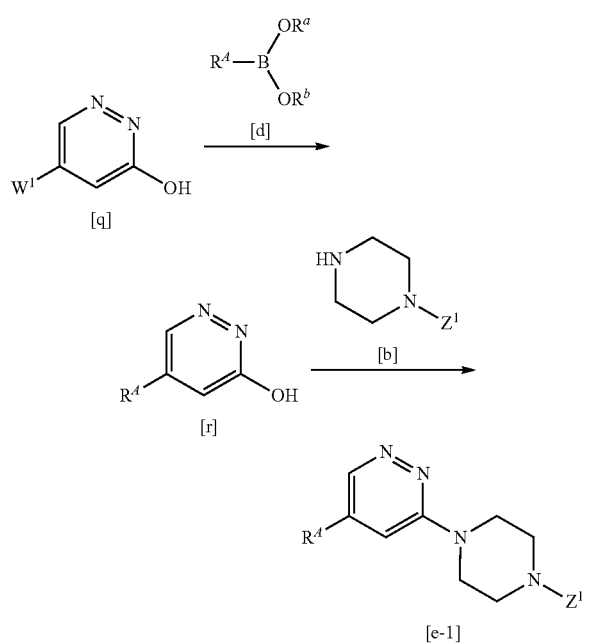

In the scheme, symbols are as defined above.

A compound [e-1] can also be produced, for example, as follows.

A compound represented by general formula [r] can be obtained by a coupling reaction between a compound represented by general formula [q] and the compound [d]. The compound represented by general formula [e-1] can be obtained by a substitution reaction of the resultant compound [r] with the compound [b].

A coupling reaction between the compound [q] and the compound [d] can be carried out in a similar manner as described in the coupling reaction between the compound [c] and the compound [d].

The substitution reaction of the compound [r] with the compound [b] can be carried out, for example, in an appropriate solvent in the presence of a condensing agent and a base according to a conventional method. The solvent, which does not interfere with the reaction, includes, for example, amides such as DMF, acetonitrile, or a mixture thereof and the like. The condensing agent includes, for example, 1H-benzotriazol-1-yloxytris(dimethylamino) phosphoniumhexafluorophosphate (BOP), and the like. The base includes, for example, amines such as diazabicycloundecene. The amount used of the condensing agent may be 1.0-3.0 equivalents, preferably 1.2-1.5 equivalents in a molar ratio to the compound [r]. The amount used of the base may be 1.0-5.0 equivalents, preferably 1.5-2.0 equivalents in a molar ratio to the compound [r]. This reaction can be carried out at room temperature –120° C., preferably at 60-100° C.

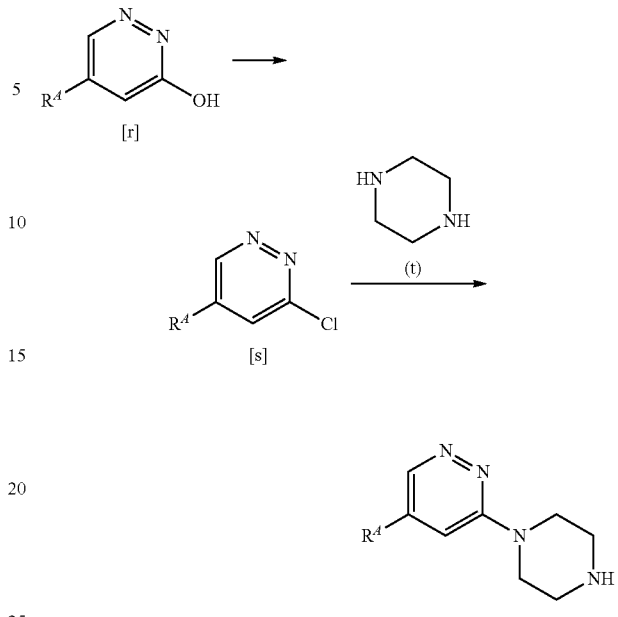

In the scheme, symbols are as defined above.

A compound [f-1] can also be produced, for example, as follows.

A compound represented by general formula [s] can be obtained by the chlorination reaction of the compound [r]. The compound represented by [f-1] can be obtained by the substitution reaction of the compound [s] with a compound [t].

The chlorination reaction of the compound [r] for obtaining the compound [s] can be carried out, for example, by reacting the compound [r] with a chlorine donner in an appropriate solvent. The solvent, which does not interfere with the reaction, includes, for example, ethers such as dioxane, aromatic hydrocarbons such as toluene, or a mixture thereof and the like. The chlorine donner includes, for example, thionyl chloride, phosphorus oxychloride, and the like. The amount used of the chlorine donner may be 2.0-20 equivalents, preferably 5.0-10 equivalents in a molar ratio to the compound [r]. This reaction can be carried out 60-150° C., preferably at 80-120° C.

The substitution reaction of the compound [s] with the compound [t] can be carried out in an appropriate solvent. The solvent, which does not interfere with the reaction, includes, for example, amides such as dimethylacetamide, acetonitrile, or a mixture thereof and the like. The amount used of the compound [t] may be 2.0-20 equivalents, preferably 5.0-10.0 equivalents in a molar ratio to the compound [s]. This reaction can be carried out at 80-150° C., preferably at 100-120° C.

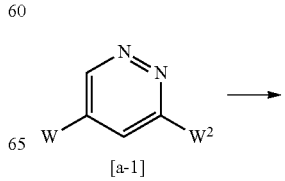

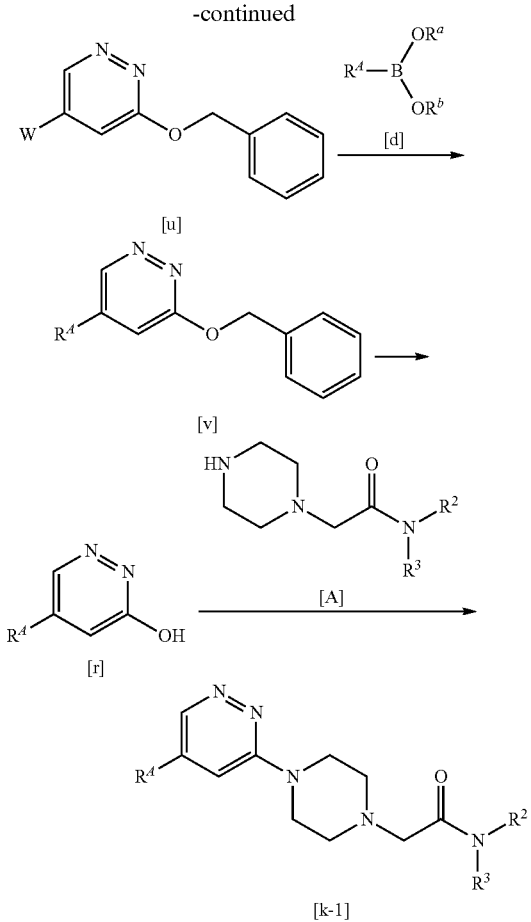

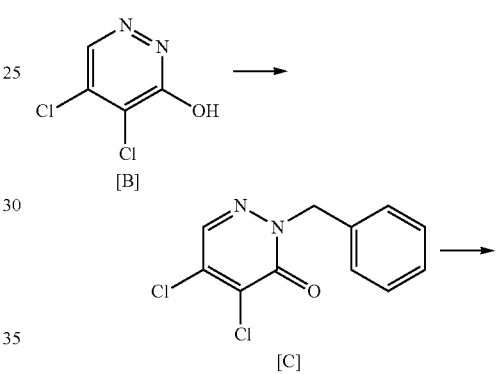

In the scheme, symbols are as defined above.

A compound [k-1] can also be produce as follows.

First, a compound represented by general formula [u] is obtained by carrying out a nucleophilic substitution reaction between a compound represented by general formula [a-1] and benzyl alcohol. A compound represented by general formula [v] can be obtained by a coupling reaction between the compound [u] and the compound represented by general formula [d]. The compound represented by general formula [v] is subjected to debenzylation to obtain the compound represented by general formula [r]. The resultant compound [r] is reacted with a compound represented by general formula [A] or a salt thereof to give a product, and optionally, the resultant product is converted to a pharmaceutically acceptable salt thereof to give the desired compound [k-1] or a pharmaceutically acceptable salt thereof.

The nucleophilic substitution reaction between the compound [a-1] and benzyl alcohol can be carried out, for example, in an appropriate solvent in the presence of a base. Any solvent may be used so long as it does not interfere with the present reaction. Examples thereof include amides such as DMF, ethers such as THF, or a mixture thereof. The base includes metal hydrides such as sodium hydride. The amount used of the benzyl alcohol may be 1.0-1.5 equivalents, preferably 1.0-1.2 equivalents in a molar ratio to the compound [a-1]. The base includes metal hydrides such as sodium hydride. The amount used of the base may be 2.0-4.0 equivalents, preferably 2.0-3.0 equivalents in a molar ratio to the compound [a-1]. This reaction can be carried out at 0° C.-room temperature, preferably at room temperature.

The coupling reaction between the compound [u] and the compound [d] can be carried out in a similar manner as described in the coupling reaction between the compound [c] and the compound [d].

A debenzylation reaction of a compound [v] can be carried out in an appropriate solvent in the presence of a catalyst under hydrogen atmosphere according to a conventional method. The solvent, which does not interfere with the reaction, includes, for example, alcohols such as methanol, esters such as ethyl acetate, ethers such as THF, or a mixture thereof and the like. The catalyst includes, for example, a palladium/carbon catalyst and the like. The amount used of the catalyst may be 0.1-1.0, preferably 0.3-0.5 in a weight ratio to the compound [v]. This reaction can be carried out at 0° C. to room temperature, preferably at room temperature.

A substitution reaction of the compound [r] with a compound [A] can be carried out in a similar manner as described in the reaction of the compound [r] with the compound [b]

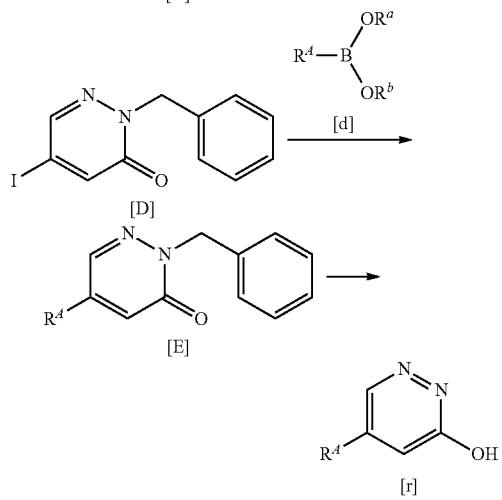

In the scheme, symbols are as defined above.

The compound [r] can also be produced, for example, as follows.

First, a compound represented by [B] is subjected to a substitution reaction with a benzyl halide to give a compound represented by [C]. A compound represented by [D] can be obtained by halogen substitution and reductive dehalogenation reactions. A coupling reaction between the resultant compound represented by [D] and the compound represented by general formula [d] gives a compound represented by general formula [E]. The resultant compound

[E] is subjected to a debenzylation reaction to give the compound represented by general formula [r].

The substitution reaction of the compound [B] with the benzyl halide can be carried out in an appropriate solvent in the presence of a base. The solvent, which does not interfere with the reaction, includes, for example, amides such as DMF, ethers such as THF, acetonitrile, or a mixture thereof. The base includes, for example, alkali metal carbonates such as sodium carbonate, amines such as diisopropylethylamine and the like. The amount used of the benzyl halide may be 1.0-2.0 equivalents, preferably 1.0-1.5 equivalents in a molar ratio to the compound [B]. The amount used of the base may be 2.0-4.0 equivalents, preferably 2.0-3.0 equivalents in a molar ratio to the compound [B]. This reaction can be carried out at room temperature −100° C., preferably at 60-100° C.

The halogen substitution and reductive dehalogenation reactions of the compound [C] can be carried out in hydriodic acid. This reaction can be carried out at 70-110° C., preferably at 80-100° C.

A coupling reaction between a compound [D] and the compound [d] can be carried out in a similar manner as described in the coupling reaction between the compound [c] and the compound [d].

A debenzylation reaction of a compound [E] can be carried out, for example, in an appropriate solvent in the presence of Lewis acid. The solvent, which does not interfere with the reaction, includes, for example, aromatic hydrocarbons such as toluene, ethers such as THF, or a mixture thereof. The Lewis acid includes a halogenated metal such as aluminum chloride. The amount used of the Lewis acid may be 1.0-5.0 equivalents, preferably 2.0-5.0 equivalents in a molar ratio to the compound [E]. This reaction can be carried out at 60-100° C., preferably at 80-100° C.

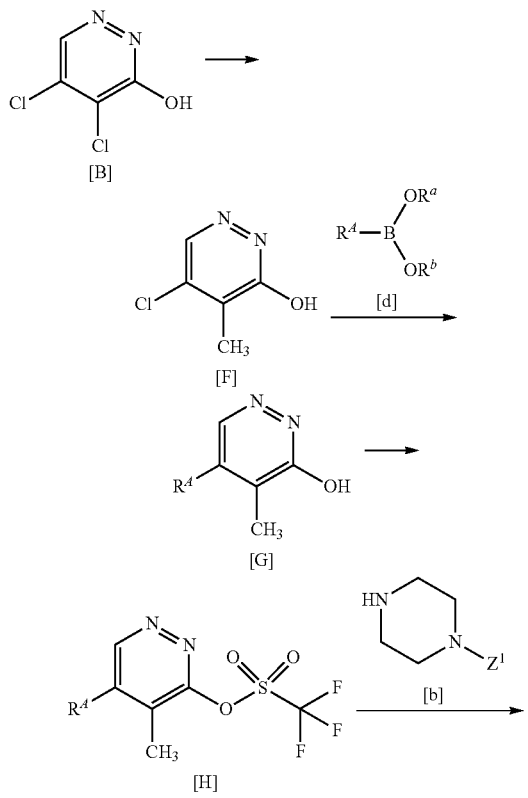

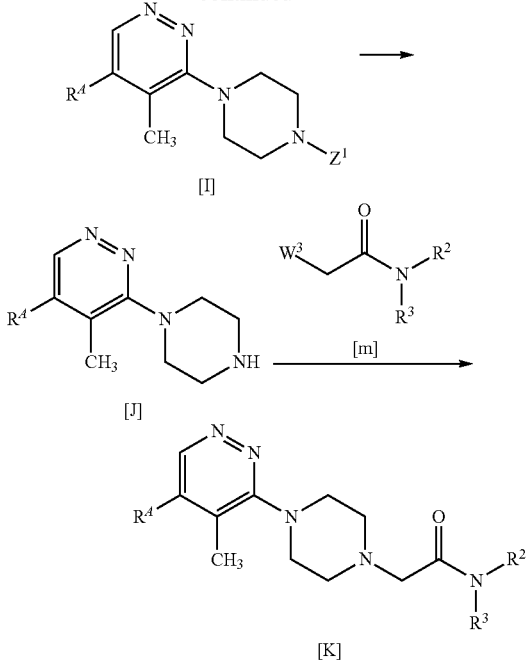

In the scheme, symbols are as defined above.

A compound [K] can be produced, for example, as follows.

First, a compound represented by [F] is obtained by carrying out a reaction of the compound represented by [B] with a methylating agent. By a coupling reaction between the resultant compound represented by [F] and the compound represented by general formula [d], a compound represented by [G] is obtained. The resultant compound [G] is trifluoromethanesulfonylated to give a compound represented by general formula [H]. A compound represented by general formula [I] is obtained by a nucleophilic substitution reaction of the compound represented by general formula [H] with the compound represented by [b]. The resultant compound represented by general formula [I] is deprotected to give a compound represented by general formula [J]. The resultant compound [J] is reacted with a compound represented by general formula [m] or a salt thereof to give a product, and optionally, the resultant product is converted to a pharmaceutically acceptable salt thereof to give the desired compound [K] or a pharmaceutically acceptable salt thereof.

A substitution reaction of the compound [B] with the methylating agent can be carried out, for example, in an appropriate solvent. The solvent, which does not interfere with the reaction, includes, for example, ethers such as THF. The methylating agent includes, for example, alkali metal compounds such as methyl magnesium bromide. The amount used of the methylating agent may be 1.0-4.0 equivalents, preferably 2.0-3.0 equivalents in a molar ratio to the compound [B]. This reaction can be carried out at room temperature −80° C., preferably at 50-70° C.

A coupling reaction between the compound [F] and the compound [d] can be carried out in a similar manner as described in the coupling reaction between the compound [c] and the compound [d].

A trifluoromethanesulfonylation reaction of the compound [G] can be carried out, for example, in an appropriate solvent in the presence of a base. The solvent, which does not interfere with the reaction, includes, for example, ethers such as THF, and halogenated aromatic hydrocarbons such as chloroform. The trifluoromethanesulfonylating agent includes, for example, trifluoromethanesulfonic anhydride, trifluoromethanesulfonyl chloride and the like. The base includes, for example, amines such as triethylamine, pyridine and the like. The amount used of the trifluoromethanesulfonylating agent may be 1.0-3.0 equivalents, preferably 1.0-2.0 equivalents in a molar ratio to the compound [G]. The amount used of the base may be 2.0-5.0 equivalents, preferably 2.0-4.0 equivalents in a molar ratio to the compound [G]. This reaction can be carried out at 0° C.-room temperature, preferably at 0° C.

A substitution reaction of the compound [H] with the compound [b] can be carried out in a similar manner as described in the substitution reaction of the compound [a] with the compound [b].

A deprotection reaction of a compound [I] can be carried out in a similar manner as described in the deprotection reaction of the compound [e].

Conversion from the compound [J] to the compound [K] can be carried out in a similar manner as described in the substitution reaction of the compound [I] with the compound [m].

EXAMPLES

Example 1

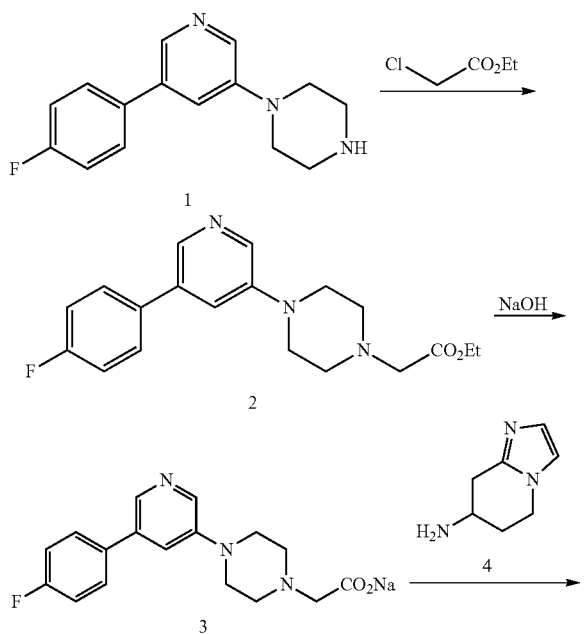

-continued

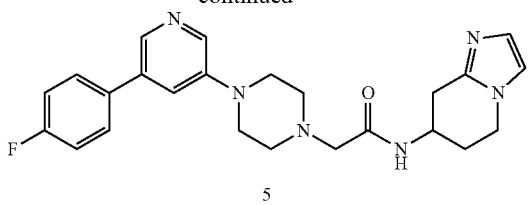

5

(1) The compound 1 (4.5 g) and sodium carbonate (3.7 g) were suspended in acetonitrile (88 mL), and ethyl chloroacetate (2.6 mL) was added thereto followed by stirring for 2 hours at 50° C. Ethyl chloroacetate (0.5 mL) was further added thereto followed by stirring for 3 days at room temperature. Water was added to the reaction mixture followed by extraction 3 times with chloroform. The organic layer was dried over anhydrous sodium sulfate. The solvent was distilled off under reduced pressure. The resultant residue was purified by silica gel column chromatography (eluent: chloroform-methanol; gradient: 100:0-20:1) to give the compound 2 (4.3 g) as a brown solid.

MS (APCI): 344 [M+H]$^+$ (2) The compound 2 (4.3 g) was suspended in ethanol (31 mL), and a 1 mol/L aqueous sodium hydroxide solution (12.4 mL) was added thereto, and the reaction mixture was stirred for 16 hours at room temperature. The precipitate produced in the reaction mixture was filtered, and washed with diethyl ether to give the compound 3 (1.1 g) as a colorless solid.

MS (ESI): 314[M+H]$^-$ (3) The compound 3 (34 mg) and the compound 4 (16 mg) were suspended in DMF (1 mL), and diisopropylethylamine (35 μL) and HATU (46 mg) were added thereto, followed by stirring at room temperature for 3 hours. To the reaction mixture were added water and a saturated aqueous solution of sodium hydrogen carbonate, followed by extraction three times with chloroform. The organic layer was washed with saturated brine, and then dried over anhydrous sodium sulfate. The solvent was distilled off under reduced pressure, and the resultant residue was purified by silica gel column chromatography (eluent: chloroform-methanol; gradient: 100:0-90:10) to give the compound 5 (18 mg) as a colorless solid.

MS (APCI): 435 [M+H]$^+$

Examples 2-10

The corresponding starting compound was treated in a similar manner as described in the above Example 1 to give the compounds of the following general formula wherein R$^1$ and R$^2$ each have a structure described in the following Table 1.

TABLE 1

| Example | R¹ | R² | MS |
|---|---|---|---|
| 2 | 4-Cl-phenyl | CH₂-(4-methylamino-pyrazol-1-yl), C(=O)NHCH₃ | 468/470 [M + H]⁺ APCI |
| 3 | 4-Cl-phenyl | 4-(4-methylamino-cyclohexyl)-4-hydroxypiperidinyl | 512/514 [M + H]⁺ APCI |
| 4 | 4-Cl-phenyl | 8-methyl-8-azabicyclo, 3-methylamino | 454/456 [M + H]⁺ APCI |
| 5 | 4-F-phenyl | N-Boc-oxa-azabicyclic, methylamino | 540 [M + H]⁺ APCI |
| 6 | 4-F-phenyl | 4-(dimethylamino)-cyclohexyl-methylamino | 440 [M + H]⁺ APCI |
| 7 | 2-methylphenyl | 1-methyl-4-(methylamino)pyrazolyl | 391 [M + H]⁺ APCI |
| 8 | 2-methylphenyl | (S)-3-methyl-2-(methylamino)butan-1-ol | 397 [M + H]⁺ APCI |
| 9 | 4-methylphenyl | 4-(methylamino)cyclohexyl-acetamide | 450 [M + H]⁺ APCI |

TABLE 1-continued

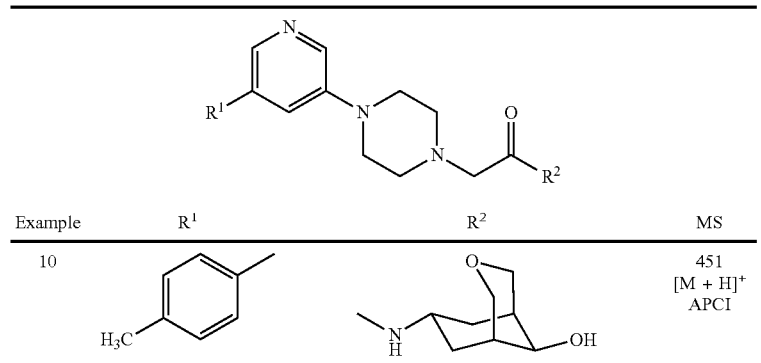

| Example | R¹ | R² | MS |
|---|---|---|---|
| 10 | H₃C—⟨phenyl⟩—CH₃ group structure | N-methyl bicyclic amino alcohol | 451 [M + H]⁺ APCI |

Example 11

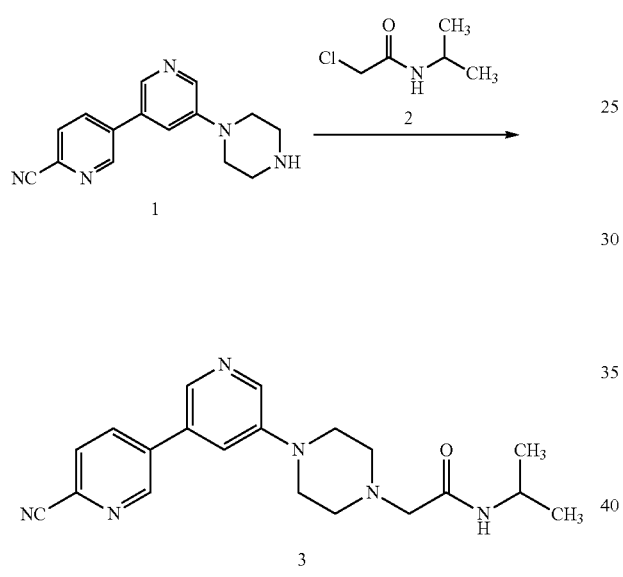

A mixed solution of the compound 1 (120 mg), the compound 2 (123 mg), and sodium carbonate (96 mg) in acetonitrile (5 mL) was stirred for 22 hours at 50° C. under argon atmosphere. The reaction mixture was cooled to room temperature, diluted with ethyl acetate, washed with water and saturated brine, and dried over Chem Elut (registered trademark). The solvent was distilled off under reduced pressure, and the resultant residue was purified by silica gel column chromatography (eluent: chloroform-ammonia water (10% methanol solution)=90:10). The resultant residue was triturated with a mixed solvent of hexane-ethyl acetate to give the compound 3 (95 mg) as a pale yellow solid.

MS (APCI) 365 [M+H]⁺

Example 12

The corresponding starting compound was treated in a similar manner as described in the above Example 11 to give the compound of the following general formula wherein R¹ has a structure described in the following Table 2.

TABLE 2

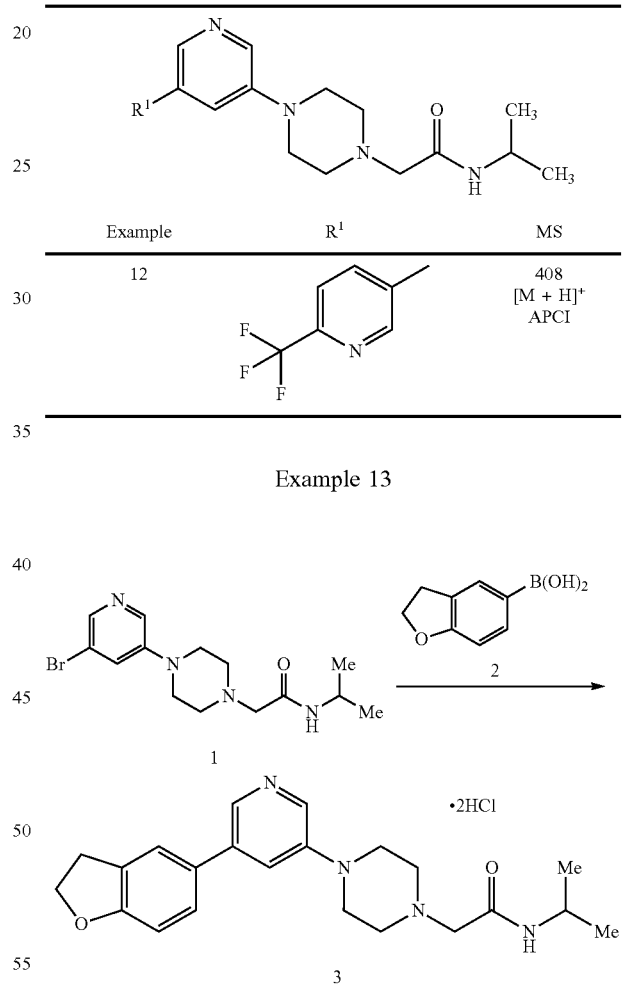

| Example | R¹ | MS |
|---|---|---|
| 12 | 5-methyl-2-(trifluoromethyl)pyridin-yl group | 408 [M + H]⁺ APCI |

Example 13

To a mixed solution of the compound 1 (171 mg), the compound 2 (164 mg), and dichlorobis(triphenylphosphine) palladium (18 mg) in dioxane (3 mL), a 2 mol/L aqueous solution of sodium carbonate (1 mL) was added thereto, and the reaction mixture was stirred for 15 minutes at 150° C. in a microwave reactor (Initiator, manufactured by Biotage Inc.) The reaction mixture was cooled to room temperature. To the reaction mixture was added a saturated aqueous solution of sodium hydrogen carbonate, and the reaction mixture was extracted twice with chloroform. The organic layer was washed with saturated brine, and then dried over anhydrous sodium sulfate. The solvent was distilled off under reduced pressure, and the resultant residue was purified by silica gel column chromatography (eluent: chloroform-methanol=100:5), and the resultant residue was converted to a dihydrochloride with hydrochloric acid (a 4 mol/L ethyl acetate solution) to give the compound 3 (200 mg) as a dark brown solid.

MS (APCI): 381 [M+H]$^+$

Examples 14-16

The corresponding starting compound was treated in a similar manner as described in the above Example 13 to give the compounds of the following general formula wherein each R$^1$ has a structure described in the following Table 3.

TABLE 3

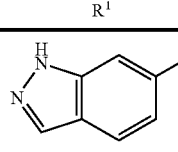

| Example | R$^1$ | MS | Salt |
|---|---|---|---|
| 14 | 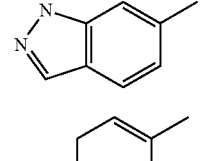 | 379 [M + H]$^+$ APCI | 2HCl |
| 15 | 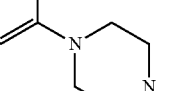 | 393 [M + H]$^+$ APCI | 2HCl |
| 16 | 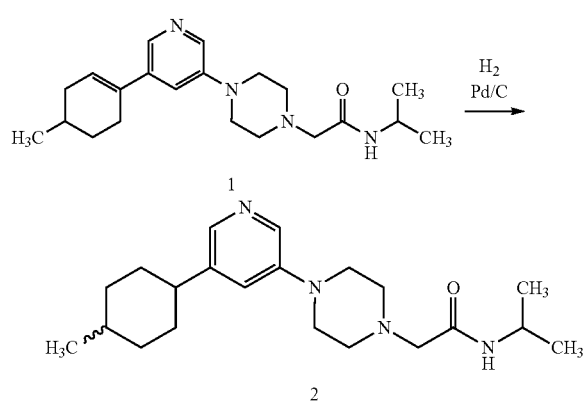 | 357 [M + H]$^+$ APCI | |

Example 17

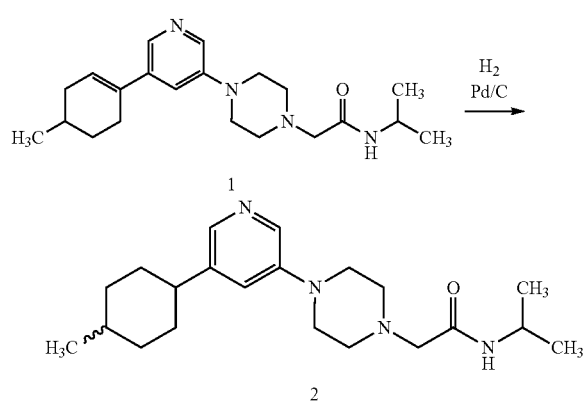

To a solution of the compound 1 (170 mg) and triethylamine (0.85 mL) in methanol (6.8 mL) was added 10% wet palladium on carbon (51 mg), and the reaction mixture was stirred for 2 hours at room temperature under hydrogen atmosphere. The reaction mixture was celite-filtered, and then the solvent was distilled off under reduced pressure. The resultant residue was purified by silica gel column chromatography (eluent: hexane-ethyl acetate; gradient: 100:0-85:15) to give the compound 2 (89.5 mg) as a pale brown viscous substance, which is a mixture of cis and trans forms (=3:2, main product is undetermined).

MS (APCI): 359 [M+H]$^+$

Example 18

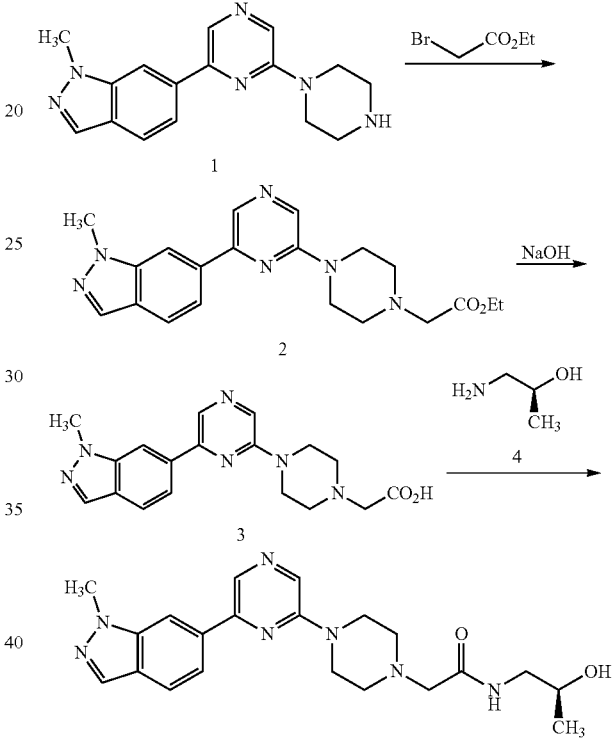

(1) The compound 1 (2.0 g) and sodium carbonate (1.4 g) were suspended in acetonitrile (34 mL), and ethyl bromoacetate (900 µL) was added thereto followed by stirring for 19 hours at room temperature. The reaction mixture was diluted with water, and then extracted 3 times with chloroform. The organic layer was dried over anhydrous sodium sulfate. The solvent was distilled off under reduced pressure. The resultant residue was purified by NH-silica gel column chromatography (eluent: hexane-ethyl acetate; gradient: 70:30-0:100). The resultant residue was crystallized with diethyl ether to give the compound 2 (1.9 g) as a pale yellow solid.

MS (APCI): 381 [M+H]$^-$ (2) The compound 2 (1.9 g) was suspended in ethanol (10 mL), and a 2 mol/L aqueous sodium hydroxide solution (5 mL) was added thereto, and the reaction mixture was stirred for 1 day at room temperature. The reaction mixture was concentrated under reduced pressure, and the residue was dissolved in water. A 2 mol/L aqueous hydrochloric acid solution was added thereto under ice cooling to adjust the pH to 5. The precipitate was filtered, washed with water and dried under reduced pressure to give the compound 3 (1.7 g) as a pale yellow solid.

MS (APCI) 353 [M+H]⁻

(3) The compound 3 (150 mg) and the compound 4 (96 mg) were suspended in DMF (2 mL), and diisopropylethylamine (224 μL) and HATU (486 mg) were added thereto, followed by stirring for 4 days at room temperature.

The reaction mixture was diluted with water, and extracted three times with chloroform. The organic layer was dried over anhydrous sodium sulfate. The solvent was distilled off under reduced pressure, and the resultant residue was purified by silica gel column chromatography (eluent: chloroform-methanol; gradient: 100:0-95:5) to give the compound 5 (114 mg) as a pale yellow solid.

MS (APCI): 410 [M+H]⁺

Examples 19-46

The corresponding starting compound was treated in a similar manner as described in the above Example 18 to give the compounds of the following general formula wherein $R^1$ and $R^2$ each have a structure described in the following Table 4.

TABLE 4

| Example | $R^1$ | $R^2$ | MS |
|---|---|---|---|
| 19 | 4-methylphenyl (H₃C-C₆H₄-) | piperazinyl-CH₂-C(O)-NH-pyrazole-N-CH₂-C(O)-N(CH₃)₂ with N-methylpiperazine | 463 [M + H]⁺ APCI |
| 20 | 4-methylphenyl | N-methylpiperazine-CH₂-C(O)-NH-cyclohexyl-OCH₃ | 424 [M + H]⁺ APCI |
| 21 | 4-methylphenyl | N-methylpiperazine-CH₂-C(O)-NH-CH₂-(4-OH-1-methylpiperidine) | 439 [M + H]⁺ APCI |
| 22 | 1-methyl-6-yl-indazole | N-methylpiperazine-CH₂-C(O)-NH-cyclohexyl-CH₂OH | 464 [M + H]⁺ APCI |
| 23 | 1-methyl-6-yl-indazole | N-methylpiperazine-CH₂-C(O)-NH-CH(CH₃)-CF₃ | 448 [M + H]⁺ APCI |
| 24 | 1-methyl-6-yl-indazole | N-methylpiperazine-CH₂-C(O)-NH-CH₂-CH(OH)CH₃ | 410 [M + H]⁺ APCI |

TABLE 4-continued
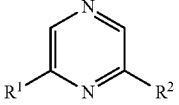
| Example | R¹ | R² | MS |
|---|---|---|---|
| 25 | 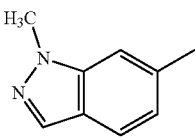 | 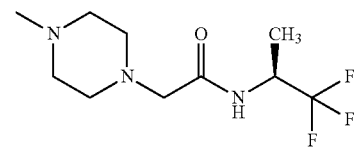 | 448 [M + H]⁺ APCI |
| 26 | 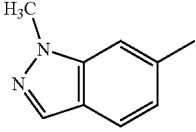 | 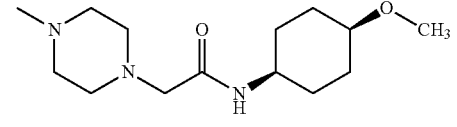 | 464 [M + H]⁺ APCI |
| 27 | 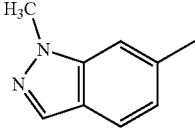 | 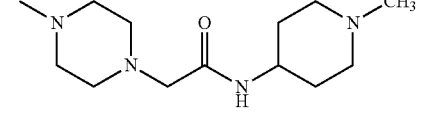 | 449 [M + H]⁺ APCI |
| 28 | 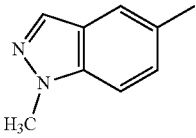 | 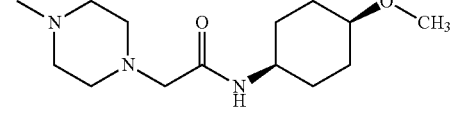 | 464 [M + H]⁺ APCI |
| 29 | 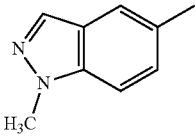 | 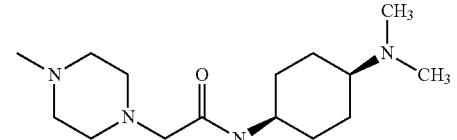 | 477 [M + H]⁺ APCI |
| 30 | 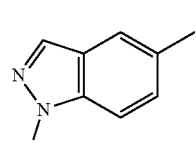 | 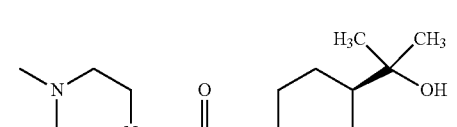 | 492 [M + H]⁺ APCI |
| 31 | 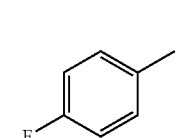 | 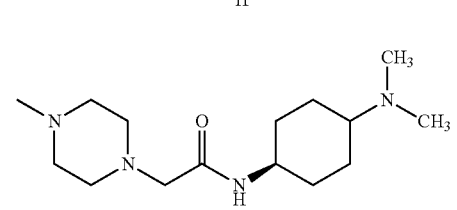 | 441 [M + H]⁺ APCI |
| 32 | 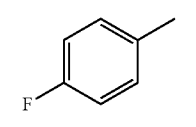 | 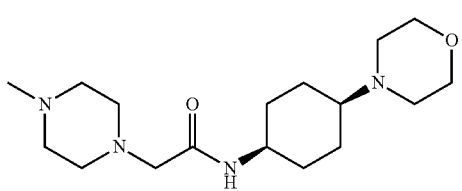 | 483 [M + H]⁺ APCI |

TABLE 4-continued
| Example | R¹ | R² | MS |
|---|---|---|---|
| 33 | 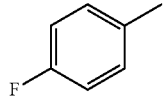 | 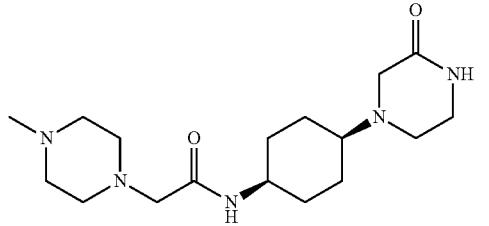 | 496 [M + H]⁺ APCI |
| 34 | 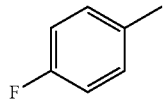 | 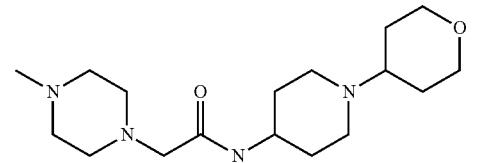 | 483 [M + H]⁺ APCI |
| 35 | 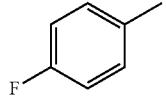 | 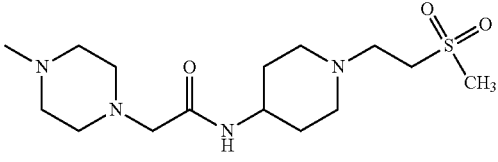 | 505 [M + H]⁺ APCI |
| 36 | 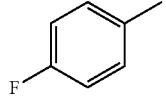 | 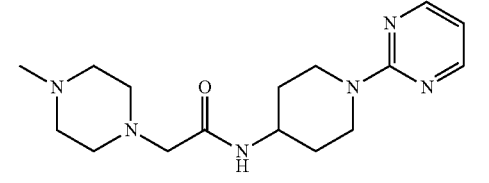 | 477 [M + H]⁺ APCI |
| 37 | 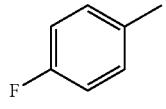 | 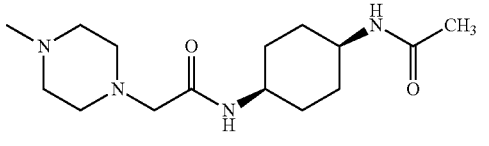 | 455 [M + H]⁺ APCI |
| 38 | 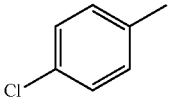 | 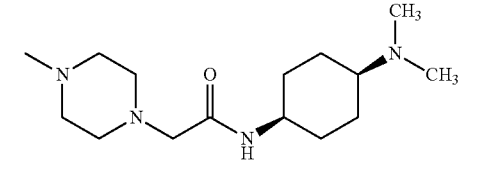 | 457/459 [M + H]⁺ APCI |
| 39 | 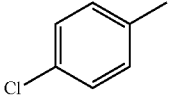 | 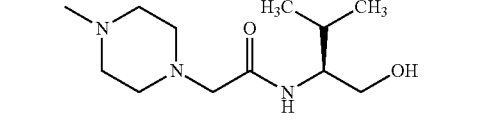 | 418/420 [M + H]⁺ APCI |
| 40 | 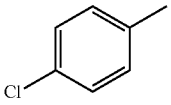 | 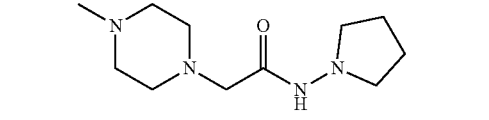 | 401/403 [M + H]⁺ APCI |

TABLE 4-continued

| Example | R¹ | R² | MS |
|---|---|---|---|
| 41 | 4-chlorophenyl | N-methylpiperazinyl-CH₂-C(O)NH-(1,1-dioxo-tetrahydrothiopyran-4-yl) | 464/466 [M + H]⁺ APCI |
| 42 | 4-trifluoromethylphenyl | (2S)-2-methyl-4-methylpiperazinyl-CH₂-C(O)NH-CH(CH(CH₃)₂)CH₂OH | 466 [M + H]⁺ APCI |
| 43 | 4-trifluoromethylphenyl | (2S)-2-methyl-4-methylpiperazinyl-CH₂-C(O)NH-(4-hydroxy-4-methylcyclohexyl) | 492 [M + H]⁺ APCI |
| 44 | 4-trifluoromethylphenyl | (2S)-2-methyl-4-methylpiperazinyl-CH₂-C(O)NH-CH(CH₃)C(CH₃)₂OH | 466 [M + H]⁺ APCI |
| 45 | 4-trifluoromethylphenyl | (2S)-2-methyl-4-methylpiperazinyl-CH₂-C(O)NH-CH₂C(CH₃)₂OH | 452 [M + H]⁺ APCI |
| 46 | 4-trifluoromethylphenyl | (2S)-2-methyl-4-methylpiperazinyl-CH₂-C(O)NH-(2-hydroxycyclopentyl) | 464 [M + H]⁺ APCI |

Example 47

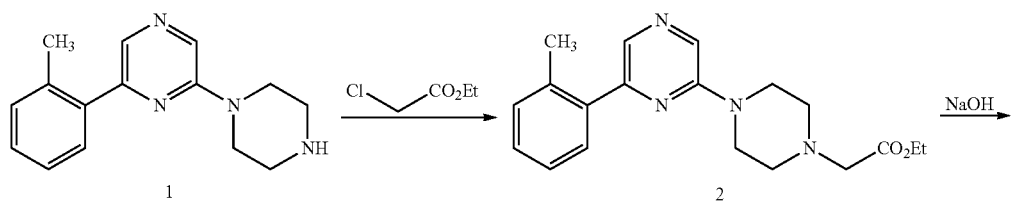

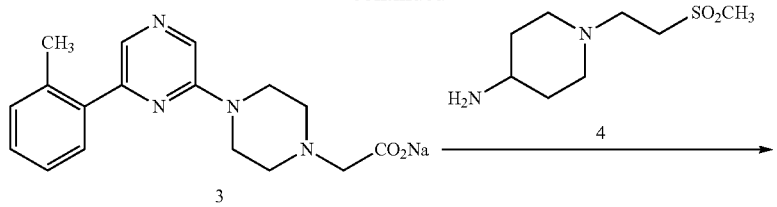

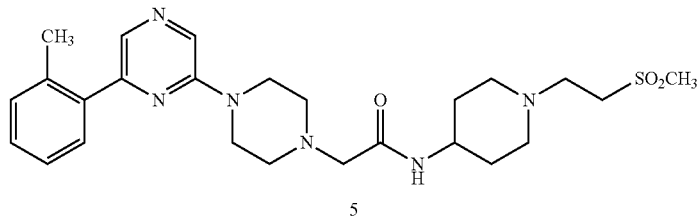

(1) The compound 1 (5.1 g) and sodium carbonate (4.3 g) were suspended in acetonitrile (200 mL), and ethyl chloroacetate (2.6 mL) was added thereto followed by stirring overnight at 65° C. The reaction mixture was cooled to room temperature, diluted with water and ethyl acetate, and then extracted with ethyl acetate. The organic layer was washed with water and saturated brine, and dried over anhydrous sodium sulfate. The solvent was distilled off under reduced pressure, and the resultant residue was purified by silica gel column chromatography (eluent: hexane-ethyl acetate=75:25) to give the compound 2 (5.5 g) as a pale yellow viscous substance.

MS (APCI): 341 [M+H]$^+$ (2) The compound 2 (4.6 g) was suspended in ethanol (13 mL), and a 2 mol/L aqueous sodium hydroxide solution (16 mL) was added thereto, and the reaction mixture was stirred for 6 hours at room temperature. The reaction mixture was concentrated under reduced pressure to give a yellow amorphous substance. Diisopropyl ether was added thereto, and the resultant precipitate was filtered and dried under reduced pressure to give the compound 3 (4.5 g) as a pale yellow solid.

MS (ESI): 311 [M+H]$^+$ (3) The compound 3 (33 mg) and the compound 4 (25 mg) were suspended in DMF (2 mL), and diisopropylethylamine (35 μL) and HATU (46 mg) were added thereto, followed by stirring for 4 days at room temperature. The reaction mixture was diluted with water, and extracted three times with chloroform. The organic layer was dried over anhydrous sodium sulfate. The solvent was distilled off under reduced pressure, and the resultant residue was purified by silica gel column chromatography (eluent: chloroform-methanol; gradient: 100:0-95:5) to give the compound 5 (38 mg) as a colorless solid.

MS (APCI): 501 [M+H]$^+$

Example 48

The corresponding starting compound was treated in a similar manner as described in the above Example 47 to give the compound of the following general formula wherein $R^1$ and $R^2$ each have a structure described in the following Table 5.

TABLE 5

| Example | $R^1$ | $R^2$ | MS |
|---|---|---|---|
| 48 | (2-methylphenyl) | (4-methylpiperazin-1-yl)acetamido-quinuclidinyl | 421 [M + H]$^+$ APCI |

Example 49

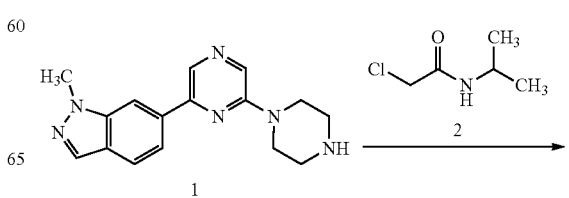

-continued

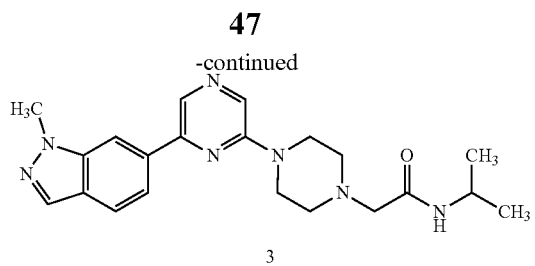

3

A mixed solution of the compound 1 (120 mg), the compound 2 (83 mg), and sodium carbonate (65 mg) in acetonitrile (2 mL) was stirred for 16 hours at 60° C. The reaction mixture was cooled to room temperature, diluted with water, and extracted with chloroform. The organic layer was dried over anhydrous sodium sulfate, and then the solvent was distilled off under reduced pressure. The resultant residue was purified by NH-silica gel column chromatography (eluent: hexane-ethyl acetate; gradient: 50:50-0:100) to give the compound 3 (150 mg) as a pale pink solid.
MS (APCI) 394 [M+H]$^+$ Examples 50-52

The corresponding starting compound was treated in a similar manner as described in the above Example 49 to give the compounds of the following general formula, wherein R$^1$ and R$^2$ each have a structure described in the following Table 6.

Example 53

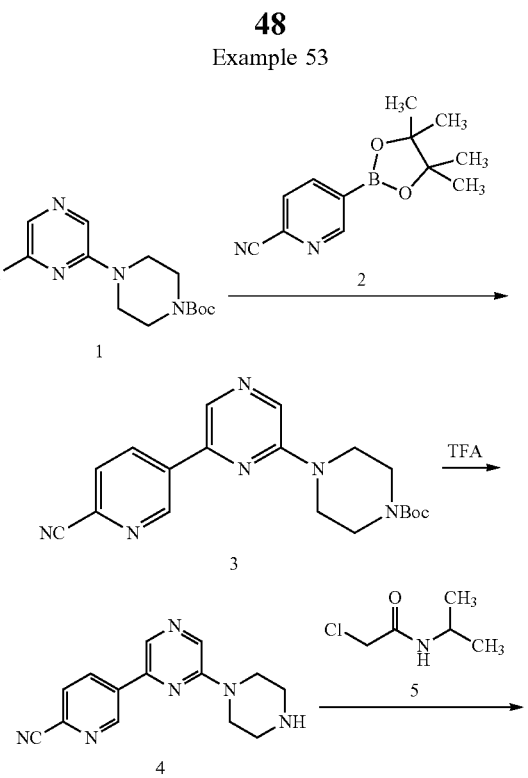

TABLE 6

| Example | R$^1$ | R$^2$ | MS |
|---|---|---|---|
| 50 | 1-methyl-1H-indazol-5-yl | N-isopropyl-2-(piperazin-1-yl)acetamide | 394 [M + H]$^+$ APCI |
| 51 | 4-(trifluoromethyl)phenyl | (S)-N-isopropyl-2-(2-methylpiperazin-1-yl)acetamide | 422 [M + H]$^+$ ESI |
| 52 | 4-methylcyclohexyl (Mixture of cis and trans (3:2, main component is undetermined)) | N-isopropyl-2-(piperazin-1-yl)acetamide | 360 [M + H]$^+$ APCI |

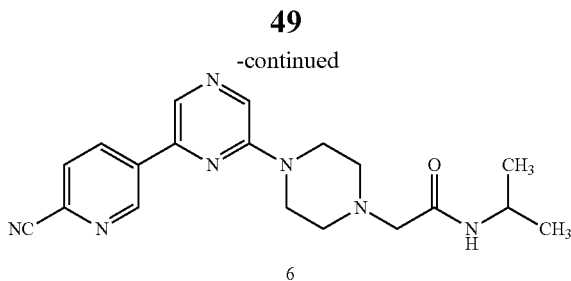

(1) A mixed solution of the compound 1 (299 mg), the compound 2 (253 mg), tris(dibenzylideneacetone)dipalladium (46 mg), tri-t-butylphosphine (1 mol/L toluene solution, 100 μL), and cesium carbonate (1.3 g) in THF (15 mL) was degassed under reduced pressure, and then back-filled with argon. The reaction mixture was stirred for 17.5 hours with heating to reflux. The reaction mixture was cooled to room temperature, diluted with ethyl acetate-water, and then celite-filtered. The filtrate was washed with water and saturated brine, and then dried over anhydrous magnesium sulfate. The solvent was distilled off under reduced pressure, and the resultant residue was purified by silica gel column chromatography (eluent: chloroform-methanol=95:5). The resultant crystalline residue was suspended and washed in ethyl acetate-hexane (about 1:2), taken by filtration, and dried to give the compound 3 (232 mg) as a yellow solid.

MS (APCI): 367 [M+H]$^+$ (2) To a solution of the compound 3 (151 mg) and thioanisole (510 mg) in dichloromethane (2 mL) was added trifluoroacetic acid (1 mL), and the reaction mixture was stirred for 1 hour at room temperature. The reaction mixture was diluted with methanol, treated with packed strong cation exchange resin (PoraPak Rxn Cx, eluent: ammonia (1 mol/L methanol solution), and the eluate was concentrated under reduced pressure to give a crude product of the compound 4.

MS (APCI) 267 [M+H]$^+$ (3) A mixed solution of the compound 4 (150 mg), the compound 5 (11 mg), and sodium carbonate (87 mg) in acetonitrile (5 mL) was stirred for 18 hours at 50° C. under argon atmosphere. The reaction mixture was cooled to room temperature, diluted with ethyl acetate, washed with water, and dried over Chem Elut (registered trademark). The solvent was distilled off under reduced pressure, and the resultant residue was purified by silica gel column chromatography (eluent: chloroform-methanol; gradient: 100:0-95:5). The resultant residue was suspended and washed in ethyl acetate to give the compound 6 (77 mg) as a yellow solid.

MS (APCI) 366 [M+H]$^+$

Example 54

The corresponding starting compound was treated in a similar manner as described in the above Example 53 to give the compound of the following general formula wherein R$^1$ and R$^2$ each have a structure described in the following Table 7.

TABLE 7

| Example | R$^1$ | R$^2$ | MS |
|---|---|---|---|
| 54 | H$_3$C-(1-methylindazol-6-yl) | 4-methylpiperazinyl-CH$_2$-C(O)-NH-pyrrolidinyl | 421 [M + H]$^+$ APCI |

Example 55

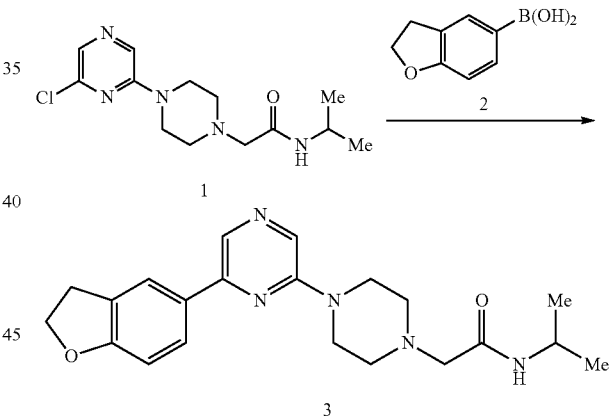

To a mixed solution of the compound 1 (149 mg), the compound 2 (164 mg), and dichlorobis(triphenylphosphine) palladium (18 mg) in dioxane (3 mL) was added a 2 mol/L aqueous solution of sodium carbonate (1 mL). The reaction mixture was stirred for 15 minutes at 150° C. in a microwave reactor (Initiator, manufactured by Biotage Inc.) The reaction mixture was cooled to room temperature, and a saturated aqueous solution of sodium hydrogen carbonate was added thereto. Then, the reaction mixture was extracted twice with chloroform. The organic layer was washed with saturated brine, and dried over anhydrous sodium sulfate. The solvent was distilled off under reduced pressure, and the resultant residue was purified by silica gel column chromatography (eluent: chloroform-methanol; gradient: 100:0-95:5). The resultant crystalline residue was recrystallized with ethyl acetate to give the compound 3 (128 mg) as a dark brownish red solid.

MS (APCI) 382 [M+H]$^+$

Example 56

The corresponding starting compound was treated in a similar manner as described in the above Example 55 to give the compound of the following general formula wherein $R^1$ and $R^2$ each have a structure described in the following Table 8.

TABLE 8

| Example | $R^1$ | $R^2$ | MS |
|---|---|---|---|
| 56 | 6-methyl-1H-indazol-yl | 4-methylpiperazinyl-CH2-C(O)-NH-CH(CH3)2 | 380 [M + H]+ APCI |

Example 57

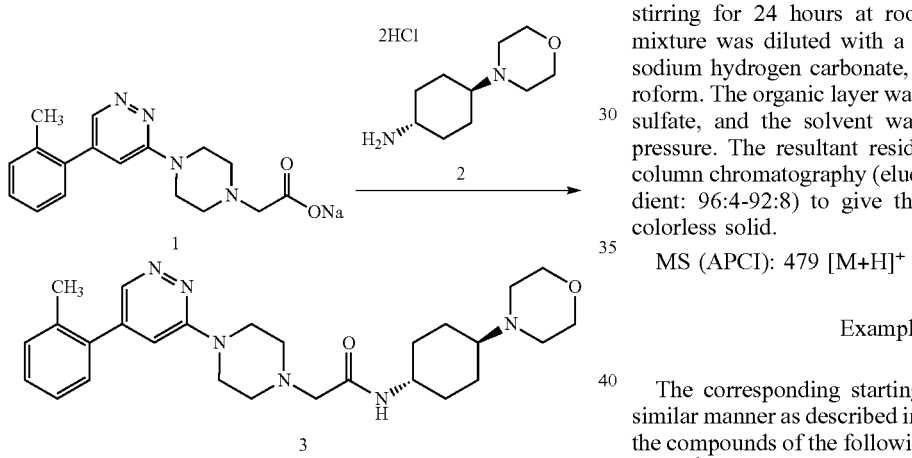

The compound 1 (33 mg) and the compound 2 (31 mg) were suspended in DMF (1 mL), and diisopropylethylamine (60 µL) and HATU (46 mg) were added thereto, followed by stirring for 24 hours at room temperature. The reaction mixture was diluted with a saturated aqueous solution of sodium hydrogen carbonate, and then extracted with chloroform. The organic layer was dried over anhydrous sodium sulfate, and the solvent was distilled off under reduced pressure. The resultant residue was purified by silica gel column chromatography (eluent: chloroform-methanol; gradient: 96:4-92:8) to give the compound 3 (70 mg) as a colorless solid.

MS (APCI): 479 [M+H]+

Examples 58-80

The corresponding starting compound was treated in a similar manner as described in the above Example 57 to give the compounds of the following general formula wherein $R^1$ and $R^2$ each have a structure described in the following Table 9.

TABLE 9

| Example | $R^1$ | $R^2$ | MS |
|---|---|---|---|
| 58 | 4-methylphenyl | 3-hydroxy-4-(methylamino)tetrahydropyran-4-yl | 412 [M + H]+ APCI |
| 59 | 4-methylphenyl | 1-[4-(methylamino)piperidin-1-yl]-CH2-C(O)-NH-CH3 | 466 [M + H]+ APCI |

TABLE 9-continued

| Example | R¹ | R² | MS |
|---|---|---|---|
| 60 | 2,5-dimethylphenyl | (2S)-N-methyl-(4-methylmorpholin-2-yl)methylamine | 425 [M + H]⁺ APCI |
| 61 | 2-methylphenyl | N-methyl-pyridin-3-ylamine | 389 [M + H]⁺ APCI |
| 62 | 4-fluorophenyl | N-methyl-(1-methylsulfonylpiperidin-4-yl)methylamine | 491 [M + H]⁺ APCI |
| 63 | 4-fluorophenyl | (2S)-1-methylamino-propan-2-ol | 374 [M + H]⁺ APCI |
| 64 | 4-fluorophenyl | tert-butyl 4-(2-methylaminoethyl)piperazine-1-carboxylate | 528 [M + H]⁺ APCI |
| 65 | 4-chlorophenyl | N-methyl-(4-methoxypiperidin-1-yl)amine | 445/447 [M + H]⁺ APCI |
| 66 | 4-fluorophenyl | 2-(4-methylaminocyclohexyloxy)-N-methylacetamide | 485 [M + H]⁺ APCI |
| 67 | 2,6-difluorophenyl | N,N-dimethyl-N'-methyl-cyclohexane-1,4-diamine | 459 [M + H]⁺ APCI |
| 68 | 4-chlorophenyl | 2-(4-methylaminocyclohexyloxy)-N-methylacetamide | 501/503 [M + H]⁺ APCI |

TABLE 9-continued
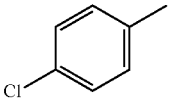
| Example | R¹ | R² | MS |
|---|---|---|---|
| 69 | 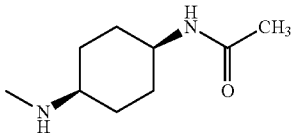 | 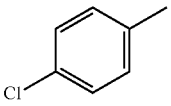 | 471/473 [M + H]⁺ APCI |
| 70 | 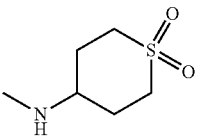 | 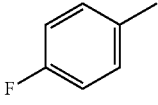 | 464/466 [M + H]⁺ APCI |
| 71 | 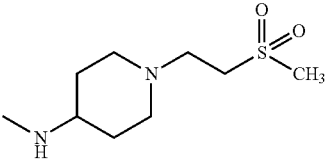 | 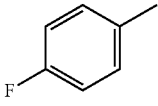 | 505 [M + H]⁺ APCI |
| 72 | 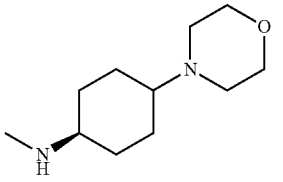 | 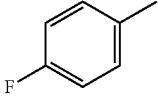 | 483 [M + H]⁺ APCI |
| 73 | 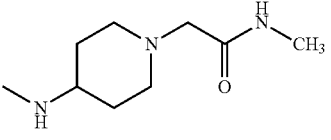 | 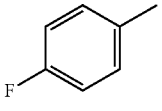 | 470 [M + H]⁺ APCI |
| 74 | 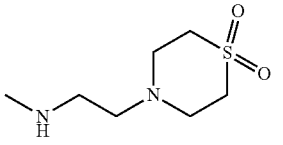 | 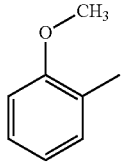 | 477 [M + H]⁺ APCI |
| 75 | 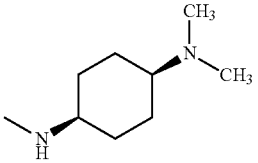 | 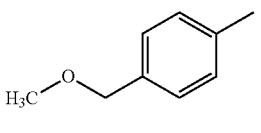 | 453 [M + H]⁺ APCI |
| 76 | 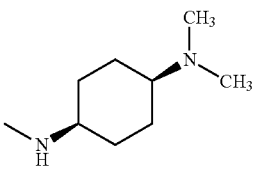 | | 467 [M + H]⁺ APCI |

TABLE 9-continued

| Example | R¹ | R² | MS |
|---|---|---|---|
| 77 | 2-methylphenyl | 4-(dimethylamino)cyclohexyl-N(H)(CH₃)- | 437 [M + H]⁺ APCI |
| 78 | 4-fluorophenyl | 1-(2-hydroxyethyl)piperidin-4-yl-N(H)(CH₃)- | 443 [M + H]⁺ ESI |
| 79 | 4-fluorophenyl | 4-(dimethylamino)cyclohexyl-N(H)(CH₃)- | 441 [M + H]⁺ APCI |
| 80 | 4-chlorophenyl | 4-(dimethylamino)cyclohexyl-N(H)(CH₃)- | 457/459 [M + H]⁺ ESI |

Example 81

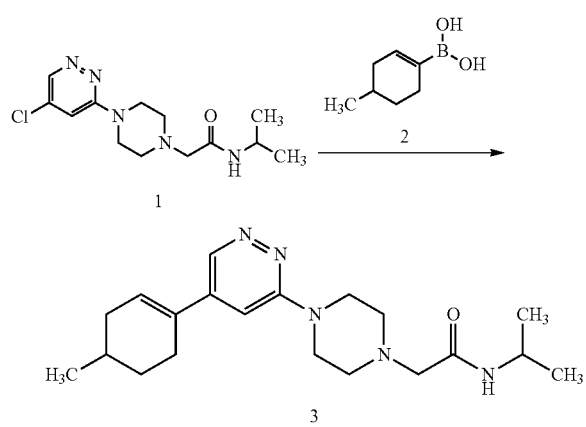

To a solution of the compound 1 (200 mg), the compound 2 (113 mg), an dichlorobis(triphenylphosphine)palladium (24 mg) in dioxane (4 mL) was added a 2 mol/L aqueous solution of sodium carbonate (1.3 mL). The reaction mixture was stirred for 20 minutes at 170° C. in a microwave reactor (Initiator, manufactured by Biotage Inc.) The reaction mixture was cooled to room temperature, and a saturated aqueous solution of sodium carbonate was added thereto. Then, the reaction mixture was extracted with chloroform. The organic layer was washed twice with saturated brine, and dried over anhydrous sodium sulfate. The solvent was distilled off under reduced pressure, then the resultant residue was purified by silica gel column chromatography (eluent: ethyl acetate-methanol; gradient: 100:0-90:10) to give the compound 3 (188 mg) as a colorless solid.

MS (APCI) 358 [M+H]⁺

Examples 82-83

The corresponding starting compound was treated in a similar manner as described in the above Example 81 to give the compounds of the following general formula wherein each R¹ has a structure described in the following Table 10.

TABLE 10

| Example | R[1] | MS |
|---|---|---|
| 82 | 2,3-dihydro-5-methylbenzofuran | 382 [M + H]+ APCI |
| 83 | 5-methyl-2-cyanopyridine | 366 [M + H]+ APCI |

Example 84

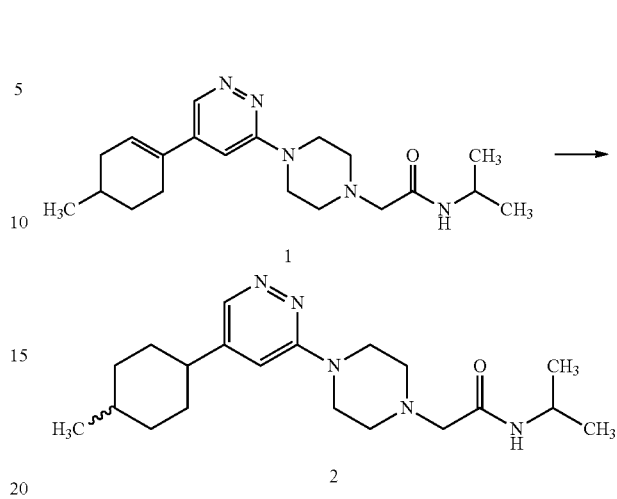

The compound 1 (131 mg) was dissolved in methanol (5.2 mL), and triethylamine (650 m) and 10% wet palladium on carbon (40 mg) were added thereto. The mixture was stirred for 17 hours under hydrogen atmosphere. The palladium on carbon was removed by filtration, and washed with methanol. The filtrate was distilled off under reduced pressure, and the resultant residue was purified by silica gel column chromatography (eluent:ethyl acetate-methanol; gradient: 100:0-90:10) to give the compound 2 (45 mg) as a pale brown solid, which is a mixture of cis and trans forms (11:9, main product is undetermined).

MS (APCI): 360 [M+H]+

Example 85

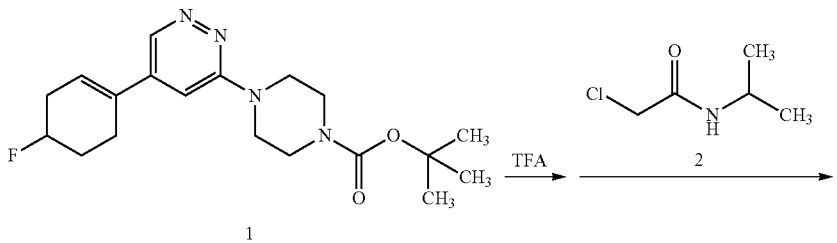

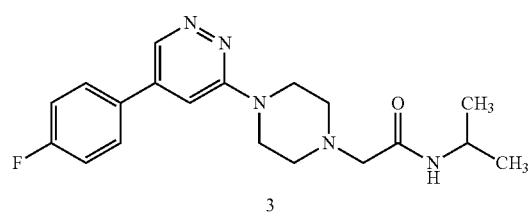

The compound 1 (40 mg) was dissolved in dichloromethane (0.4 mL), and trifluoroacetic acid (0.4 mL) was added thereto. The reaction mixture was diluted with methanol, treated with packed strong cation exchange resin (PoraPak Rxn Cx, eluent: ammonia (1 mol/L methanol solution), and the eluate was concentrated under reduced pressure. The concentrated residue was dissolved in acetonitrile (0.6 mL), and the compound 2 (30 mg) and sodium carbonate (24 mg) were added thereto. The reaction mixture was stirred for 24 hours at 60° C. To the reaction mixture was added a saturated aqueous solution of sodium carbonate, followed by extraction with chloroform. The organic layer was washed with saturated brine, and dried over anhydrous sodium sulfate. The solvent was distilled off under reduced pressure, and the resultant residue was purified by NH-silica gel column chromatography (eluent: hexane-ethyl acetate; gradient: 50:50-0:100) to give the compound 3 (16 mg) as a pale brown solid.

MS (APCI): 358 [M+H]$^+$

Example 86

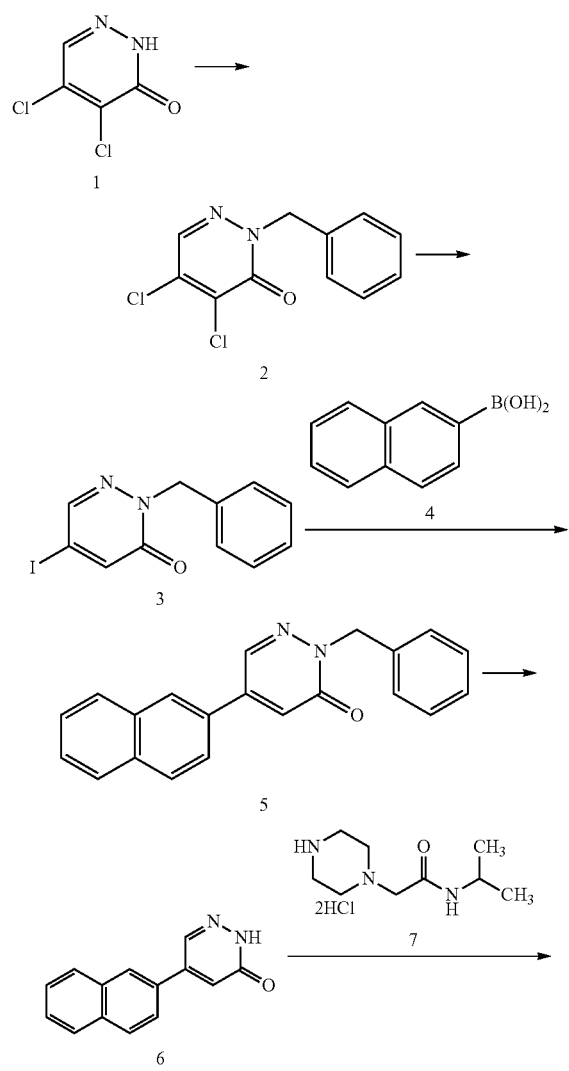

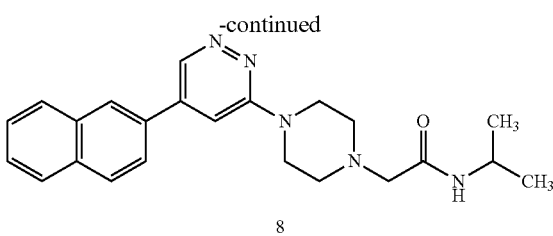

(1) The compound 1 (10 g), benzyl bromide (10.9 g), potassium carbonate (21 g), and tetrabutylammonium bromide (1.0 g) were suspended in acetonitrile (150 mL), and the reaction mixture was stirred for 2 hours under argon atmosphere with heating to reflux. The reaction mixture was cooled to room temperature, and an insoluble substance was filtered off, washed with ethyl acetate, and then the filtrate was concentrated under reduced pressure. The resultant residue was dissolved in chloroform, and the solution was filtered with a silica gel pad (eluent: chloroform). The eluate was concentrated under reduced pressure, and the resultant crystalline residue was suspended and washed in a mixed solvent of ethyl acetate-hexane, taken by filtration, and dried to give the compound 2 (12.2 g) as a pale yellow solid.

MS (APCI): 255/257 [M+H]$^+$ (2) A mixture of the compound 2 (6.0 g), and 57% hydroiodic acid (35 mL) was stirred for 16 hours with heating to reflux. The reaction mixture was cooled to room temperature, poured into an aqueous solution of sodium thiosulfate, and the mixture was extracted with ethyl acetate. The organic layer was dried over anhydrous magnesium sulfate, and the solvent was distilled off under reduced pressure. The resultant residue was purified by silica gel column chromatography (eluent: hexane/ethyl acetate=85:15→chloroform:methanol=90:10) to give the compound 3 (5.3 g) as a pale yellow solid.

MS (APCI): 313 [M+H]$^+$ (3) To a solution of the compound 3 (500 mg), the compound 4 (413 mg), and tetrakis(triphenylphosphine)palladium (93 mg) in dimethoxyethane (8 mL) was added a 2 mol/L aqueous solution of sodium carbonate (1.6 mL). The solution was back-filled with argon, and stirred for 3 hours at 80° C. Subsequently, the compound 4 (200 mg) was added thereto and the mixture was stirred for 16 hours at the same temperature. After the mixture was cooled to room temperature, water was added thereto followed by extraction with chloroform. The organic layer was washed with saturated brine, and dried over anhydrous sodium sulfate. The solvent was distilled off under reduced pressure, and the resultant residue was purified by silica gel column chromatography (eluent: hexane-ethyl acetate; gradient: 85:15-70:30) to give the compound 5 (467 mg) as a colorless solid.

MS (APCI): 313 [M+H]$^+$ (4) To a suspension of aluminum chloride (140 mg) in toluene (2.1 mL), the compound 5 (65 mg) was added little by little at room temperature under argon atmosphere. Thereafter, the mixture was stirred for 1 hour with heating to reflux. The reaction mixture was cooled to room temperature. A 1 mol/L aqueous hydrochloric acid solution was added thereto, followed by extraction with ethyl acetate. The organic layer was dried over anhydrous sodium sulfate, and the solvent was distilled off under reduced pressure. The resultant residue was purified by silica gel column chromatography (eluent: chloroform-ethyl acetate=67:33, isocratic) to give the compound 6 (34 mg) as a pale yellow solid.

MS (APCI): 223 [M+H]$^+$ (5) The compound 6 (30 mg) was dissolved in a mixed solvent of acetonitrile (1 mL)-DMF (five droplets), and the compound 7 (70 mg), diazabicycloundecene (111 μL), and 1H-benzotriazol-1-yloxytris(dimethylamino)phosphonium hexafluorophosphate (BOP, 78 mg) were added thereto. The reaction mixture was stirred for 35 minutes at room temperature, and then, for 15 hours with heating to reflux, and for 20 minutes at 120° C. in a microwave reactor (Initiator, manufactured by Biotage Inc.) The reaction mixture was cooled to room temperature, diluted with ethyl acetate, and washed with water, followed by drying over anhydrous sodium sulfate. The solvent was distilled off under reduced pressure, and the resultant residue was purified by NH-silica gel column chromatography (eluent: chloroform-ethyl acetate; gradient: 90:10-50:50) to give the compound 8 (17 mg) as a pale yellow solid.

MS (APCI): 390 [M+H]$^+$

Example 87

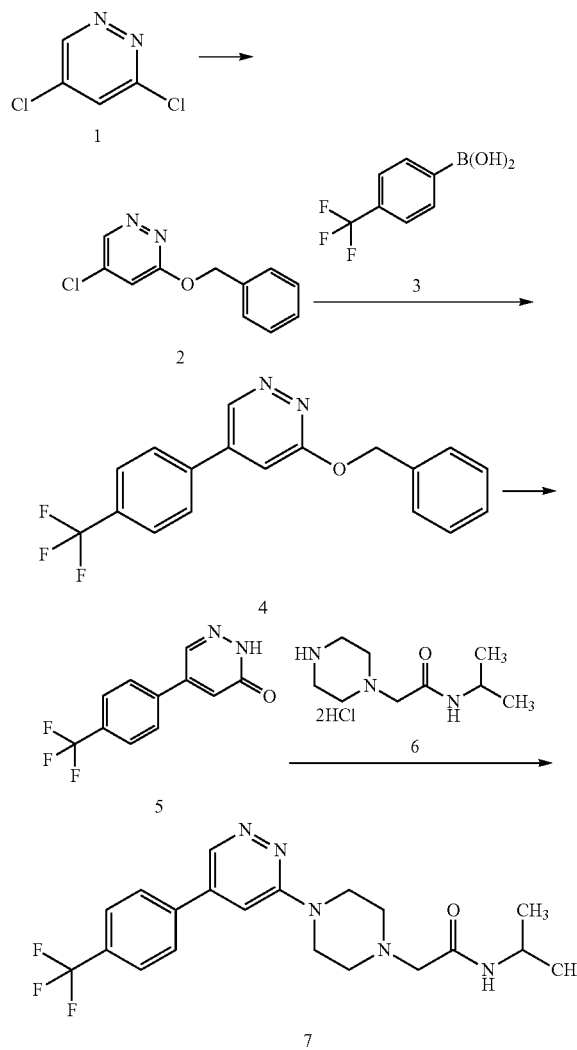

(1) To a suspension of sodium hydride (483 mg) in THF (40 mL) was added a solution of benzyl alcohol (1.1 g) in THF (5 mL) at 0° C. under argon atmosphere, and then the reaction mixture was stirred for 15 minutes at room temperature. Subsequently, a solution of the compound 1 (1.5 g) in THF (20 mL) was added dropwise thereto at room temperature followed by stirring for 2 hours. Water was added to the reaction mixture, and the reaction mixture was extracted with ethyl acetate. The organic layer was washed with water and saturated brine, and then dried over anhydrous sodium sulfate. The solvent was distilled off under reduced pressure, and the resultant residue was purified by silica gel column chromatography (eluent: chloroform-ethyl acetate; gradient: 95:5-85:15) to give the compound 2 (776 mg) as a colorless liquid.

MS (APCI): 221/223 [M+H]$^+$ (2) To a solution of the compound 2 (100 mg), the compound 3 (103 mg), and dichlorobis(triphenylphosphine) palladium (16 mg) in dioxane (2 mL) was added a 2 mol/L aqueous solution of sodium carbonate (1.5 mL), and the reaction mixture was stirred for 15 minutes at 150° C. in a microwave reactor (Initiator, manufactured by Biotage Inc.) After cooled to room temperature, the reaction mixture was diluted with ethyl acetate, washed with water and saturated brine, and dried over anhydrous sodium sulfate. The solvent was distilled off under reduced pressure, and the resultant residue was purified by silica gel column chromatography (eluent: chloroform-ethyl acetate; gradient: 100:0-90:10), and then suspended and washed in a mixed solvent of ethyl acetate-hexane, taken by filtration, and dried to give the compound 4 (69 mg) as a colorless solid.

MS (APCI): 331 [M+H]$^+$ (3) The compound 4 (53 mg) was dissolved in methanol (4 mL), and 10% wet palladium on carbon (27 mg) was added thereto. The mixture was stirred for 15 minutes at room temperature under hydrogen atmosphere. The palladium on carbon was removed by filtration, and washed with methanol. The filtrate was concentrated under reduced pressure to give the compound 5 (37 mg) as a colorless solid.

MS (APCI): 273 [M+H]$^+$ (4) The compound 5 (36 mg) was dissolved in a mixed solvent of acetonitrile (1.5 mL)-dimethylacetamide (1.5 mL). The compound 6 (55 mg), diazabicycloundecene (33 ML), and 1H-benzotriazol-1-yloxytris(dimethylamino) phosphonium hexafluorophosphate (BOP, 86 mg) were added thereto. The reaction mixture was stirred for 2 hours with heating to reflux. The reaction mixture was cooled to room temperature, diluted with ethyl acetate, washed with water and a saturated aqueous solution of sodium hydrogen carbonate, and dried over anhydrous sodium sulfate. The solvent was distilled off under reduced pressure, and the resultant residue was purified by NH-silica gel column chromatography (eluent: chloroform-ethyl acetate; gradient: 90:10-50:50), and then purified by NH-silica gel column chromatography (eluent: chloroform-methanol; gradient: 100:0-90:10) to give the compound 7 (18 mg) as a pale yellow solid.

MS (APCI): 408 [M+H]$^+$

Example 88

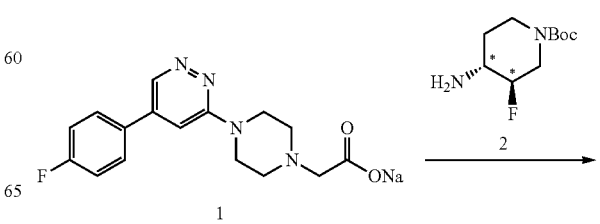

-continued

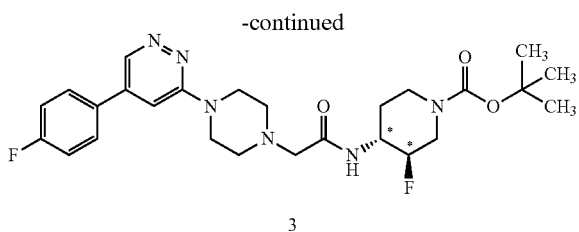

3

(In the scheme, the stereochemistry for a substituent of the carbon atom labelled by "*" means trans configuration, and does not specify their absolute configuration.)

The compound 1 (300 mg) and the compound 2 (290 mg) were suspended in DMF (8.8 mL), and diisopropylethylamine (740 m) and HATU (674 mg) were added thereto. The reaction mixture was stirred for 40 minutes at room temperature. The reaction mixture was diluted with water, and then extracted with chloroform. The organic layer was dried over anhydrous sodium sulfate, and the solvent was distilled off under reduced pressure. The resultant residue was purified by silica gel column chromatography (eluent: hexane-ethyl acetate; gradient: 30:70-0:100) to give the compound 3 (440 mg) as a colorless solid.

MS (APCI): 517 [M+H]$^+$

Example 89a, 89b

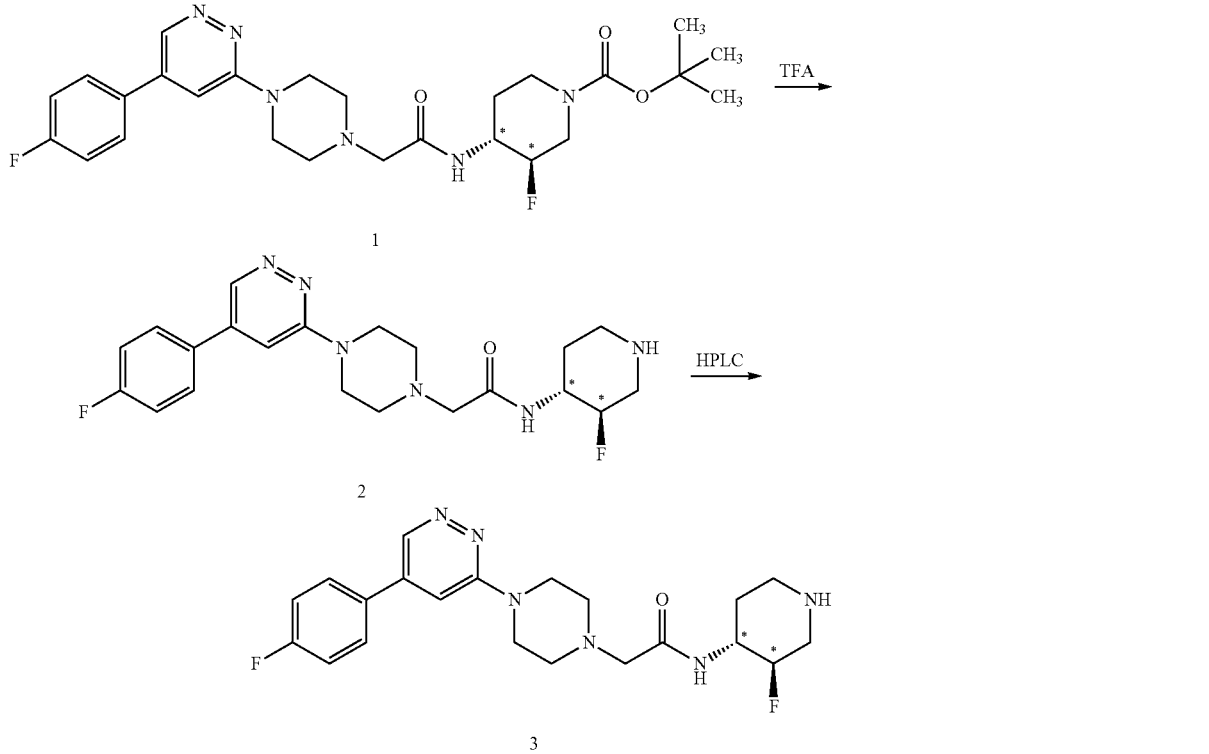

(In the scheme, the stereochemistry for a substituent of the carbon atom labelled by "*" means trans configuration, and does not specify their absolute configuration.)

To a solution of the compound 1 (430 mg) in chloroform (4 mL) was added trifluoroacetic acid (4 mL), and the reaction mixture was stirred for 17 hours at room temperature. The reaction mixture was diluted with methanol, the solution was treated with packed strong cation exchange resin (PoraPak Rxn Cx, eluent: ammonia (1 mol/L methanol solution), and the eluate was concentrated under reduced pressure. The resultant residue was purified by silica gel column chromatography (eluent: chloroform-ammonia water (10% methanol solution)=60:40, isocratic) to give the racemic compound 2 as a colorless solid. The racemic form was fractionated using recycle HPLC (Chiralpak IC (30× 250), methanol/THF/diethylamine=95/5/0.5, flow rate: 20 mL/min) to give respective enantiomers (Example 89a, a colorless solid. 142 mg; and Example 89b, a colorless solid, 69 mg).

Example 89a

Retention time: 9.38 minutes (Chiralpak IC-3 (4.6×150), methanol/THF/diethylamine=95/5/0.5, flow rate 0.5 mL/min)
Optical purity: 98.3% ee
MS (APCI): 417 [M+H]$^+$ Example 89b Retention time: 10.3 minutes (Chiralpak IC-3 (4.6×150), methanol/THF/diethylamine=95/5/0.5, flow rate 0.5 mL/min)
Optical purity: 96.4% ee
MS (APCI): 417 [M+H]$^+$ Example 90a, 90b The corresponding starting compound was treated in a similar manner as described in the above Example 89 to give the compounds of the following general formula wherein each R$^1$ has a structure described in the following Table 11.

However, in the formula, the stereochemistry for a substituent of the carbon atom labelled by "*" means relative configuration, and does not specify their absolute configuration.

HPLC (Chiralpak IC (30×250), methanol/THF/diethylamine=60/40/0.1, flow rate: 20 mL/min) to give respective enantiomers (Example 91a, a colorless solid, 130 mg; and Example 91b, a colorless solid, 132 mg).

TABLE 11

| Example | R¹ | MS | Retention Time | Analysis Condition |
|---|---|---|---|---|
| 90a | (structure: piperidine with NH, *N(H)CH₃, *OH) | 431/433 [M + H]⁺ APCI | 12.43 | Chiralpak IC-3 methanol/acetonitrile/ diethylamine = 80/20/0.5 flow rate: 0.5 mL/min |
| 90b | | 431/433 [M + H]⁺ APCI | 16.14 | Chiralpak IC-3 methanol/acetonitrile/ diethylamine = 80/20/0.5 flow rate: 0.5 mL/min |

Examples 91a, 91b

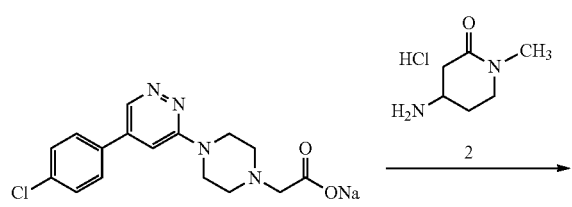

Example 91a

Retention time: 6.42 minutes (Chiralpak IC-3 (4.6×150), methanol/THF/diethylamine=60/40/0.1, flow rate 0.5 mL/min)

Optical purity: >99.8% ee

MS (APCI): 443/445 [M+H]⁺

Example 91b

Retention time: 8.90 minutes (Chiralpak IC-3 (4.6×150), methanol/THF/diethylamine=60/40/0.1, flow rate 0.5 mL/min)

Optical purity: 99.7% ee

MS (APCI): 443/445 [M+H]⁺

Example 92

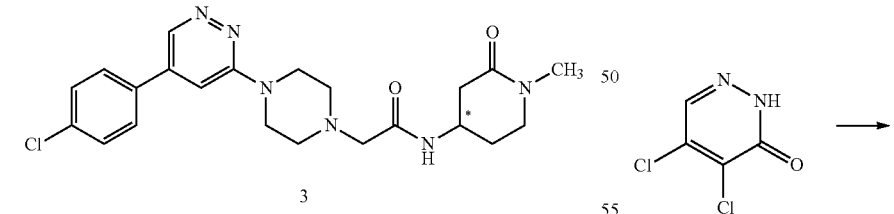

The compound 1 (250 mg) and the compound 2 (139 mg) were dissolved in DMF (7 mL), and diisopropylethylamine (493 μL) and HATU (268 mg) were added thereto. The reaction mixture was stirred for 2 hours at room temperature. The reaction mixture was diluted with water, and extracted with chloroform. The organic layer was dried over anhydrous sodium sulfate, and the solvent was distilled off under reduced pressure. The resultant residue was purified by NH-silica gel column chromatography (eluent: chloroform-methanol; gradient: 100:0-92:8) to give the racemic compound 3. The racemic form was fractionated using recycle

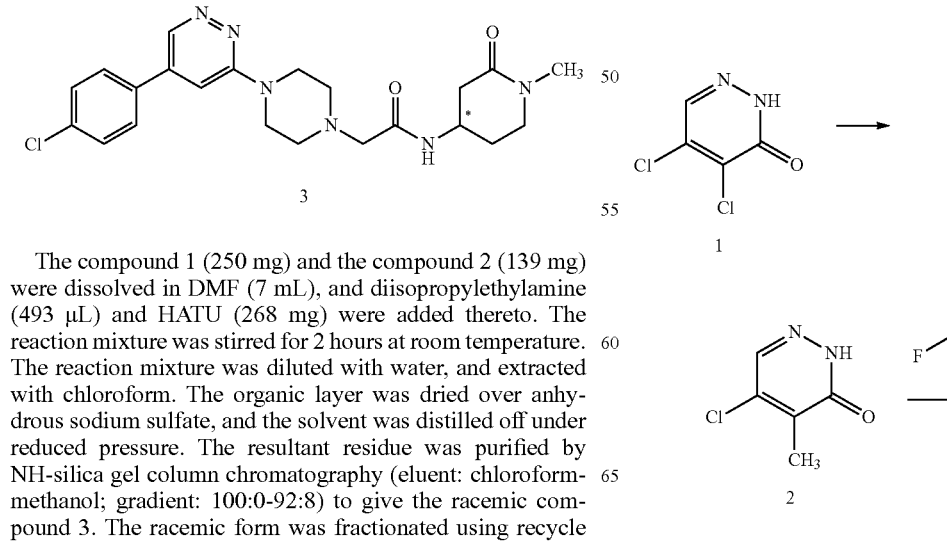

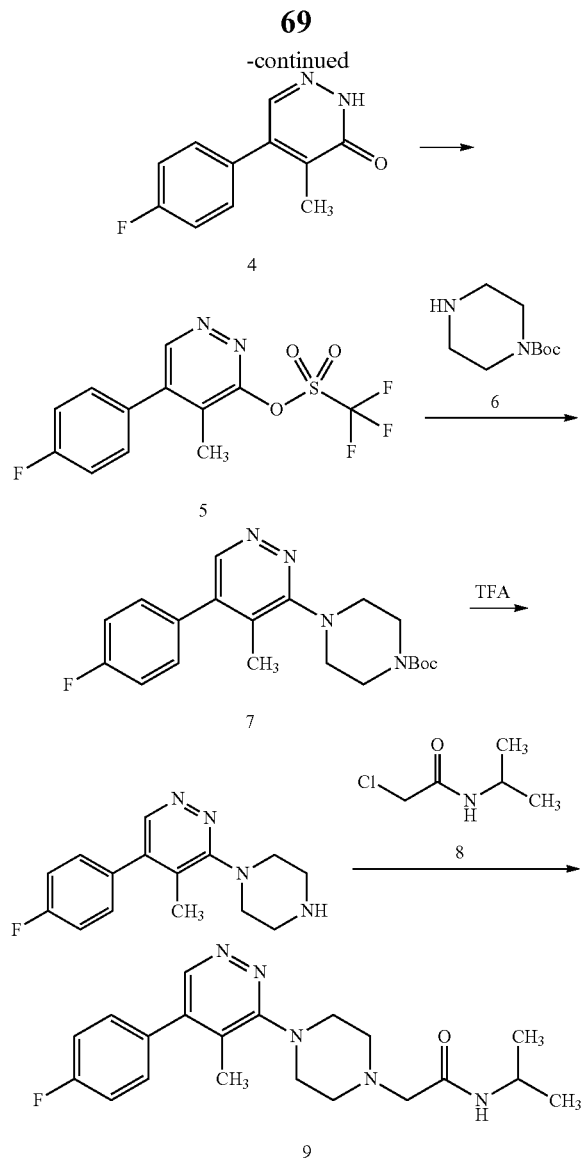

(1) The compound 1 (4.0 g) was dissolved in a mixed solvent of THF (60 mL)-diethyl ether (60 mL), and methylmagnesium bromide (0.92 mol/L, THF solution, 61 mL) was added dropwise thereto at room temperature under argon atmosphere. Then, the mixture was stirred for 5 hours with heating to reflux. After cooled to room temperature, a 2 mol/L aqueous hydrochloric acid solution was added thereto, followed by extraction with chloroform. The organic layer was dried over sodium sulfate, and then the solvent was distilled off under reduced pressure. The resultant residue was purified by silica gel column chromatography (eluent: hexane-ethyl acetate; gradient: 80:20-60:40), and then suspended and washed in diisopropyl ether, taken by filtration, and dried to give the compound 2 (650 mg) as a colorless solid.

MS (APCI): 145/147 [M+H]$^+$ (2) To a solution of the compound 2 (1.0 g), the compound 3 (4.2 g), and a solution of 1,1'-bis(diphenylphosphino)ferrocene palladium dichloride dichloromethane complex (252 mg) in dioxane (35 mL) was added a 2 mol/L aqueous solution of sodium carbonate (14 mL). After argon substitution, the solution was stirred for 20 hours at 80° C. The mixture was cooled to room temperature, and then diluted with water. Thereafter, the mixture was extracted with chloroform. The organic layer was dried over anhydrous sodium sulfate. The solvent was distilled off under reduced pressure, and the resultant residue was purified by silica gel column chromatography (eluent: hexane-ethyl acetate; gradient: 80:20-30:70) to give the compound 4 (200 mg).

MS (APCI): 205 [M+H]$^+$ (3) The compound 4 (100 mg) was suspended in pyridine (2.5 mL), and trifluoromethanesulfonic anhydride (165 mL) was added thereto under ice cooling. The reaction mixture was stirred for 1 hour at the same temperature. The reaction mixture was diluted with water, and extracted with chloroform. The organic layer was dried over anhydrous sodium sulfate. The solvent was distilled off under reduced pressure, and the resultant residue was purified by silica gel column chromatography (eluent: hexane/ethyl acetate; gradient: 95:5-85:15) to give the compound 5 (126 mg). After the compound 5 (100 mg) was dissolved in dimethyl sulfoxide (3 mL), the compound 6 (553 mg) and diisopropylethylamine (260 μm) were added thereto, and the mixture was stirred with heating for 4 hours at 50° C. After the mixture was cooled to room temperature, water was added thereto, followed by extraction with a mixed solvent of ethyl acetate-hexane. The organic layer was dried over sodium sulfate. The solvent was distilled off under reduced pressure, and the resultant residue was purified by silica gel column chromatography (eluent: hexane-ethyl acetate; gradient: 70:30-50:50), and then by NH-silica gel column chromatography (eluent: hexane-ethyl acetate; gradient: 90:10-0:100) to give the compound 7 (51 mg).

MS (APCI): 373 [M+H]$^+$ (4) To a solution of the compound 7 (50 mg) in chloroform (0.5 mL) was added trifluoroacetic acid (0.5 mL), and the reaction mixture was stirred for 1.5 hours at room temperature. After the reaction mixture was diluted with methanol, treated with packed strong cation exchange resin (PoraPak Rxn Cx, eluent: ammonia (1 mol/L methanol solution), and the eluate was concentrated under reduced pressure. The concentrated residue was dissolved in acetonitrile (1.3 mL), sodium carbonate (71 mg) and the compound 8 (55 mg) were added thereto. The reaction mixture was stirred for 20 hours at 65° C. The reaction mixture was diluted with water, and then extracted with ethyl acetate. The organic layer was dried over anhydrous sodium sulfate. The solvent was distilled off under reduced pressure, and the resultant residue was purified by NH-silica gel column chromatography (eluent: hexane-ethyl acetate; gradient: 50:50-30:70) to give the compound 9 (32 mg) as a colorless solid.

MS (APCI): 372 [M+H]$^+$

The compounds of the above Examples, any commercially available reagents or any compounds which have been made through chemical modification of the reagents using conventional methods and other methods based thereon can be used as a starting material and an intermediate. In addition, they can be prepared by the methods described in the following Reference Examples.

Reference Example 1

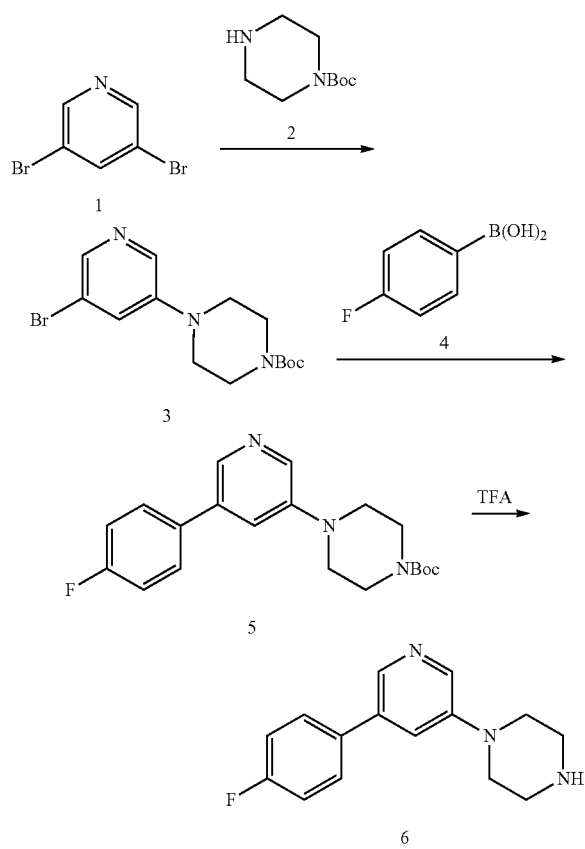

(1) A solution of the compound 1 (11.6 g), the compound 2 (7.0 g), tris(dibenzylideneacetone)dipalladium (688 mg), 4,5-bis(diphenylphosphino)-9,9-dimethylxanthene (1.3 g), and sodium t-butoxide (5.4 g) in toluene (300 mL) was degassed under reduced pressure, and then back-filled with argon. The reaction mixture was stirred for 18 hours at 100° C. The reaction mixture was cooled to room temperature, and the solvent was distilled off under reduced pressure. The resultant residue was diluted with water and ethyl acetate, and the organic layer was washed with saturated brine, followed by drying over anhydrous magnesium sulfate. The solvent was distilled off under reduced pressure, and the resultant residue was purified by silica gel column chromatography (eluent: hexane-ethyl acetate; gradient: 80:20-65:35), and the resultant crystalline residue was suspended and washed in ethyl acetate-hexane, taken by filtration, and dried to give the compound 3 (10.1 g) as a pale yellow solid.

MS (APCI): 342/344 [M+H]$^+$ (2) To a mixed solution of the compound 3 (8.8 g), the compound 4 (7.2 g), and dichlorobis(triphenylphosphine)palladium (905 mg) in dioxane (130 mL) was added a 2 mol/L aqueous solution of sodium carbonate (52 mL), and the reaction mixture was stirred at 80° C. for 1 hour. The reaction mixture was cooled to room temperature, and water was added thereto, followed by extraction 3 times with chloroform. After drying over anhydrous sodium sulfate, the solvent was distilled off under reduced pressure, and the resultant residue purified by silica gel column chromatography (eluent: chloroform-ethyl acetate; gradient: 10:1-25:1) to give the compound 5 (8.1 g) as a colorless solid.

MS (APCI): 358 [M+H]$^+$ (3) To a solution of the compound 5 (8.1 g) in dichloromethane (81 mL) was added trifluoroacetic acid (81 mL) under ice cooling, and the reaction mixture was stirred for 1 hour at room temperature. The solvent of the reaction mixture was distilled off, and then the reaction mixture was dissolved in chloroform. Thereafter, the solution was neutralized with a 1 mol/L aqueous sodium hydroxide solution. The organic layer was separated from the aqueous layer, and the aqueous layer was extracted 3 times with chloroform. After the organic layer was extracted with water, it was dried over anhydrous sodium sulfate. Then, the solvent was distilled off under reduced pressure. The resultant crystalline residue was suspended and washed in diethyl ether-hexane, taken by filtration, and dried to give the compound 6 (1.2 g) as a colorless solid.

MS (APCI): 258 [M+H]$^+$

Reference Example 2-5

The corresponding starting compound was treated in a similar manner as described in the above Reference Example 1 to give the compounds described in the following Table 12.

TABLE 12

| Ref. Ex. | Structure | MS |
|---|---|---|
| 2 | 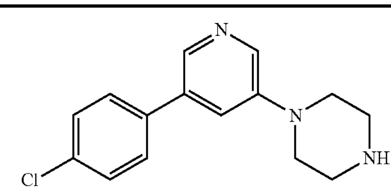 | 274/276 [M + H]$^+$ APCI |
| 3 | 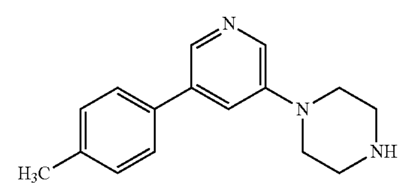 [SMILES: Cc1ccc(-c2cncc(N3CCNCC3)c2)cc1] | 254 [M + H]$^+$ APCI |
| 4 | 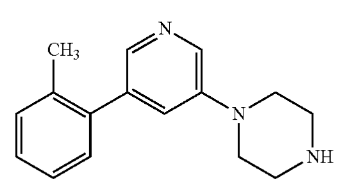 [SMILES: Cc1ccccc1-c1cncc(N2CCNCC2)c1] | 254 [M + H]$^+$ APCI |
| 5 | 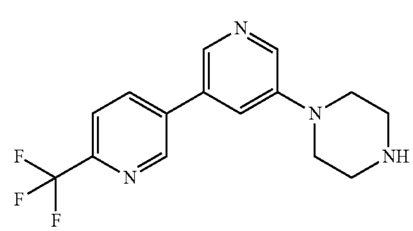 [SMILES: FC(F)(F)c1ccc(-c2cncc(N3CCNCC3)c2)cn1] | 309 [M + H]$^+$ APCI |

Reference Example 6

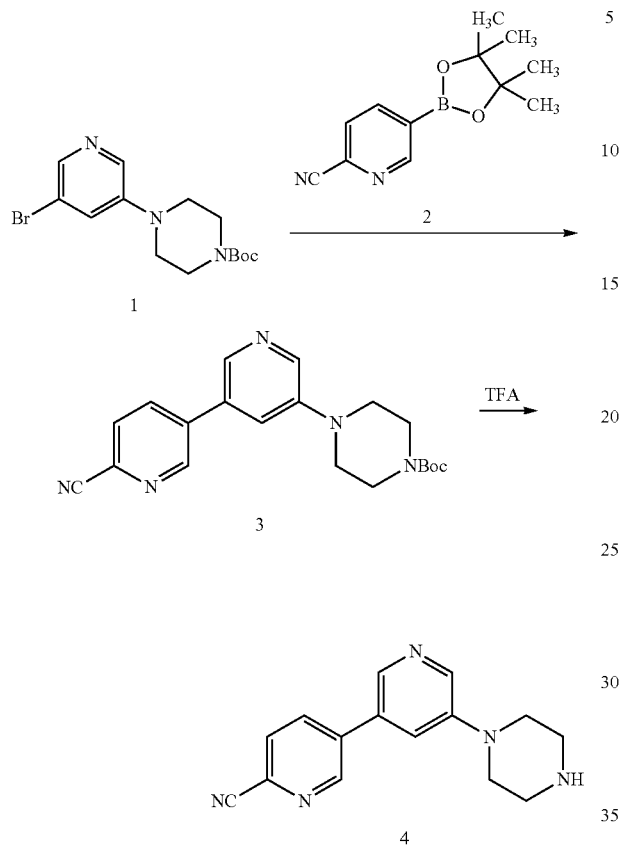

(1) A mixed solution of the compound 1 (342 mg), the compound 2 (353 mg), tris(dibenzylideneacetone)dipalladium (46 mg), tri-t-butylphosphine (1 mol/L toluene solution, 100 μL), and cesium carbonate (1.3 g) in THF (15 mL) was degassed under reduced pressure, and then back-filled with argon. The reaction mixture was stirred for 1 hour with heating to reflux. The reaction mixture was cooled to room temperature, diluted with ethyl acetate-water, and then celite-filtered. The filtrate was washed with water and saturated brine, and then dried over anhydrous magnesium sulfate. The solvent was distilled off under reduced pressure, and the resultant residue was purified by silica gel column chromatography (eluent: hexane-ethyl acetate; gradient: 50:50-10:90) to give the compound 3 (302 mg) as a yellow solid.

MS (APCI): 366 [M+H]$^+$ (2) To a solution of the compound 3 (292 mg) and thioanisole (993 mg) in dichloromethane (4 mL) was added trifluoroacetic acid (2 mL), and the reaction mixture was stirred for 3 hours at room temperature. The reaction mixture was diluted with methanol, treated with packed strong cation exchange resin (PoraPak Rxn Cx, eluent: ammonia (1 mol/L methanol solution)), and the eluate was concentrated under reduced pressure. The resultant residue was purified by silica gel chromatography (eluent: chloroform-ammonia water (10% methanol solution)) to give the compound 4.

MS (APCI): 266 [M+H]$^+$

Reference Example 7

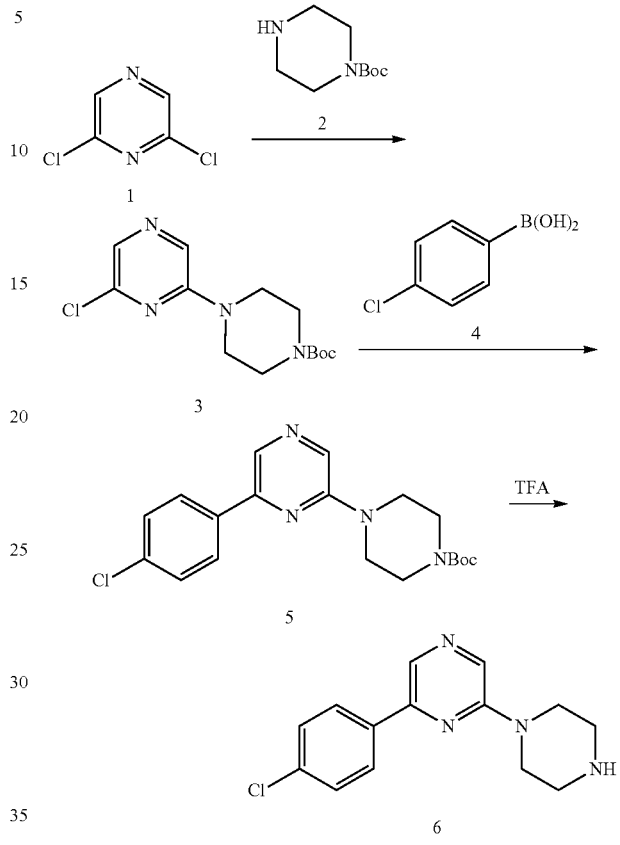

(1) A solution of the compound 1 (7.5 g), and the compound 2 (20.6 g) in acetonitrile (150 mL) was heated to reflux under argon atmosphere for 22 hours. The reaction mixture was cooled to room temperature, and the produced precipitate was removed by filtration. Thereafter, the solvent of the filtrate was distilled off under reduced pressure. The resultant residue was diluted with chloroform, washed with water and saturated brine, and dried over anhydrous magnesium sulfate. The solvent was distilled off under reduced pressure, and the resultant residue was purified by silica gel column chromatography (eluent: chloroform-ethyl acetate=80:20) to give the compound 3 (14.2 g) as a colorless solid.

MS (APCI): 299/301 [M+H]$^+$ (2) A mixed solution of the compound 3 (2.0 g), the compound 4 (1.1 g), tris(dibenzylideneacetone)dipalladium (306 mg), tri-t-butylphosphine (1 mol/L toluene solution, 0.67 mL), and cesium carbonate (8.7 g) in THF (100 mL) was heated to reflux for 21 hours under argon atmosphere. The reaction mixture was cooled to room temperature, diluted with ethyl acetate/water, and celite-filtered. The filtrate was washed with water and saturated brine, and dried over anhydrous magnesium sulfate. The solvent was distilled off under reduced pressure, and the resultant residue was purified by silica gel column chromatography (eluent: hexane-ethyl acetate; gradient: 80:20-60:40), and the resultant crystalline residue was suspended and washed in ethyl acetate-hexane, taken by filtration, and dried to give the compound 5 (1.3 g) as a yellow solid.

MS (APCI): 375/377 [M+H]$^+$ (3) To a solution of the compound 5 (1.3 g) in dichloromethane (10 mL) was added trifluoroacetic acid (5 mL), and the reaction mixture was stirred for 18 hours at room temperature. The reaction mixture was diluted with methanol and then treated with packed strong cation exchange resin (PoraPak Rxn Cx, eluent: ammonia (1 mol/L methanol solution), and the crystalline residue obtained by concentrating the eluate under reduced pressure was suspended and washed in diisopropyl ether-hexane, taken by filtration, and dried to give the compound 6 (849 mg) as a yellow solid.

MS (APCI): 275/277 [M+H]+

Reference Examples 8-13

The corresponding starting compound was treated in a similar manner as described in the above Reference Example 7 to give the compounds described in the following Table 13.

TABLE 13

| Ref. Ex. | Structure | MS |
|---|---|---|
| 8 | 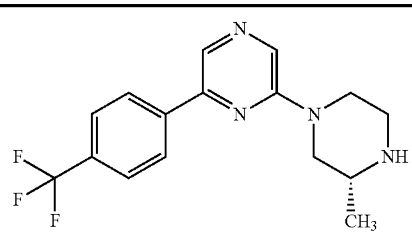 | 323 [M + H]+ APCI |
| 9 | 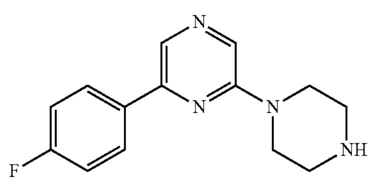 [SMILES: Fc1ccc(-c2cncc(N3CCNCC3)n2)cc1] | 259 [M + H]+ APCI |
| 10 | 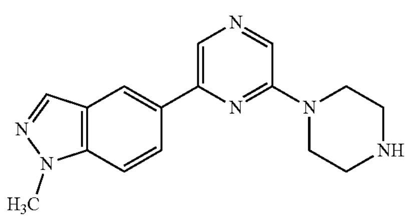 [SMILES: Cn1ncc2cc(-c3cncc(N4CCNCC4)n3)ccc21] | 295 [M + H]+ APCI |
| 11 | 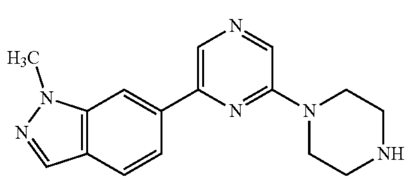 [SMILES: Cn1ncc2ccc(-c3cncc(N4CCNCC4)n3)cc21] | 295 [M + H]+ APCI |
| 12 | 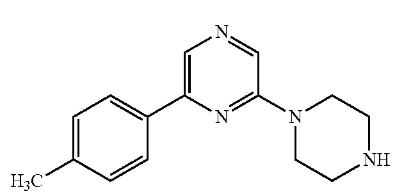 [SMILES: Cc1ccc(-c2cncc(N3CCNCC3)n2)cc1] | 255 [M + H]+ APCI |

TABLE 13-continued

| Ref. Ex. | Structure | MS |
|---|---|---|
| 13 | 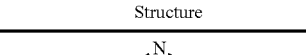 | 255 [M + H]+ APCI |

Reference Example 14

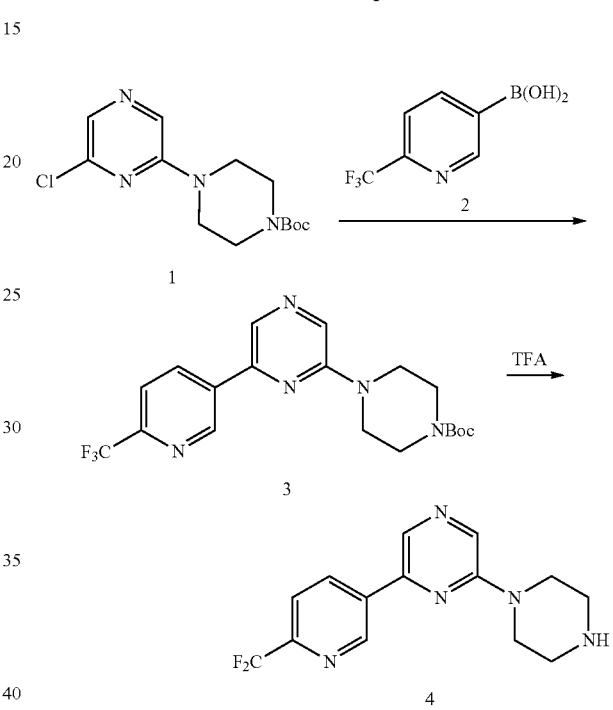

(1) To a mixed solution of the compound 1 (149 mg), the compound 2 (114 mg), and dichlorobis(triphenylphosphine) palladium (18 mg) in dioxane (2 mL) was added a 2 mol/L aqueous solution of sodium carbonate (1.5 mL). The reaction mixture was stirred for 15 minutes at 150° C. in a microwave reactor (Initiator, manufactured by Biotage Inc.) The reaction mixture was cooled to room temperature, diluted with ethyl acetate, washed with water, and dried over Chem Elut (registered trademark). The solvent was distilled off under reduced pressure, and the resultant residue was purified by silica gel column chromatography (eluent: hexane-ethyl acetate; gradient: 50:50-20:80) to give the compound 3 (190 mg) as a colorless solid.

MS (APCI) 410 [M+H]+

(2) To a solution of the compound 3 (182 mg) in dichloromethane (2 mL) was added trifluoroacetic acid (1 mL) under ice cooling, and the reaction mixture was stirred for 2 hours at room temperature. The reaction mixture was diluted with methanol, and treated with packed strong cation exchange resin (PoraPak Rxn Cx, eluent: ammonia (1 mol/L methanol solution), and the eluate was concentrated under reduced pressure to give the compound 4 (142 mg) as a yellow solid.

MS (APCI) 310 [M+H]+

Reference Example 15

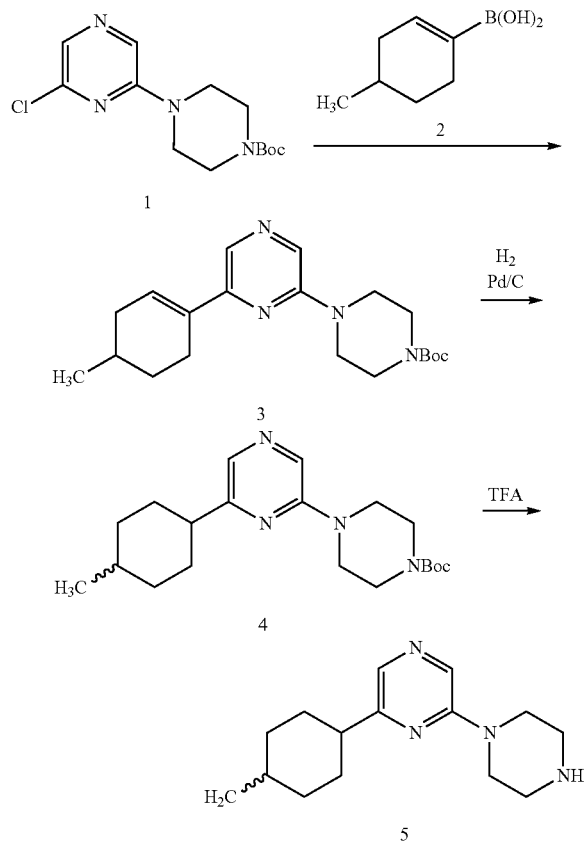

(1) A mixed solution of the compound 1 (1.5 g), the compound 2 (1.0 g), tris(dibenzylideneacetone)dipalladium (230 mg), tri-t-butylphosphine (1 mol/L hexane solution, 1.4 mL), and cesium carbonate (6.5 g) in THF (50 mL) was stirred with heating to reflux for 2.5 hours under argon atmosphere. The reaction mixture was cooled to room temperature, and diluted with ethyl acetate/water. The aqueous layer was extracted with ethyl acetate, and dried over sodium sulfate. The solvent was distilled off under reduced pressure, and the resultant residue was purified by silica gel column chromatography (eluent: hexane-ethyl acetate; gradient: 90:10-65:35) to give the compound 3 (1.8 g) as a pale yellow solid.

MS (ESI): 359 [M+H]$^+$ (2) To a solution of the compound 3 (1.78 g) and triethylamine (9 mL) in methanol (50 mL) was added 10% wet palladium on carbon (530 mg), and the reaction mixture was stirred for 2 hours under hydrogen atmosphere. The reaction mixture was celite-filtered, and the solvent was distilled off under reduced pressure. Thereafter, a methanol solution (50 mL) was prepared again. Triethylamine (9 mL) and 10% wet palladium on carbon (530 mg) were added thereto, and the reaction mixture was stirred for 18 hours at room temperature under hydrogen atmosphere. After the reaction mixture was celite-filtered, the solvent was distilled off under reduced pressure. The resultant residue was purified by silica gel column chromatography (eluent: hexane-ethyl acetate; gradient: 80:20-60:40) to give the compound 4 (1.4 g) as a pale yellow viscous substance, which is a mixture of cis and trans forms (=3:2, main product is undetermined).

MS (APCI): 361 [M+H]$^+$ (3) To a solution of the compound (200 mg) in chloroform (3 mL) was added trifluoroacetic acid (6 mL), and the reaction mixture was stirred for 22 hours at room temperature. The reaction mixture was diluted with methanol, and then treated with packed strong cation exchange resin (Pora-Pak Rxn Cx, eluent: ammonia (1 mol/L methanol solution). The eluate was concentrated under reduced pressure to give the compound 5 (121 mg) as a yellow solid, which is a mixture of cis and trans forms (=3:2, main product is undetermined).

MS (APCI): 261 [M+H]$^+$

Reference Example 16

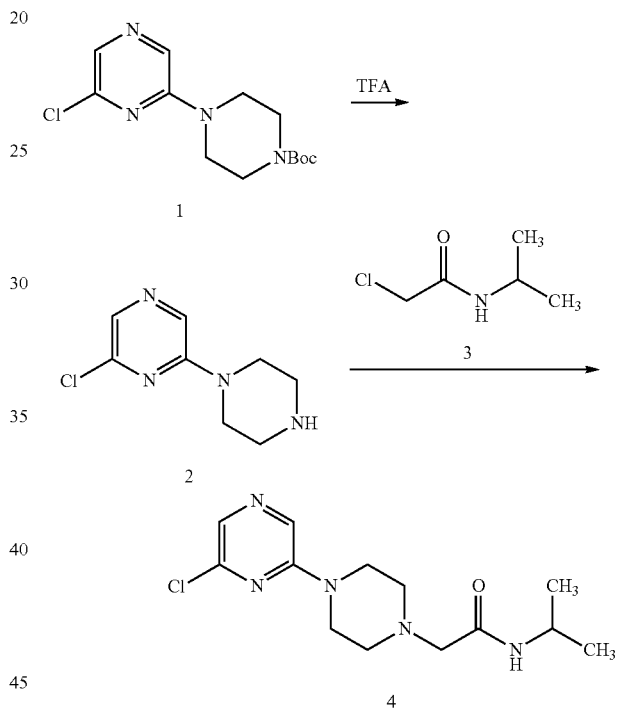

To a solution of the compound (600 mg) in dichloromethane (5 mL) was added trifluoroacetic acid (4.5 mL), and the reaction mixture was stirred for 3.5 hours at room temperature. The reaction mixture was diluted with methanol, and then treated with packed strong cation exchange resin (Pora-Pak Rxn Cx, eluent: ammonia (1 mol/L methanol solution). The eluate was concentrated under reduced pressure to give the compound 2 (289 mg) as a pale yellow viscous substance. A mixed solution of the resultant compound 2 (289 mg), the compound 3 (397 mg), and sodium carbonate (309 mg) in acetonitrile (3 mL) was stirred for 1 day at 50° C. under argon atmosphere. The reaction mixture was cooled to room temperature, and a saturated aqueous solution of sodium hydrogen carbonate was added thereto, followed by extraction twice with chloroform. The organic layer was washed with saturated brine, and dried over anhydrous sodium sulfate. The solvent was distilled off under reduced pressure, and the resultant residue was purified by silica gel column chromatography (eluent: chloroform-methanol;

gradient: 100:0-95:5) to give the compound 4 (398 mg) as a yellow solid.

MS (APCI): 298/300 [M+H]+

Reference Example 17

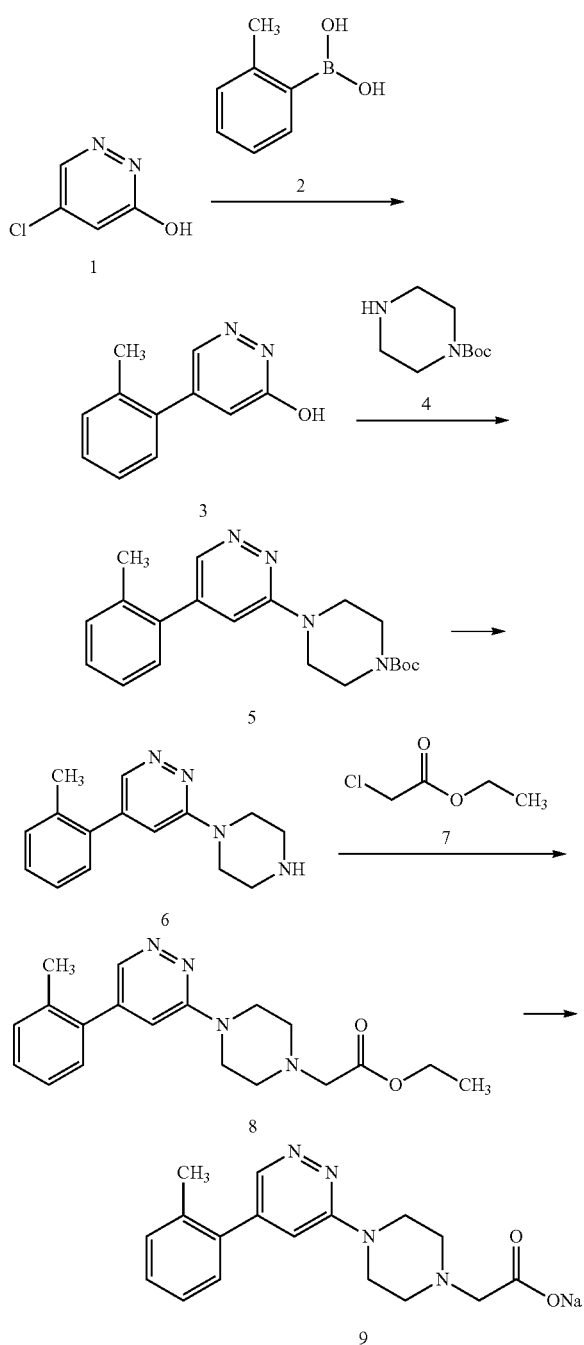

(1) To a solution of the compound 1 (4.0 g), the compound 2 (8.33 g), and a solution of 1,1'-bis(diphenylphosphino)ferrocene palladium dichloride dichloromethane complex (1.3 g) in dioxane (150 mL) was added a 2 mol/L aqueous solution of sodium carbonate (46 mL). After argon substitution, the reaction mixture was stirred for 3 hours at 80° C. The reaction mixture was cooled to room temperature, diluted with chloroform, washed with a 10% aqueous solution of sodium carbonate, and dried over anhydrous sodium sulfate. The solvent was distilled off under reduced pressure, and the resultant residue was purified by silica gel column chromatography (eluent: hexane-ethyl acetate; gradient: 80:20-50:50) to give the compound 3 (4.26 g) as a colorless solid.

MS (APCI): 187 [M+H]+

(2) The compound 3 (4.26 g), the compound 4 (12.8 g), 1H-benzotriazol-1-yloxytris(dimethylamino)phosphonium hexafluorophosphate (BOP, 15.2 g), and diazabicycloundecene (10.3 mL) were added to DMF (110 mL). After argon substitution, the reaction mixture was stirred for 18 hours at 80° C. After the reaction mixture was cooled to room temperature, water was added thereto, followed by extraction with ethyl acetate. The organic layer was washed with a saturated aqueous solution of sodium hydrogen carbonate, saturated brine, and dried over anhydrous sodium sulfate. The solvent was distilled off under reduced pressure, and the resultant residue was purified by silica gel column chromatography (eluent: chloroform-ethyl acetate; gradient: 100:0-90:10) to give the compound 5 (5.0 g) as a yellow solid.

MS (APCI): 355 [M+H]+

(3) The compound 5 (5.0 g) was dissolved in chloroform (70 mL), and trifluoroacetic acid (70 mL) was added thereto. The mixture was stirred for 3 hours at room temperature. The solvent was distilled off under reduced pressure, and to the residue was added a 20% aqueous solution of potassium carbonate, followed by extraction with chloroform. The organic layer was washed with water and saturated brine, and dried over anhydrous sodium sulfate. The solvent was distilled off under reduced pressure. The resultant residue was purified by NH-silica gel column chromatography (eluent: chloroform-ethyl acetate; gradient: 100:0-50:50), and then suspended and washed in diisopropyl ether, taken by filtration, and dried to give the compound 6 (3.20 g) as a colorless solid.

MS (APCI): 255 [M+H]+

(4) The compound 6 (3.20 g) was dissolved in acetonitrile (60 mL), and the compound 7 (1.70 g) and sodium carbonate (2.67 g) were added thereto. The mixture was stirred for 18 hours at 65° C. The solvent was distilled off under reduced pressure, and to the residue was added water, followed by extraction with chloroform. The organic layer was washed with saturated brine, and dried over anhydrous sodium sulfate. The solvent was distilled off under reduced pressure. The resultant residue was purified by silica gel column chromatography (eluent:ethyl acetate-methanol; gradient: 100:0-95:5), and then suspended and washed in diisopropyl ether, taken by filtration, and dried to give the compound 8 (2.40 g) as a brown solid.

MS (APCI): 341 [M+H]+

(5) The compound 8 (2.40 g) was dissolved in ethanol (50 mL), and a 1 mol/L aqueous sodium hydroxide solution (5.3 mL) was added thereto, followed by stirring for 3 hours at room temperature. The reaction mixture was concentrated, and ethanol was added to the resultant residue. The mixture was suspended and washed, taken by filtration, and dried to give the compound 9 (2.10 g) as a colorless solid.

MS (ESI): 311 [M+Na]+

Reference Examples 18-20

The corresponding starting compound was treated in a similar manner as described in the above Reference Example 17 to give the compounds described in the following Table 14.

TABLE 14

| Ref. Ex. | R¹ | MS |
|---|---|---|
| 18 | 4-methylphenyl (H₃C–C₆H₄–) | 311 [M + Na]⁻ ESI |
| 19 | 4-fluoro-3-methylphenyl | 315 [M + Na]⁻ ESI |
| 20 | 4-chloro-3-methylphenyl | 331/333 [M + Na]⁻ ESI |

Reference Example 21

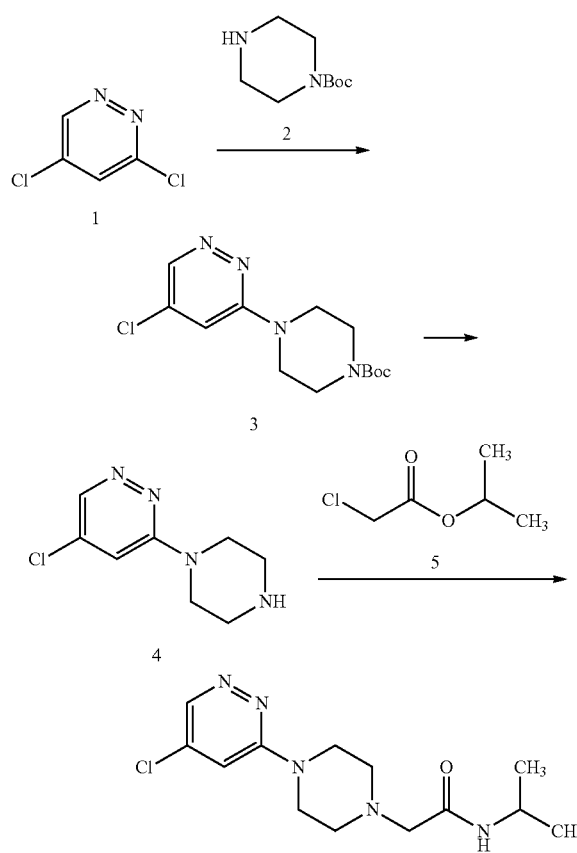

(1) The compound 1 (18.5 g), the compound 2 (27.7 g), and potassium carbonate (51.3 g) were suspended in 1,2-dichloroethane (125 mL), and the reaction mixture was stirred for 3 hours at 85° C. Then, the compound 2 (4.6 g), and potassium carbonate (17 g) were added to the reaction mixture, followed by stirring for 3 hours at the same temperature. Thereafter, the compound 2 (13.8 g) was added thereto, followed by stirring further for 1 hour. After the reaction mixture was cooled to room temperature, and an insoluble substance was filtered off. The filtrate was concentrated under reduced pressure. The resultant residue was purified by silica gel column chromatography (eluent: hexane-ethyl acetate:gradient: 80:20-60:40), and then suspended and washed in hexane, taken by filtration, and dried to give the compound 3 (4.2 g) as a colorless solid.

MS (APCI): 299/301 [M+H]⁺

(2) The compound 3 (600 mg) was dissolved in chloroform (6 mL), and trifluoroacetic acid (12 mL) was added thereto, followed by stirring for 23 hours at room temperature. The reaction mixture was diluted with methanol, and then treated with packed strong cation exchange resin (PoraPak Rxn Cx, eluent: ammonia (1 mol/L methanol solution). The eluate was concentrated under reduced pressure to give the compound 4 (315 mg) as a pale yellow solid.

MS (APCI) 199/201 [M+H]⁺

(3) The compound 4 (312 mg) was dissolved in acetonitrile. The compound 5 (319 mg) and sodium carbonate (333 mg) were added thereto, followed by stirring for 4 days at room temperature. A saturated aqueous solution of sodium carbonate was added to the reaction mixture, followed by extraction with chloroform. The organic layer was washed with saturated brine, and dried over anhydrous sodium carbonate. The solvent was distilled off under reduced pressure, and the resultant residue was purified by silica gel column chromatography (eluent:ethyl acetate-methanol:gradient: 100:0-90:10) to give the compound 6 (405 mg) as a colorless solid.

MS (APCI) 298/00 [M+H]⁺

Reference Example 22

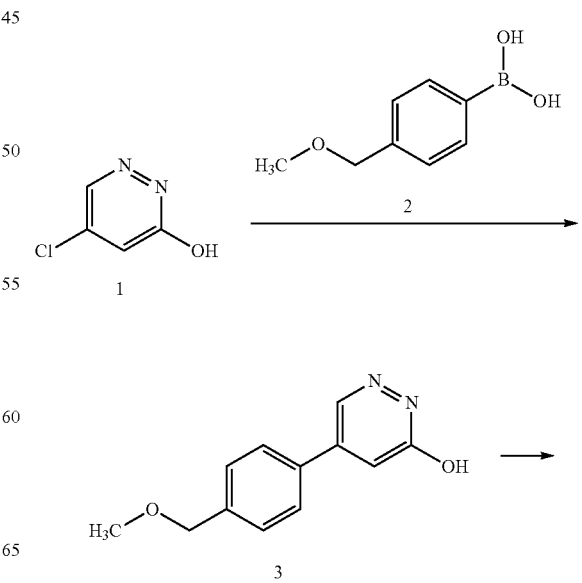

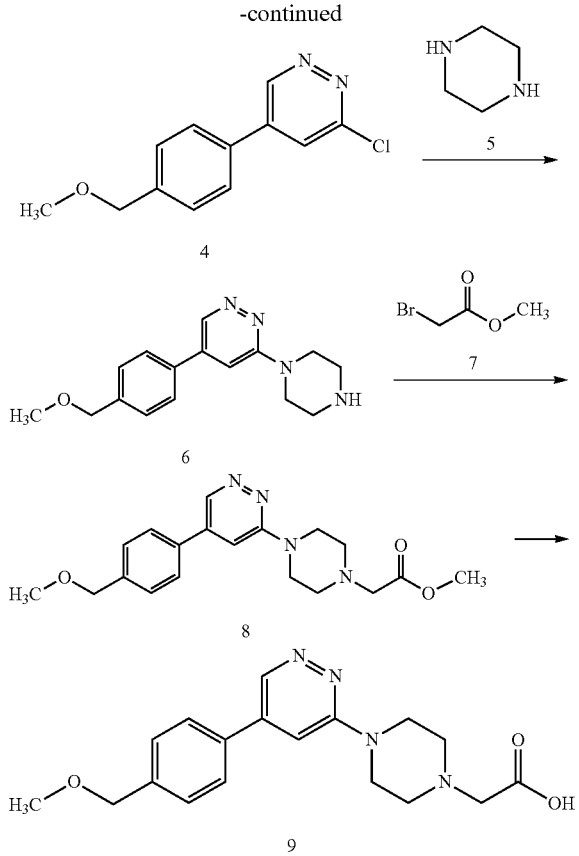

(1) To a solution of the compound 1 (4.0 g), the compound 2 (6.1 g), and 1,1'-bis(diphenylphosphino) ferrocene palladium dichloride dichloromethane complex (1.25 g) in dioxane (150 mL) was added a 2 mol/L aqueous solution of sodium carbonate (46 mL). After argon substitution, the reaction mixture was stirred for 20 hours at 80° C. After cooled to room temperature, the reaction mixture was diluted with ethyl acetate, and washed with water and saturated brine. Thereafter, the insoluble precipitate was filtered off. The aqueous layer was extracted with chloroform, and the combined organic layer was dried over anhydrous magnesium sulfate. The solvent was distilled off under reduced pressure, and the resultant residue was suspended and washed in ethyl acetate, taken by filtration, and dried to give the compound 3 (4.6 g) as a pale brown solid.

MS (APCI): 217 [M+H]$^+$ (2) The compound 3 (4.3 g) was added to phosphorous oxychloride (30.5 g), and the reaction mixture was stirred for 25 minutes at 25° C. After the reaction mixture was concentrated under reduced pressure, chloroform and a saturated aqueous solution of sodium carbonate were added to the residue to filter off an insoluble substance. The organic layer of the filtrate was dried over anhydrous magnesium sulfate, and then the solvent was distilled off under reduced pressure. The resultant residue was purified by silica gel column chromatography (eluent: hexane-ethyl acetate; gradient: 80:20-50:50) to give the compound 4 (613 mg) as a pale yellow solid.

MS (APCI): 235/237 [M+H]$^+$ (3) The compound 4 (285 mg) and the compound 5 (1.05 g) were suspended in dimethylacetamide (4 mL), and the suspension was stirred for 20 minutes at 120° C. in a microwave reactor (Initiator, manufactured by Biotage Inc.) A similar operation was repeated. To the combined reaction mixture was added an aqueous solution of potassium carbonate, followed by extraction with chloroform. The organic layer was dried over anhydrous sodium sulfate, and then the solvent was distilled off under reduced pressure. The resultant residue was suspended and washed in a mixed solvent of ethyl acetate-hexane, and taken by filtration. The filtered residue and the filtrate were combined and concentrated, and thereafter purified by silica gel column chromatography (eluent: chloroform-ammonia water (10% methanol solution); gradient: 100:0-90:10) to give the compound 6 (587 mg) as a pale brown solid.

MS (APCI) 285 [M+H]$^+$ (4) The compound 6 (578 mg) was dissolved in acetonitrile (18 mL), and the compound 7 (373 mg) and sodium carbonate (431 mg) were added thereto. The reaction mixture was stirred for 7 hours at room temperature. The reaction mixture was diluted with ethyl acetate, and washed with water. The aqueous layer was extracted with ethyl acetate, and the combined organic layer was dried over anhydrous magnesium sulfate. The solvent was distilled off under reduced pressure, and the resultant residue was purified by silica gel column chromatography (eluent: chloroform-methanol; gradient: 100:0-95:5) to give the compound 8 (535 mg) as an orange solid.

MS (APCI): 357 [M+H]$^+$ (5) The compound 8 (527 mg) was dissolved in methanol (5 mL), and a 1 mol/L aqueous sodium hydroxide solution (3 mL) was added thereto. The reaction mixture was stirred for 5 minutes at room temperature. Methanol (5 mL) and water (1 mL) were added thereto, and the reaction mixture was stirred for 25 minutes at the same temperature. The reaction mixture was concentrated under reduced pressure, and then dissolved in water. A 1 mol/L aqueous hydrochloric acid solution was added thereto. The precipitate was taken by filtration, and dried to give the compound 9 (441 mg) as a colorless solid.

MS (APCI): 343 [M+H]$^+$

Reference Example 23

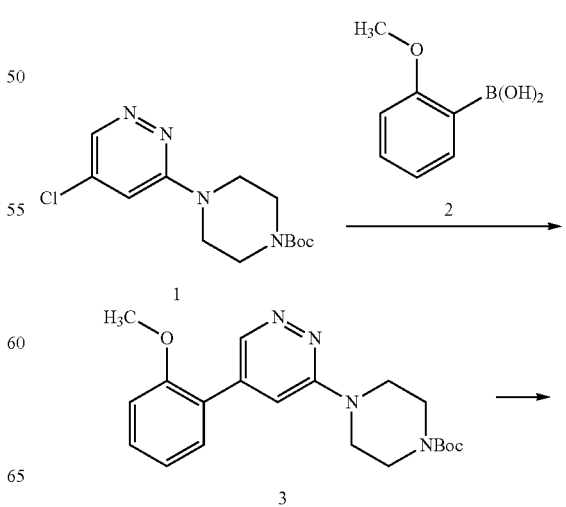

-continued

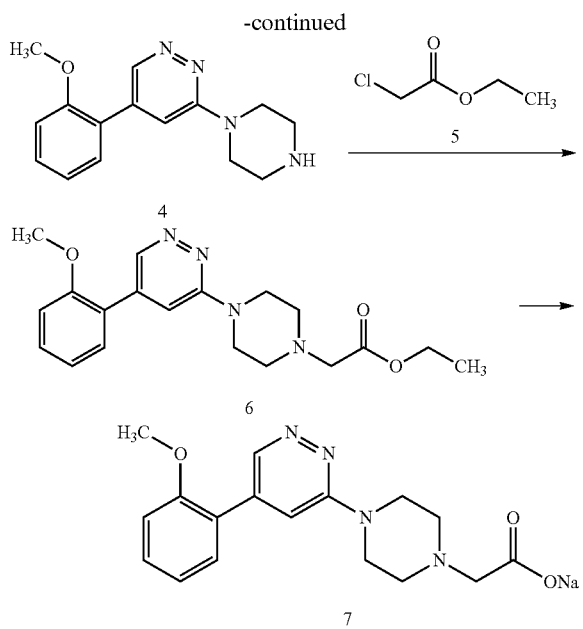

(1) The compound 1 (1.0 g), the compound 2 (1.0 g), and cesium carbonate (4.37 g) were suspended in THF (34 mL). The suspension was degassed under reduced pressure, and then back-filled with argon. To the reaction mixture were added tris(dibenzylideneacetone)dipalladium (153 mg) and tri-t-butylphosphine (10% hexane solution, 0.95 mL), and the reaction mixture was stirred for 2 hours at 80° C. The reaction mixture was cooled to room temperature, diluted with water, and then extracted with ethyl acetate. The organic layer was dried over anhydrous sodium sulfate, and the residue obtained by distilling off the solvent was purified by NH-silica gel column chromatography (eluent: hexane-ethyl acetate; gradient: 50:50-80:20) to give the compound 3 (1.19 g) as a colorless solid.

MS (APCI): 371 $[M+H]^+$ (2) To a solution of the compound 3 (1.19 g) in chloroform (6.5 mL) was added trifluoroacetic acid (6.5 mL), and the reaction mixture was stirred for 1 hour at room temperature. The reaction mixture was diluted with methanol, and then treated with packed strong cation exchange resin (PoraPak Rxn Cx, eluent: ammonia (1 mol/L methanol solution), and the eluate was concentrated under reduced pressure to give the compound 4 (870 mg) as a colorless solid.

MS (APCI) 271 $[M+H]^+$ (3) To a solution of the compound 4 (867 mg) in acetonitrile (32 mL) were added sodium carbonate (680 mg) and the compound 5 (378 μL), and the reaction mixture was stirred for 8 hours at 65° C. The reaction mixture was diluted with water, and then extracted with ethyl acetate. The organic layer was dried over anhydrous sodium sulfate. The solvent was distilled off under reduced pressure, and the resultant residue was purified by NH-silica gel column chromatography (eluent: hexane-ethyl acetate; gradient: 50:50-20:80) to give the compound 6 (915 mg) as a colorless solid.

MS (APCI): 357 $[M+H]^+$ (4) The compound 6 (915 mg) was dissolved in a mixed solvent of ethanol (12.5 mL)-THF (12.5 mL), and a 1 mol/L aqueous sodium hydroxide solution (5.1 mL) was added thereto. The reaction mixture was stirred for 1 hour at room temperature. The reaction mixture was concentrated under reduced pressure, dissolved in water, and a 1 mol/L aqueous hydrochloric acid solution was added thereto. The precipitate was taken by filtration, and dried to give the compound 7 (986 mg) as a colorless solid.

MS (APCI): 329 $[M+H]^+$

Reference Example 24

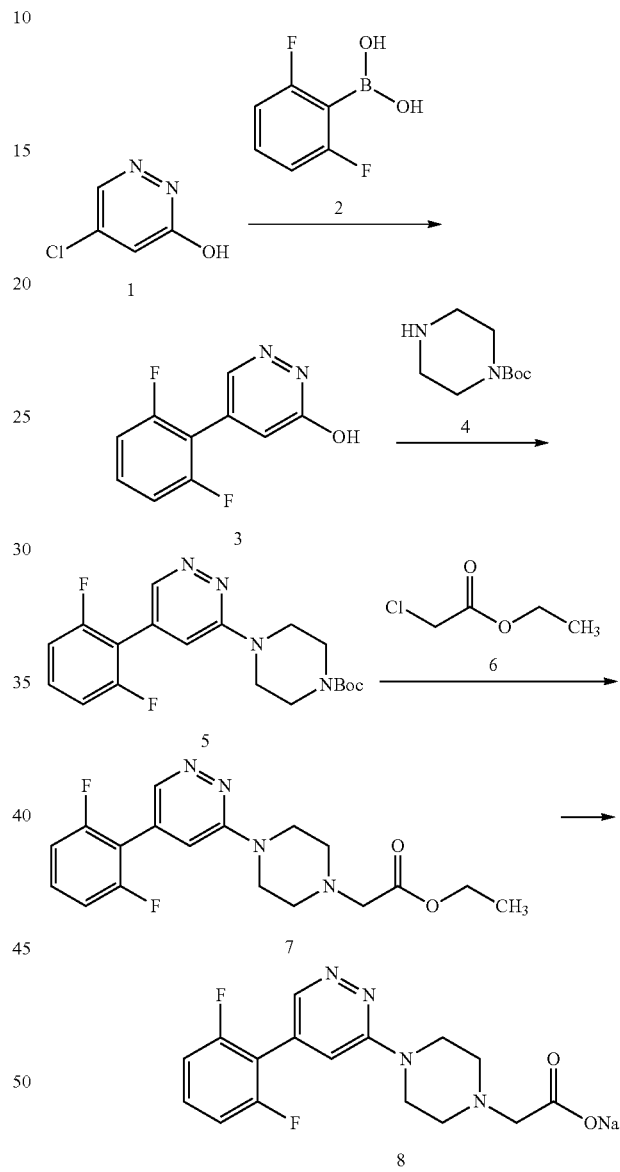

(1) The compound 1 (500 mg), the compound 2 (1.81 g), and potassium fluoride (890 mg) were suspended in THF (10 mL)-water (1 mL). The suspension was degassed under reduced pressure, and then back-filled with argon. To the reaction mixture were added tris(dibenzylideneacetone)dipalladium (350 mg) and tri-t-butylphosphine (10% hexane solution, 766 μL), and the reaction mixture was stirred for 2 hours at 80° C. The reaction mixture was cooled to room temperature, diluted with water, and then extracted with ethyl acetate. The organic layer was washed with saturated brine, dried over anhydrous sodium sulfate, and the solvent was distilled off under reduced pressure. The resultant residue was purified by silica gel column chromatography (eluent: chloroform-ethyl acetate; gradient: 80:20-50:50) to give the compound 3 (618 mg) as a colorless solid.

MS (APCI): 209 [M+H]$^+$ (2) The compound 3 (614 mg), the compound 4 (1.65 g), 1H-benzotriazol-1-yloxytris (dimethylamino)phosphonium hexafluorophosphate (BOP, 2.0 g), and diazabicycloundecene (1.32 mL) were added to DMF (30 mL). After argon substitution, the reaction mixture was stirred for 13.5 hours at 80° C. After cooled to room temperature, water and a saturated aqueous solution of sodium hydrogen carbonate were added to the reaction mixture, followed by extraction with chloroform. The organic layer was dried over anhydrous magnesium sulfate, and then the solvent was distilled off under reduced pressure. The resultant residue was purified by silica gel column chromatography (eluent: hexane-ethyl acetate; gradient: 65:35-50:50) to give the compound 5 (808 mg) as a pale yellow solid.

MS (APCI): 377 [M+H]$^+$ (3) The compound 5 (791 mg) was dissolved in chloroform (10 mL), and trifluoroacetic acid (7.9 mL) was added thereto. The reaction mixture was stirred for 1 hour at room temperature. The reaction mixture was diluted with methanol, and then treated with packed strong cation exchange resin (PoraPak Rxn Cx, eluent: ammonia (1 mol/L methanol solution)). The eluate was concentrated under reduced pressure. The resultant residue was dissolved in acetonitrile (15 mL), and the compound 6 (270 µL) and magnesium carbonate (445 mg) were added thereto. The reaction mixture was stirred for 7.5 hours at 60° C. The reaction mixture was diluted with ethyl acetate, washed with water and saturated brine, and dried over anhydrous magnesium sulfate. The solvent was distilled off under reduced pressure, and the resultant residue was purified by silica gel column chromatography (eluent: chloroform-methanol; gradient: 100:0-95:5) to give the compound 7 (614 mg) as a yellow liquid.

MS (APCI): 363 [M+H]$^+$ (4) The compound 7 (595 mg) was dissolved in ethanol (6 mL), and a 1 mol/L aqueous sodium hydroxide solution (3.3 mL) was added thereto. The reaction mixture was stirred for 30 minutes at room temperature. The reaction mixture was concentrated, dissolved in water, and a 1 mol/L aqueous hydrochloric acid solution was added thereto. The precipitate was taken by filtration, and dried to give the compound 8 (434 mg) as a colorless solid.

MS (APCI): 335 [M+H]$^+$

Experimental Example 1 (Inhibitory Effect on hCYP11B2)

<Experimental Method>

The pcDNA3.1-human CYP11B2 plasmid was transfected into a Chinese hamster lung fibroblast V79 cell line to produce a cell line stably expressing human CYP11B2 gene.

The cells were cultured and grown in the Dulbecco's modified Eagle's/Ham's medium supplemented with 10% fetal bovine serum and 1% G418 disulfate solution under the environment of 37° C., 95% air, and 5% $CO_2$, and the grown cells were harvested.

Then, the cells were fractionated to obtain mitochondria by reference to a method described in Chabre et al. JCE & M 85 (11) 4060-68, 2000. In particular, the cells suspended in a 5 mmol/L Tris-HCl buffer (pH 7.4) containing 250 mmol/L sucrose were homogenized in a Teflon (Registered Trademark) Potter Elvehjem homogenizer, and then the suspension was centrifuged (800×g, 15 min.). The supernatant was separated and again centrifuged (10000×g, 15 min.) to obtain a pellet (mitochondrial fraction).

The mitochondrial fraction diluted with a buffer containing 10 mmol/L $KH_2PO_4$, 10 mmol/L Tris, 20 mmol/L KCl, 25 mmol/L sucrose, 5 mmol/L $MgCl_2$, and 0.05% bovine serum albumin was dispensed to a 96-well plate. 0.5 µmol/L Deoxycorticosterone, 150 µmol/L NADPH and a compound of each concentration were added to each well, and incubated for 1.5-2 hours at room temperature to produce aldosterone. An amount of the produced aldosterone in the incubated solution was determined by using HTRF (Homogeneous Time Resolved Fluorescence) method.

$IC_{50}$ (nmol/L) was calculated by analyzing the aldosterone production inhibition rate (%) of each concentration of compounds by non-linear regression to a logistic curve.

<Experimental Results>

TABLE 15

| Example No. | hCyp11B2 $IC_{50}$ (nmol/L) |
|---|---|
| 1 | 6.6 |
| 2 | 3.0 |
| 3 | 8.8 |
| 4 | 3.3 |
| 5 | 14 |
| 6 | 13 |
| 7 | 4.8 |
| 8 | 4.9 |
| 9 | 5.8 |
| 10 | 9.2 |
| 11 | 18 |
| 12 | 100 |
| 13 | 11 |
| 14 | 30 |
| 15 | 18 |
| 16 | 6.9 |
| 17 | 17 |
| 18 | 14 |
| 19 | 9.0 |
| 20 | 4.5 |
| 21 | 28 |
| 22 | 19 |
| 23 | 63 |
| 24 | 15 |
| 25 | 18 |
| 26 | 14 |
| 27 | 42 |
| 28 | 10 |
| 29 | 37 |
| 30 | 13 |
| 31 | 5.1 |
| 32 | 9.6 |
| 33 | 3.9 |
| 34 | 7.0 |
| 35 | 8.6 |
| 36 | 4.8 |
| 37 | 8.4 |
| 38 | 8.7 |
| 39 | 4.3 |
| 40 | 4.0 |
| 41 | 9.6 |
| 42 | 40 |
| 43 | 41 |
| 44 | 56 |
| 45 | 20 |
| 46 | 26 |
| 47 | 22 |
| 48 | 14 |
| 49 | 7.5 |
| 50 | 48 |
| 51 | 17 |
| 52 | 18 |
| 53 | 25 |
| 54 | 16 |
| 55 | 2.2 |
| 56 | 38 |

TABLE 15-continued

| Example No. | hCyp11B2 IC$_{50}$ (nmol/L) |
|---|---|
| 57 | 16 |
| 58 | 20 |
| 59 | 23 |
| 60 | 18 |
| 61 | 2.5 |
| 62 | 11 |
| 63 | 8.8 |
| 64 | 6.6 |
| 65 | 9.1 |
| 66 | 9.6 |
| 67 | 41 |
| 68 | 8.3 |
| 69 | 12 |
| 70 | 6.0 |
| 71 | 16 |
| 72 | 11 |
| 73 | 18 |
| 74 | 19 |
| 75 | 41 |
| 76 | 103 |
| 77 | 22 |
| 78 | 28 |
| 79 | 21 |
| 80 | 17 |
| 81 | 9.1 |
| 82 | 14 |
| 83 | 102 |
| 84 | 32 |
| 85 | 7.0 |
| 86 | 8.4 |
| 87 | 18 |
| 88 | 7.8 |
| 89a | 7.4 |
| 89b | 10 |
| 90a | 33 |
| 90b | 76 |
| 91a | 30 |
| 91b | 12 |
| 92 | 83 |

INDUSTRIAL APPLICABILITY

A compound [I] of the present invention or a pharmaceutically acceptable salt thereof has an inhibitory activity against aldosterone synthetase, and therefore, it is useful as a medicament for preventing or treating various diseases and/or disease states evoked by an increased level of aldosterone and/or overproduction of aldosterone, such as hypertension, primary aldosteronism, or for improving prognosis of these diseases.

The invention claimed is:

1. A compound of the following formula [I]:

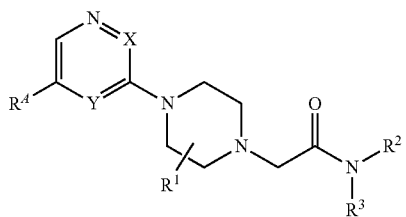

wherein
X and Y represent any of the following (1) to (3):
(1) X is N, and Y is CH or C—R$^Y$,
(2) X is CH, and Y is N, or
(3) X is CH, and Y is CH;
R$^Y$ represents an alkyl group;
R$^4$ represents a cycloalkyl group which may be substituted, a cycloalkenyl group which may be substituted, an aryl group which may be substituted, or a 6- to 10-membered monocyclic or bicyclic heteroaryl group which may be partially hydrogenated and may be substituted;
R$^1$ represents a hydrogen atom, or an alkyl group;
R$^2$ represents an alkyl group which may be substituted, a cycloalkyl group which may be substituted, an aliphatic heterocyclic group which may be substituted, or a heteroaryl group which may be partially hydrogenated and may be substituted; and
R$^3$ represents a hydrogen atom, or an alkyl group,
wherein
substituents of the cycloalkyl group which may be substituted, the cycloalkenyl group which may be substituted, the aryl group which may be substituted, and the 6- to 10-membered monocyclic or bicyclic heteroaryl group which may be partially hydrogenated and may be substituted, represented by R$^4$, are 1-3 groups each independently selected from the group consisting of a halogen atom, a cyano group, an alkyl group, a haloalkyl group, an alkoxyalkyl group, and an alkoxy group,
in the aryl group which may be substituted, represented by R$^4$, the aryl moiety is phenyl or naphthyl,
in the 6- to 10-membered heteroaryl group which may be partially hydrogenated and may be substituted, represented by R$^4$, the heteroaryl moiety is pyridyl, pyrazinyl, pyrimidinyl, pyridazinyl, thiazinyl, triazinyvl, indolyl, isoindolyl, indazolyl, benzimidazolyvl, benzothiazolyl, benzofuranyvl, quinolyl, isoquinolyl, imidazopyridyl, or benzopyranyl;
a substituent of (i) the alkyl group which may be substituted, represented by R$^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group,
substituents of (ii) the cycloalkyl group which may be substituted, (iii) the aliphatic heterocyclic group which may be substituted, and (iv) the heteroaryl group which may be partially hydrogenated and may be substituted, represented by R$^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iv), the aliphatic heterocyclic group is a group independently selected from the group consisting of azetidinyl, oxetanyl, pyrrolidinyl, tetrahydrothienyl, tetrahydrofuranyl, thiazolidinyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, and 3-oxo-9-azabicyclo[3.3.1]nonyl, in the respective substituents of the above (i) to (iv), the heteroaryl group is a group independently selected from the group consisting of pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, and benzopyranyl, in the aliphatic heterocyclic group which may be substituted, represented by $R^2$, the aliphatic heterocyclic moiety is azetidinyl, oxetanyl, pyrrolidinyl, tetrahydrothienyl, tetrahydrofuranyl, thiazolidinyl, piperidinyl, piperazinyl, morpholinyl, thiomorpholinyl, homomorpholinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, and in the heteroaryl group which may be partially hydrogenated and may be substituted, represented by $R^2$, the heteroaryl moiety is pyrrolyl, furanyl, thienyl, imidazolyl, pyrazolyl, oxazolyl, thiazolyl, triazolyl, tetrazolyl, pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl, or a pharmaceutically acceptable salt thereof.

2. The compound according to claim 1, wherein substituents of the cycloalkyl group which may be substituted, the cycloalkenyl group which may be substituted, the aryl group which may be substituted, and the 6- to 10-membered monocyclic or bicyclic heteroaryl group which may be partially hydrogenated and may be substituted, represented by $R^4$, are 1-3 groups each independently selected from the group consisting of a halogen atom, a cyano group, an alkyl group, a haloalkyl group, an alkoxyalkyl group, and an alkoxy group, in the aryl group which may be substituted, represented by $R^4$, the aryl moiety is phenyl or naphthyl, in the 6- to 10-membered monocyclic or bicyclic heteroaryl group which may be partially hydrogenated and may be substituted, represented by $R^4$, the heteroaryl moiety is pyridyl, indazolyl, or benzofuranyl;

a substituent of (i) the alkyl group which may be substituted, represented by $R^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, substituents of (ii) the cycloalkyl group which may be substituted, (iii) the aliphatic heterocyclic group which may be substituted, and (iv) the heteroaryl group which may be partially hydrogenated and may be substituted, represented by $R^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iv), the aliphatic heterocyclic group is a group independently selected from piperidinyl, piperazinyl, morpholinyl, thiomorpholinyl, and tetrahydropyranyl, in the respective substituents of the above (i) to (iv), the heteroaryl group is independently a pyrimidinyl group, in the aliphatic heterocyclic group which may be substituted, represented by $R^2$, the aliphatic heterocyclic moiety is pyrrolidinyl, piperidinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, and in the heteroaryl group which may be partially hydrogenated and may be substituted, represented by $R^2$, the heteroaryl moiety is pyrazolyl, pyridyl, or benzimidazolyl, or a pharmaceutically acceptable salt thereof.

3. The compound according to claim 2, wherein $R^A$ is (1) a cycloalkyl group which may be substituted with an alkyl group, (2) a cycloalkenyl group which may be substituted with an alkyl group, (3) a phenyl group which may be substituted with 1-3 groups independently selected from the group consisting of a halogen atom, an alkyl group, a haloalkyl group, an alkoxyalkyl group, and an alkoxy group, (4) a naphthyl group, or (5) a heteroaryl group which may be partially hydrogenated and may be substituted with 1-2 groups independently selected from the group consisting of a cyano group, an alkyl group, and a haloalkyl group, in the heteroaryl group which may be partially hydrogenated and may be substituted, represented by $R^4$, the heteroaryl moiety is pyridyl, indazolyl, or benzofuranyl, $R^1$ is a hydrogen atom, or an alkyl group, $R^2$ is (i) an alkyl group which may be substituted with 1-3 groups independently selected from the group consisting of a hydroxyl group; a halogen atom; and an aliphatic heterocyclic group which may be substituted with 1-2 substituents independently selected from the group consisting of a hydroxyl group, an oxo group, an alkyl group, an alkoxycarbonyl group, and an alkylsulfonyl group (wherein the aliphatic heterocyclic group is a piperidinyl group, a piperazinyl group, a morpholinyl group, or a thiomorpholinyl group), (ii) a cycloalkyl group which may be substituted with 1-3 groups independently selected from the group consisting of a hydroxyl group; an alkyl group which may be substituted with a hydroxyl group; an alkoxy group which may be substituted with a carbamoyl group which may be substituted with 1-2 alkyl groups; an amino group which may be substituted with 1-2 groups independently selected from the group consisting of an alkyl group, and an alkanoyl group; and an aliphatic heterocyclic group which may be substituted with 1-2 groups independently selected from the group consisting of a hydroxyl group, and an oxo group (wherein the aliphatic heterocyclic group is a piperidinyl group, a morpholinyl group, or a piperazinyl group), (iii) an aliphatic heterocyclic group which may be substituted with 1-3 groups independently selected from the group consisting of a halogen atom; a hydroxyl group; an oxo group; an alkyl group which may be substituted with 1-2 groups independently selected from the group consisting of a carbamoyl group which may be substituted with 1-2 alkyl groups, a hydroxyl group, and an alkylsulfonyl group; an alkoxy group; an alkoxycarbonyl group; a tetrahydropyranyl group; and a pyrimidinyl group, or (iv) a heteroaryl group which may be partially hydrogenated and may be substituted with an alkyl group which may be substituted with a carbamoyl group which may be substituted with 1-2 alkyl groups, in the aliphatic heterocyclic group which may be substituted, represented by $R^2$, the aliphatic heterocyclic moiety is pyrrolidinyl, piperidinyl, tetrahydrothiopyranyl, tetrahydropyranyl, 1-azabicyclo[2.2.2] octyl(quinuclidinyl), 8-azabicyclo[3.2.1]octyl, 3-oxabicyclo[3.3.1]nonyl, or 3-oxo-9-azabicyclo[3.3.1]nonyl, in the heteroaryl group which may be partially hydrogenated and may be substituted, represented by $R^2$, the heteroaryl moiety is pyrazolyl, pyridyl, or benzimidazolyl, and $R^3$ is a hydrogen atom, or a pharmaceutically acceptable salt thereof.

4. The compound according to claim 2, wherein
X is N, Y is CH or C—$R^Y$,
$R^Y$ is an alkyl group,
$R^4$ is
(1) a cyclohexyl group which may be substituted with an alkyl group,
(2) a cyclohexenyl group which may be substituted with an alkyl group,
(3) a phenyl group which may be substituted with 1-2 groups independently selected from the group consisting of a halogen atom, an alkyl group, a haloalkyl group, an alkoxyalkyl group, and an alkoxy group,
(4) a naphthyl group, or
(5) a heteroaryl group which may be partially hydrogenated and may be substituted with a cyano group, in the heteroaryl group which may be partially hydrogenated and may be substituted, represented by $R^4$, the heteroaryl moiety is pyridyl, or benzofuranyl, $R^1$ is a hydrogen atom, $R^2$ is
(i) an alkyl group which may be substituted with 1-3 groups independently selected from the group consisting of a hydroxyl group; and an aliphatic heterocyclic group which may be substituted with 1-2 groups independently selected from the group consisting of an oxo group, an alkyl group, an alkoxycarbonyl group, and an alkylsulfonyl group (wherein the aliphatic heterocyclic group is selected from a piperidinyl group, a piperazinyl group, a morpholinyl group, and a thiomorpholinyl group), (ii) a cycloalkyl group which may be substituted with 1-3 groups independently selected from the group consisting of an alkoxy group which may be substituted with a carbamoyl group which may be substituted with 1-2 alkyl groups; an amino group which may be substituted with 1-2 groups independently selected from the group consisting of an alkyl group, and an alkanoyl group; and a morpholinyl group, (iii) an aliphatic heterocyclic group which may be substituted with 1-3 groups independently selected from the group consisting of a halogen atom; a hydroxyl group; an oxo group; an alkyl group which may be substituted with 1-2 groups independently selected from the group consisting of a carbamoyl group which may be substituted with 1-2 alkyl groups, a hydroxyl group, and an alkylsulfonyl group; an alkoxycarbonyl group; and an alkoxy group, or (iv) a pyridyl group, in the aliphatic heterocyclic group which may be substituted, represented by $R^2$, the aliphatic heterocyclic moiety is piperidinyl, tetrahydrothiopyranyl, or tetrahydropyranyl, and $R^3$ is a hydrogen atom, or a pharmaceutically acceptable salt thereof.

5. The compound according to claim 2, wherein
X is CH, Y is N,
$R^4$ is
(1) an cyclohexyl group which may be substituted with an alkyl group,
(2) a phenyl group which may be substituted with 1-2 groups independently selected from the group consisting of a halogen atom, an alkyl group, and a haloalkyl group, or
(3) a heteroaryl group which may be partially hydrogenated and may be substituted with 1-2 groups independently selected from the group consisting of a cyano group, and an alkyl group, in the heteroaryl group which may be partially hydrogenated and may be substituted, represented by $R^4$, the heteroaryl moiety is pyridyl, indazolyl, or benzofuranyl, $R^1$ is a hydrogen atom or an alkyl group, $R^2$ is
(i) an alkyl group which may be substituted with 1-3 groups independently selected from the group consisting of a hydroxyl group; a halogen atom; and a piperidinyl group which may be substituted with 1-2 groups independently selected from the group consisting of a hydroxyl group, and an alkyl group, (ii) a cycloalkyl group which may be substituted with 1-3 groups independently selected from the group consisting of a hydroxyl group; an alkyl group which may be substituted with a hydroxyl group; an alkoxy group; an amino group which may be substituted with 1-2 groups independently selected from the group consisting of an alkyl group, and an alkanoyl group; and an aliphatic heterocyclic group which may be substituted with 1-2 oxo groups (wherein the aliphatic heterocyclic group is selected from a morpholinyl group or a piperazinyl group), (iii) an aliphatic heterocyclic group which may be substituted with 1-3 groups independently selected from the group consisting of an oxo group; an alkyl group which may be substituted with an alkylsulfonyl group; a tetrahydropyranyl group; and a pyrimidinyl group, or (iv) a pyrazolyl group which may be substituted with an alkyl group which may be substituted with a carbamoyl group which may be substituted with 1-2 alkyl groups, in the aliphatic heterocyclic group which may be substituted, represented by $R^2$, the aliphatic heterocyclic moiety is pyrrolidinyl, piperidinyl, tetrahydrothiopyranyl, or 1-azabicyclo[2.2.2]octyl(quinuclidinyl), and $R^3$ is a hydrogen atom, or a pharmaceutically acceptable salt thereof.

6. The compound according to claim 2, wherein
X is CH, Y is CH,
$R^4$ is
(1) a cyclohexyl group which may be substituted with an alkyl group,
(2) a cyclohexenyl group which may be substituted with an alkyl group,
(3) a phenyl group which may be substituted with 1-2 groups independently selected from the group consisting of a halogen atom, and an alkyl group, or
(4) a heteroaryl group which may be partially hydrogenated and may be substituted with 1-2 groups independently selected from the group consisting of a cyano group, an alkyl group, and an haloalkyl group, in the heteroaryl group which may be partially hydrogenated and may be substituted, represented by $R^4$, the heteroaryl moiety is pyridyl, indazolyl, or benzofuranyl;

$R^1$ is a hydrogen atom,
$R^2$ is
(i) an alkyl group which may be substituted with a hydroxyl group,
(ii) a cycloalkyl group which may be substituted with 1-3 groups independently selected from the group consisting of an amino group which may be substituted with 1-2 groups independently selected from the group consisting of an alkyl group, and an alkanoyl group; and a piperidinyl group which may be substituted with a hydroxyl group,
(iii) an aliphatic heterocyclic group which may be substituted with 1-3 groups independently selected from the group consisting of a hydroxyl group; an alkyl group; and an alkoxycarbonyl group, or
(iv) a heteroaryl group which may be partially hydrogenated and may be substituted with an alkyl group which may be substituted with a carbamoyl group which may be substituted with 1-2 alkyl groups, in the aliphatic heterocyclic group which may be substituted, represented by $R^2$, the aliphatic heterocyclic moiety is 8-azabicyclo[3.2.1]octyl, 3-oxabicyclo[3.3.1]nonyl, or 3-oxo-9-azabicyclo[3.3.1]nonyl, in the heteroaryl group which may be partially hydrogenated and may be substituted, represented by $R^2$, the heteroaryl moiety is pyrazolyl, or benzimidazolyl, and $R^3$ is a hydrogen atom, or a pharmaceutically acceptable salt thereof.

7. The compound according to claim 1, wherein
X and Y are any of the following (1)-(3),
(1) X is N, and Y is CH,
(2) X is CH, and Y is N, or
(3) X is CH, and Y is CH;

$R^4$ is an aryl group which may be substituted, or a 6- to 10-membered monocyclic or bicyclic heteroaryl group which may be partially hydrogenated and may be substituted;

$R^1$ is a hydrogen atom;

$R^2$ is an alkyl group which may be substituted, a cycloalkyl group which may be substituted, or an aliphatic heterocyclic group which may be substituted; and $R^3$ is a hydrogen atom, or a pharmaceutically acceptable salt thereof.

8. The compound according to claim 7, wherein
substituents of the aryl group which may be substituted, and the 6- to 10-membered monocyclic or bicyclic heteroaryl group which may be partially hydrogenated and may be substituted, represented by $R^4$, are 1-3 groups each independently selected from the group consisting of a halogen atom, a cyano group, an alkyl group, a haloalkyl group, an alkoxyalkyl group, and an alkoxy group, in the aryl group which may be substituted, represented by $R^4$, the aryl moiety is phenyl, or naphthyl, in the 6- to 10-membered monocyclic or bicyclic heteroaryl group which may be partially hydrogenated and may be substituted, represented by $R^4$, the heteroaryl moiety is pyridyl, pyrazinyl, pyrimidinyl, pyridazinyl, thiazinyl, triazinyl, indolyl, isoindolyl, indazolyl, benzimidazolyl, benzothiazolyl, benzofuranyl, quinolyl, isoquinolyl, imidazopyridyl, or benzopyranyl;

a substituent of (i) the alkyl group which may be substituted, represented by $R^2$, is 1-3 groups independently selected from the group consisting of a halogen atom; a hydroxyl group; an oxo group; a carbamoyl group which may be substituted with 1-2 alkyl groups; an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and an alkoxycarbonyl group; an alkoxycarbonyl group; an amino group which may be substituted with 1-2 groups independently selected from the group consisting of an alkyl group and an alkanoyl group; and a heteroaryl group, substituents of (ii) the cycloalkyl group which may be substituted, and (iii) the aliphatic heterocyclic group which may be substituted, represented by $R^2$, are 1-3 groups each independently selected from the group consisting of a halogen atom; a hydroxyl group; an oxo group; an alkyl group which may be substituted with 1-3 groups independently selected from the group consisting of a hydroxyl group, a carbamoyl group which may be substituted with 1-2 alkyl groups, and an alkylsulfonyl group; an alkoxy group which may be substituted with a carbamoyl group which may be substituted with 1-2 alkyl groups; an aliphatic heterocyclic group which may be substituted with 1-3 groups independently selected from the group consisting of a hydroxyl group, an oxo group, an alkyl group, an alkylsulfonyl group, and alkoxycarbonyl group; an alkoxycarbonyl group; an amino group which may be substituted with 1-2 groups independently selected from the group consisting of an alkyl group and an alkanoyl group; and a heteroaryl group, in the respective substituents of the above (i) to (iii), the aliphatic heterocyclic group is a group independently selected from the group consisting of piperidinyl, piperazinyl, morpholinyl, thiomorpholinyl, and tetrahydropyranyl, in the respective substituents of the above (i) to (iii), the heteroaryl group is independently a pyrimidinyl group, in the aliphatic heterocyclic group which may be substituted, represented by $R^2$, the heterocyclic moiety is pyrrolidinyl, piperidinyl, tetrahydrothiopyranyl, tetrahydropyranyl, 1-azabicyclo[2.2.2]octyl(quinuclidinyl), 8-azabicyclo[3.2.1]octyl, 3-oxabicyclo[3.3.1]nonyl, or 3-oxo-9-azabicyclo[3.3.1]nonyl, or a pharmaceutically acceptable salt thereof.

9. The compound according to claim 7, wherein $R^4$ is a phenyl group which may be substituted with a halogen atom, or an indazolyl group which may be partially hydrogenated and may be substituted with an alkyl group, and $R^2$ is (1) an alkyl group, (2) a cyclohexyl group which may be substituted with an amino group which may be substituted with 1-2 alkyl groups, or a cyclohexyl group which may be substituted with an alkoxy group, or (3) 8-azabicyclo[3.2.1]octyl which may be substituted with an alkyl group, or a pharmaceutically acceptable salt thereof.

10. A compound selected from the group consisting of 3-[4-[(trans-4-methoxycyclohexyl)carbamoylmethyl]piperazin-1-yl]-5-(1-methyl-1H-indazol-6-yl)pyrazine; 3-[4-(isopropylcarbamoylmethyl)piperazin-1-yl]-5-(1-methyl-1H-indazol-6-yl) pyrazine; 5-(4-fluorophenyl)-3-[4-[[trans-4-(N,N-dimethylamino)cyclohexyl]carbamoylmethyl] piperazin-1-yl]pyridazine; and 3-(4-chlorophenyl)-5-[4-[(exo-8-methyl-8-azabicyclo[3,2,1] octan-3-yl) carbamoylmethyl]piperazin-1-yl]pyridine, or a pharmaceutically acceptable salt thereof.

11. A pharmaceutical composition comprising the compound according to claim 1 or a pharmaceutically acceptable salt thereof as an active ingredient.

12. A method for treating diseases and/or disease states of primary aldosteronism, hypertension, heart failure, nephropathy, or sleep apnea syndrome evoked by an increased level of aldosterone and/or overproduction of aldosterone comprising administering a therapeutically effective amount of the compound according to claim 10 or a pharmaceutically acceptable salt thereof to a patient.

13. A pharmaceutical composition comprising the compound according to claim 10 or a pharmaceutically acceptable salt thereof as an active ingredient.

14. The compound according to claim 1, wherein the compound is:

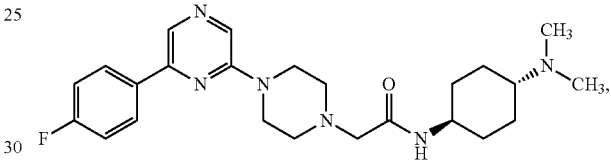

or a pharmaceutically acceptable salt thereof.

* * * * *